United States Patent
Kanamori et al.

(10) Patent No.: US 9,392,231 B2
(45) Date of Patent: *Jul. 12, 2016

(54) IMAGING DEVICE AND ENDOSCOPE FOR DETECTING AND DISPLAYING THE SHAPE OF THE MICRO-GEOMETRIC TEXTURE OF A TRANSPARENT STRUCTURE

(71) Applicant: Panasonic Corporation, Osaka (JP)

(72) Inventors: Katsuhiro Kanamori, Nara (JP); Toshinobu Matsuno, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 280 days.

This patent is subject to a terminal disclaimer.

(21) Appl. No.: 14/099,165

(22) Filed: Dec. 6, 2013

(65) Prior Publication Data

US 2014/0092227 A1 Apr. 3, 2014

Related U.S. Application Data

(63) Continuation of application No. PCT/JP2013/001675, filed on Mar. 13, 2013.

(30) Foreign Application Priority Data

May 22, 2012 (JP) .................................. 2012-116796

(51) Int. Cl.
*H04N 7/18* (2006.01)
*A61B 1/00* (2006.01)
(Continued)

(52) U.S. Cl.
CPC .............. *H04N 7/18* (2013.01); *A61B 1/00186* (2013.01); *A61B 1/05* (2013.01); *A61B 1/051* (2013.01);
(Continued)

(58) Field of Classification Search
CPC ...... A61B 1/00186; A61B 1/05; A61B 1/051; A61B 1/07; G01J 1/0209; G01J 1/0411; G01J 4/04; H04N 5/2254; H04N 5/2256; H04N 5/2354; H04N 7/18; H04N 9/045

USPC ........................................................ 348/68
See application file for complete search history.

(56) References Cited

U.S. PATENT DOCUMENTS 6,057,952 A * 5/2000 Kubo et al. ................. 359/196.1
8,672,838 B2 * 3/2014 McDowall ......... A61B 1/00009
600/129

(Continued)

FOREIGN PATENT DOCUMENTS

JP       2009-246770 A     10/2009
JP       2009246770 A  *  10/2009  ............. H04N 5/225

(Continued)

OTHER PUBLICATIONS

Murooka et al JP2009246770MT is the machine translation of the JP2009246770A could be downloaded from JPO websites, Oct. 22, 2009.*

(Continued)

*Primary Examiner* — Shan Elahi
(74) *Attorney, Agent, or Firm* — Renner, Otto, Boisselle & Sklar, LLP

(57) ABSTRACT

In image capturing processor in one embodiment comprises: an image capturing section including an image sensor that captures a polarization image of an object being illuminated with an illuminating light beam; and an image processing section. The image processing section has: a light intensity image generator which generates a light intensity image based on the output of the image sensor; a polarization degree image generator which generates a polarization degree image by calculating the degree of polarization on a pixel-by-pixel basis; a retouching section which generates a retouched polarization image by enhancing the degree of polarization of the polarization degree image at depressions on a micro-geometric surface of the object and by correcting at least one of its hue, saturation and value; and an image synthesizing section which synthesizes the retouched polarization image and the light intensity image together.

25 Claims, 42 Drawing Sheets

(51) Int. Cl.
  *A61B 1/05* (2006.01)
  *A61B 1/07* (2006.01)
  *G01J 1/02* (2006.01)
  *G01J 1/04* (2006.01)
  *G01J 4/04* (2006.01)
  *H04N 5/225* (2006.01)
  *H04N 5/235* (2006.01)
  *H04N 9/04* (2006.01)

(52) U.S. Cl.
  CPC ............. *A61B 1/07* (2013.01); *G01J 1/0209* (2013.01); *G01J 1/0411* (2013.01); *G01J 4/04* (2013.01); *H04N 5/2254* (2013.01); *H04N 5/2256* (2013.01); *H04N 5/2354* (2013.01); *H04N 9/045* (2013.01)

(56) References Cited

U.S. PATENT DOCUMENTS

| | | | | |
|---|---|---|---|---|
| 8,922,634 | B2* | 12/2014 | Namii | G03B 11/00 348/45 |
| 2002/0139920 | A1* | 10/2002 | Seibel et al. | 250/208.1 |
| 2003/0076412 | A1 | 4/2003 | Ozawa | |
| 2003/0233028 | A1* | 12/2003 | Tokuda et al. | 600/160 |
| 2005/0020926 | A1* | 1/2005 | Wiklof | A61B 1/00193 600/476 |
| 2007/0273759 | A1* | 11/2007 | Krupnick et al. | 348/45 |
| 2009/0092363 | A1* | 4/2009 | Daum et al. | 385/116 |
| 2009/0290039 | A1 | 11/2009 | Kanamori et al. | |
| 2010/0079587 | A1* | 4/2010 | Yoshida | A61B 1/00096 348/68 |
| 2010/0079757 | A1 | 4/2010 | Murooka et al. | |
| 2010/0118398 | A1* | 5/2010 | Grau | 359/465 |
| 2010/0282945 | A1 | 11/2010 | Yokogawa | |
| 2010/0289878 | A1* | 11/2010 | Sato et al. | 348/46 |
| 2011/0221885 | A1* | 9/2011 | Suzuki | G01N 21/21 348/125 |
| 2011/0267483 | A1 | 11/2011 | Kanamori | |

FOREIGN PATENT DOCUMENTS

| | | |
|---|---|---|
| JP | 2010-082271 A | 4/2010 |
| JP | 2010-104421 A | 5/2010 |
| JP | 4762369 B | 6/2011 |
| JP | 2012-009539 A | 1/2012 |
| JP | 2012-024140 A | 2/2012 |

OTHER PUBLICATIONS

International Search Report for corresponding International Application No. PCT/JP2013/001675 mailed Jun. 18, 2013.

Form PCT/ISA/237 for corresponding International Application No. PCT/JP2013/001675 dated Jun. 18, 2013 and partial English translation.

Viktor Gruev, Rob Perkins, and Timothy York, "CCD Polarization Imaging Sensor with Aluminum Nanowire Optical Filters", Aug. 30, 2010 / vol. 18, No. 18 / Optics Express pp. 19087-19094.

Xiaojin Zhao, Farid Boussaid, Amin Bermak and Vladimir G. Chigrinov, "Thin Photo-Patterned Micropolarizer Array for CMOS Image Sensors", IEEE Photonics Technology Letters, vol. 21, No. 12, Jun. 15, 2009.

Treibitz, T. and Schechner, Y.Y., "Instant 3Descatter", Proceedings of the 2006 IEEE Computer Society Conference on Computer Vision and Pattern Recognition.

* cited by examiner

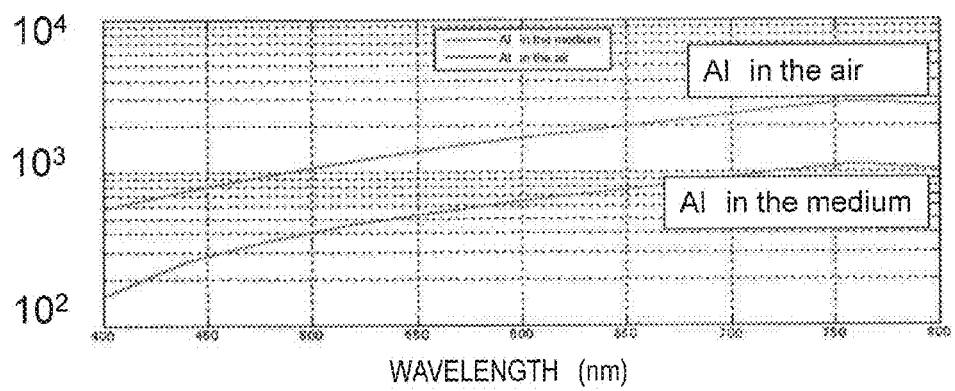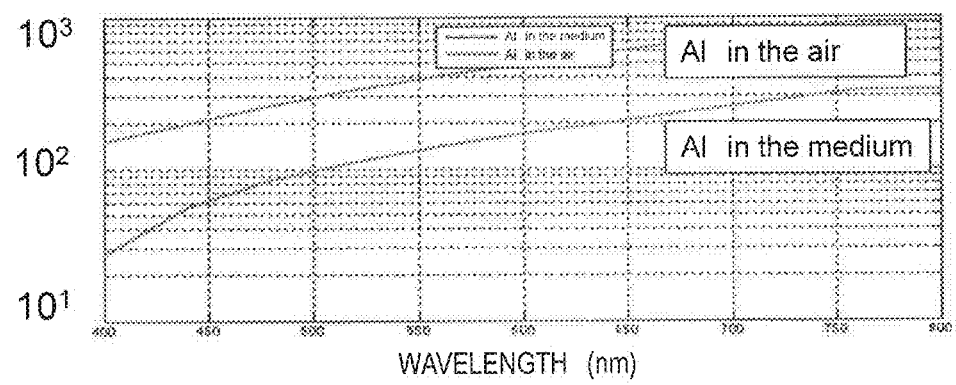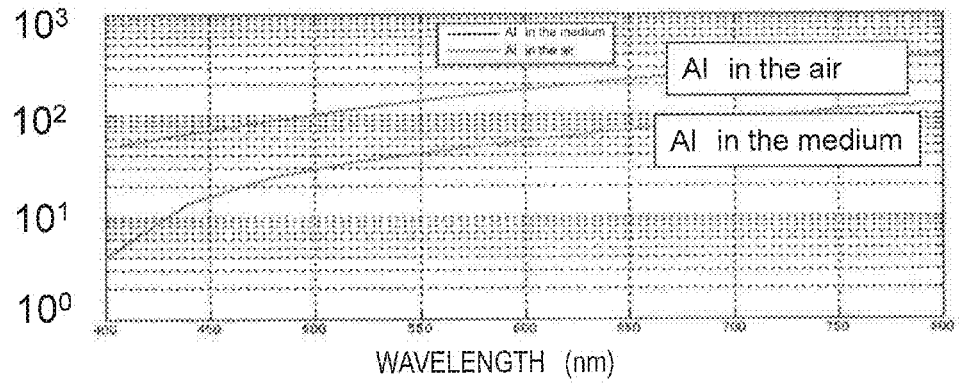
FIG. 13

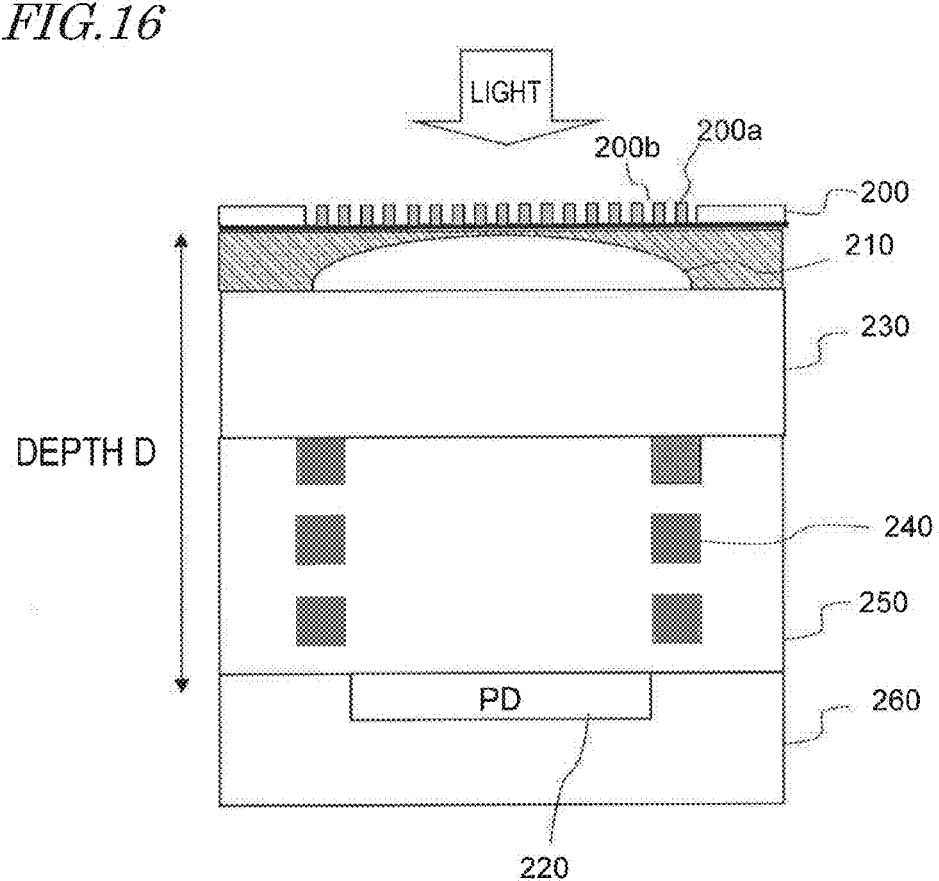

1801

$(I_1 - I_3)$  $(I_0 - I_2)$

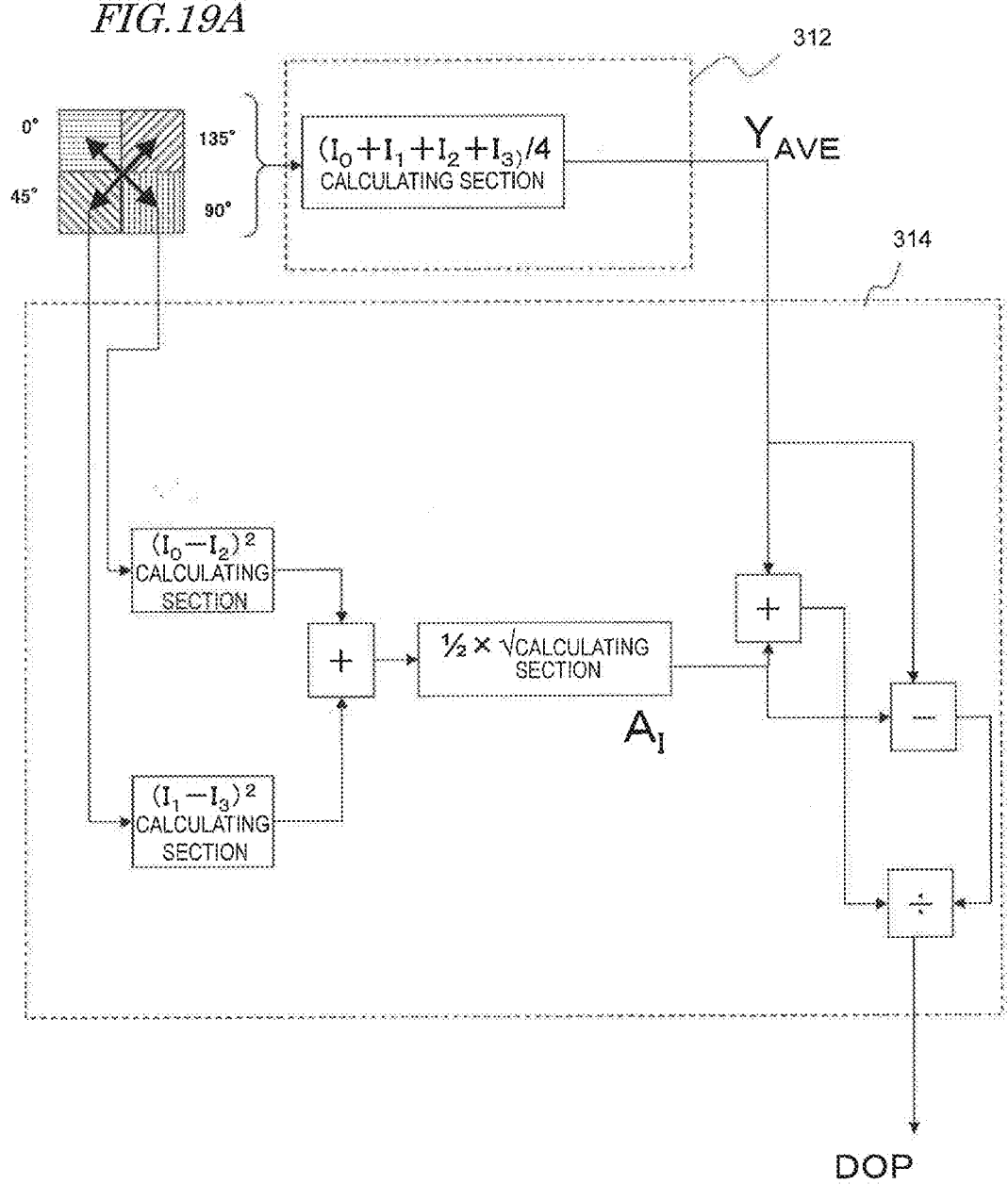

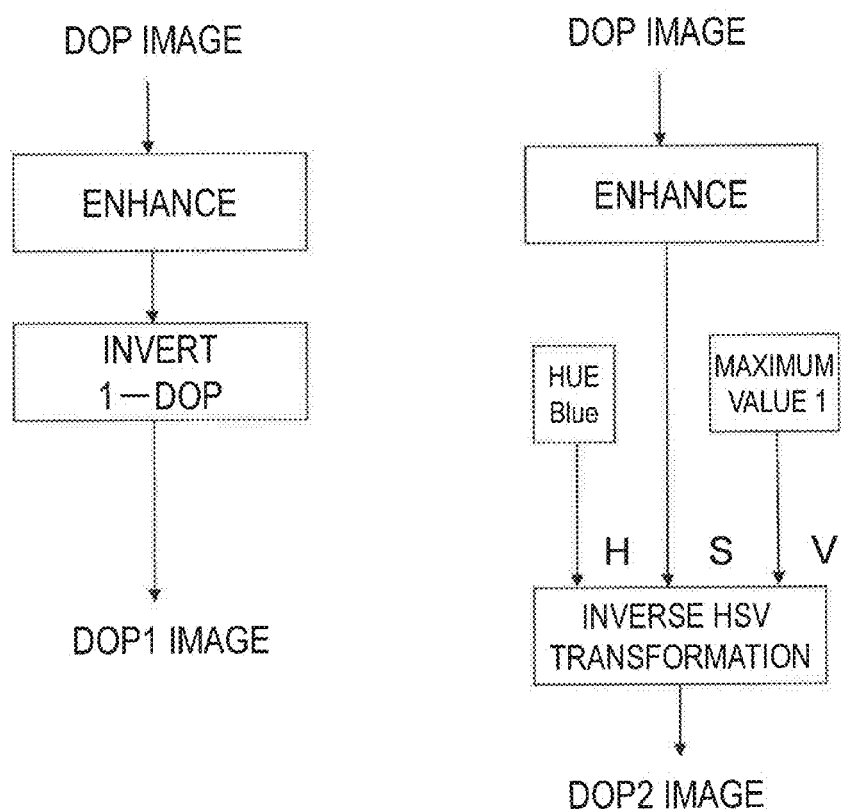

(A)

(B)

IMAGING DEVICE AND ENDOSCOPE FOR DETECTING AND DISPLAYING THE SHAPE OF THE MICRO-GEOMETRIC TEXTURE OF A TRANSPARENT STRUCTURE

This is a continuation of International Application No. PCT/JP2013/001675, with an international filing date of Mar. 13, 2013, which claims priority of Japanese Patent Application No. 2012-116796, filed on May 22, 2012, the contents of which are hereby incorporated by reference.

BACKGROUND

1. Technical Field

The present application relates to an image capturing processor which can obtain information about the surface topography of a translucent object or any other substance which is usually difficult to observe using only light intensity (luminance) information, and also relates to an endoscope which can be used to observe the surface of an organ.

2. Description of the Related Art

An image is captured through an endoscope by illuminating the wall surface of an organism's organ which is covered with a mucosa with light. When an organ is observed through an endoscope, not only a variation in the surface color of the object but also its micro-geometric surface texture need to be inspected. However, as will be described later, it is difficult to capture such a micro-geometric surface texture of the object based on the shades of the light intensity when the object is observed through an endoscope. For that reason, some blue pigment liquid such as an indigo carmine solution is sprinkled onto a mucosa as the object and the surface of the mucosa, of which the grooves are filled with such a blue pigment liquid, is observed based on its light intensities.

According to such an observation method, however, some liquid needs to be sprinkled onto the mucosa, and therefore, the object may bleed, the mucosa may change its color, and many other problems will arise. On the other hand, when a so-called "capsule endoscope" which shoots an internal body tissue in water is used, it is impossible to sprinkle any liquid onto the mucosa in the first place.

Thus, to overcome these problems, some people have proposed a polarization endoscope which uses a polarized light source and a polarization image sensor (see JP 2009-246770 A1, JP 2010-104421 A1, JP 2012-24140 A1, JP 2010-82271 A1, for example).

Meanwhile, a polarization image sensor which uses a wire grid polarizer made of aluminum is disclosed by Viktor Gruev, Rob Perkins, and Timothy York in "CCD Polarization Imaging Sensor with Aluminum Nanowire Optical Filters", 30 Aug. 2010/Vol. 18, No. 18/OPTICS EXPRESS pp. 19087-19094.

SUMMARY

According to any of these conventional techniques, however, it is difficult to detect and display the shape of the micro-geometric texture of a transparent or translucent mucosa.

Embodiments of the present disclosure provide an image capturing processor, endoscope, image processing method and program which can detect and display such a micro-geometric surface texture of an object.

In one general aspect, an image capturing processor disclosed herein comprises: an image capturing section which includes an image sensor that emits an illuminating light beam and that captures a polarization image of an object being illuminated with the illuminating light beam; and an image processing section. The optical axis of the illuminating light beam and an image capturing optical axis are substantially coaxial with each other. The image processing section includes: a light intensity image generator which generates a light intensity image based on the output of the image sensor; a polarization degree image generator which generates a polarization degree image by calculating the degree of polarization on a pixel-by-pixel basis based on the output of the image sensor; a retouching section which generates a retouched polarization image by enhancing the degree of polarization of the polarization degree image at depressions on a micro-geometric surface of the object and by correcting at least one of its hue, saturation and value; and an image synthesizing section which synthesizes the retouched polarization image and the light intensity image together.

In another aspect, an image processor disclosed herein is to be used as the image processing section in the image capturing processor of the embodiment described above. The image processor includes: a light intensity image generator which generates a light intensity image based on the output of the image sensor; a polarization degree image generator which generates a polarization degree image by calculating the degree of polarization on a pixel-by-pixel basis based on the output of the image sensor; a retouching section which generates a retouched polarization image by enhancing the degree of polarization of the polarization degree image at depressions on a micro-geometric surface of the object and by correcting at least one of its hue, saturation and value; and an image synthesizing section which synthesizes the retouched polarization image and the light intensity image together.

In another aspect, an endoscope disclosed herein is to be used in an image capturing processor according to any of the embodiments described above. The endoscope includes an image sensor that emits an illuminating light beam and that captures a polarization image of an object being illuminated with the illuminating light beam. The endoscope is arranged so that the optical axis of the illuminating light beam and an image capturing optical axis are substantially coaxial with each other.

In another aspect, an image processing method disclosed herein is designed to perform image processing based on data about a polarization image that has been captured by an image sensor in a state where an object is illuminated with an illuminating light beam so that the optical axis of the illuminating light beam and an image capturing optical axis are substantially coaxial with each other. The method includes the steps of: generating a light intensity image based on the output of the image sensor; generating a polarization degree image by calculating the degree of polarization on a pixel-by-pixel basis based on the output of the image sensor; generating a retouched polarization image by enhancing the degree of polarization of the polarization degree image at depressions on a micro-geometric surface of the object and by correcting at least one of its hue, saturation and value; and synthesizing the retouched polarization image and the light intensity image together.

In another aspect, an image processing program disclosed herein is designed to perform image processing based on data about a polarization image that has been captured by an image sensor in a state where an object is illuminated with an illuminating light beam so that the optical axis of the illuminating light beam and an image capturing optical axis are substantially coaxial with each other. The program is defined to make a computer perform the steps of: generating a light intensity image based on the output of the image sensor; generating a polarization degree image by calculating the degree of polarization on a pixel-by-pixel basis based on the output of the image sensor; generating a retouched polarization image by enhancing the degree of polarization of the polarization degree image at depressions on a micro-geometric surface of the object and by correcting at least one of its hue, saturation and value; and synthesizing the retouched polarization image and the light intensity image together.

According to embodiments of the present disclosure, even if the object is transparent or translucent, an image which allows the viewer to sense depressions on the micro-geometric surface of the object easily can be obtained.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 13 shows the wavelength dependences (based on the results of simulations) of the TM transmittance and extinction ratio of wire grid polarizers (where P=200 nm) when there is a background medium (where n=1.46) and, when there are no such media.

FIG. 16 illustrates a cross-sectional structure of a wire grid polarizer of a monochrome broadband polarization image sensor according to the first embodiment (in which the wire grid polarizer is arranged at the top).

FIG. 19A illustrates what kind of arithmetic processing is carried out by a light intensity image generator and a polarization degree image generator according to the first embodiment.

FIG. 19B illustrates what kind of image processing is carried out by a retouching section according to the first embodiment.

DETAILED DESCRIPTION

Figure 1A:
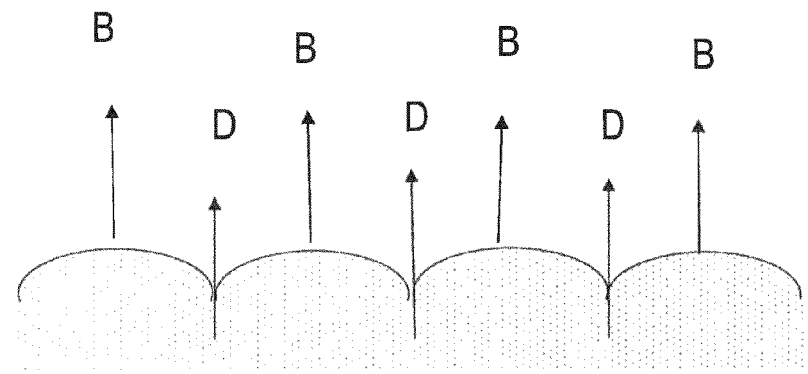
FIG. 1A schematically illustrates a light intensity distribution caused by specular reflection from a translucent micro-geometric structure.

The present disclosure provides the following image capturing processor, image processor, image processing method and image processing program:

(1) An image capturing processor comprising: an image capturing section which includes an image sensor that emits an illuminating light beam and that captures a polarization image of an object being illuminated with the illuminating light beam; and an image processing section, wherein the optical axis of the illuminating light beam and an image capturing optical axis are substantially coaxial with each other, and the image processing section includes: a light intensity image generator which generates a light intensity image based on the output of the image sensor; a polarization degree image generator which generates a polarization degree image by calculating the degree of polarization on a pixel-by-pixel basis based on the output of the image sensor; a retouching section which generates a retouched polarization image by enhancing the degree of polarization of the polarization degree image at depressions on a micro-geometric surface of the object and by correcting at least one of its hue, saturation and value; and an image synthesizing section which synthesizes the retouched polarization image and the light intensity image together.

(2) The image capturing processor of (1), wherein the image capturing section sequentially emits, as the illuminating light beams, non-polarized light beams in different colors, and the image sensor includes an array of polarizers and an array of photoelectric transducers.

(3) The image capturing processor of (1), wherein the image capturing section emits a non-polarized white light beam as the illuminating light beam, and the image sensor includes an array of polarizers, an array of color mosaic filters and an array of photoelectric transducers.

(4) The image capturing processor of (1), wherein the image capturing section sequentially emits polarized light beams, of which the polarization plane faces at least three different directions, as the illuminating light beams, and the image sensor includes an array of color mosaic filters and an array of photoelectric transducers.

(5) The image capturing processor of (1), wherein the retouching section generates the retouched polarization degree image by decreasing the light intensity of depressions on the micro-geometric surface of the object of the polarization degree image.

(6) The image capturing processor of (1), wherein the retouching section sets the color saturation to be the enhanced degree of polarization and also sets the color hue and value to be particular numerical values, thereby converting a set of the hue, saturation and value from an HSV space into an RGB space.

(7) The image capturing processor of (6), wherein the retouching section generates the retouched polarization degree image so that the depressions on the micro-geometric surface are displayed in dark blue.

(8) The image capturing processor of (1), wherein the polarization degree image generator detects points with local maximum intensities of a polarized light beam which is produced by double reflection from the micro-geometric surface of the object and a polarized light beam resulting from internally diffused light in the object as the depressions on the micro-geometric surface of the object.

(9) The image capturing processor of (2) or (3), wherein the array of polarizers has a polarizer mosaic structure in which a plurality of polarizer units are arranged in columns and rows, each polarizer unit including four polarizers, of which the polarization transmission axes directions are different from each other and which are arranged in two columns and two rows.

(10) The image capturing processor of (9), wherein the polarization degree image generator determines the degree of polarization based on the square of the difference between two pixel values which are associated with two diagonal polarizers in the two by two matrix of each polarizer unit.

(11) The image capturing processor of (2), wherein the image capturing section emits time-sequentially non-polarized light beams in red, green and blue, and the image sensor is a monochrome broadband polarization image sensor which is able to obtain a polarization image in the entire visible radiation wavelength range.

(12) The image capturing processor of (3) or (4), wherein the image sensor is a color polarization image sensor.

(13) The image capturing processor of (2) or (3), wherein the array of polarizers is an arrangement of metallic wire grid polarizers which have mutually different polarization transmission axis directions.

(14) The image capturing processor of (2) or (3), wherein the image sensor includes a micro lens which is arranged either closer to, or more distant from, the object than the array of polarizers is.

(15) The image capturing processor of (3), wherein the image sensor includes an array of micro lenses, and the array of micro lenses, the array of polarizers, and the array of color mosaic filters are arranged in this order so that the array of micro lenses is closer to a light source than any of the other arrays is.

(16) The image capturing processor of (3), wherein the image sensor includes an array of micro lenses, and the array of color mosaic filters, the array of micro lenses, and the array of polarizers are arranged in this order so that the array of color mosaic filters is closer to a light source than any of the other arrays is.

(17) The image capturing processor of (3), wherein the image sensor includes an array of micro lenses, and the array of color mosaic filters, the array of polarizers and the array of micro lenses are arranged in this order so that the array of color mosaic filters is closer to a light source than any of the other arrays is.

(18) The image capturing processor of one of (15) to (17), wherein a pixel which is associated with a color filter in one color in the array of color mosaic filters has a subpixel structure, which is associated with multiple polarization filters that have mutually different polarization transmission axis directions.

(19) The image capturing processor of claim 2 or 3, wherein each polarizer in the array of polarizers is a wire grid polarizer including a plurality of metallic wires, of which the side surface is in contact with the air.

(20) The image capturing processor of one of (1) to (19), wherein the image capturing section is an endoscope.

(21) The image capturing processor of (20), wherein the image capturing section is housed in a container having a capsule shape.

(22) The image capturing processor of one of (1) to (21), wherein the image capturing section has a built-in light source which emits the illuminating light beam.

(23) An image processor to be used as the image processing section in the image capturing processor of one of (1) to (22), the image processor comprising: a light intensity image generator which generates a light intensity image based on the output of the image sensor; a polarization degree image generator which generates a polarization degree image by calculating the degree of polarization on a pixel-by-pixel basis based on the output of the image sensor; a retouching section which generates a retouched polarization image by enhancing the degree of polarization of the polarization degree image at depressions on a micro-geometric surface of the object and by correcting at least one of its hue, saturation and value; and an image synthesizing section which synthesizes the retouched polarization image and the light intensity image together.

(24) An endoscope to be used in the image capturing processor of one of (1) to (22), wherein the endoscope includes an image sensor that emits an illuminating light beam and that captures a polarization image of an object being illuminated with the illuminating light beam, and the endoscope is arranged so that the optical axis of the illuminating light beam and an image capturing optical axis are substantially coaxial with each other.

(25) An image processing method for performing image processing based on data about a polarization image that has been captured by an image sensor in a state where an object is illuminated with an illuminating light beam so that the optical axis of the illuminating light beam and an image capturing optical axis are substantially coaxial with each other, the method comprising the steps of: generating a light intensity image based on the output of the image sensor; generating a polarization degree image by calculating the degree of polarization on a pixel-by-pixel basis based on the output of the image sensor; generating a retouched polarization image by enhancing the degree of polarization of the polarization degree image at depressions on a micro-geometric surface of the object and by correcting at least one of its hue, saturation and value; and synthesizing the retouched polarization image and the light intensity image together.

(26) An image processing program for performing image processing based on data about a polarization image that has been captured by an image sensor in a state where an object is illuminated with an illuminating light beam so that the optical axis of the illuminating light beam and an image capturing optical axis are substantially coaxial with each other, the program being defined to make a computer perform the steps of: generating a light intensity image based on the output of the image sensor; generating a polarization degree image by calculating the degree of polarization on a pixel-by-pixel basis based on the output of the image sensor; generating a retouched polarization image by enhancing the degree of polarization of the polarization degree image at depressions on a micro-geometric surface of the object and by correcting at least one of its hue, saturation and value; and synthesizing the retouched polarization image and the light intensity image together.

According to conventional color light intensity image processing, it is difficult to detect a transparent or translucent micro-geometric structure. However, an image capturing processor according to an embodiment of the present disclosure can detect such a transparent or translucent micro-geometric structure on the surface of an organ, for example.

Figure 1B:
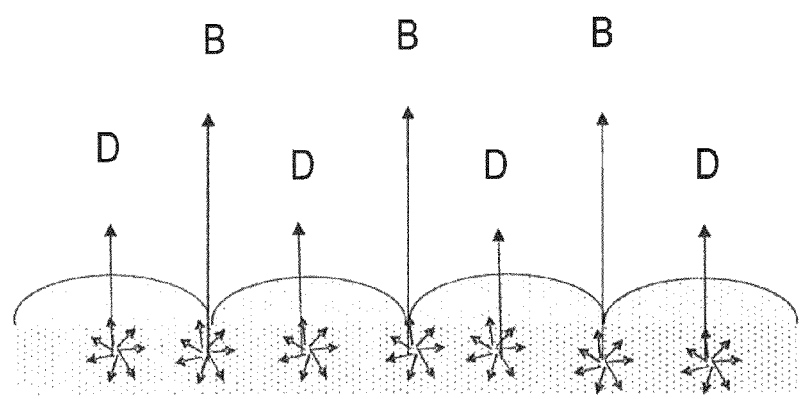
FIG. 1B schematically illustrates a light intensity distribution caused by internal diffuse reflection from the translucent micro-geometric structure.

First of all, it will be described with reference to FIGS. 1A and 1B why it is difficult to detect a transparent or translucent micro-geometric structure by the conventional light intensity image processing method. FIGS. 1A and 1B schematically illustrate a cross section of a micro-geometric structure on the surface of an organ such as a stomach or colon. In general, a structure with a huge number of grooves on the surface of a stomach or colon would be an iterative arrangement of structures, each having a semi-cylindrical upwardly projecting portion.

When observed through an endoscope, the object is illuminated with coaxial illumination. That is to say, the object is shot substantially straight on by irradiating the object with an illuminating light beam that has been emitted from a light source which is located substantially right in front of the object. In other words, in such coaxial illumination, the axis of traveling light that has been emitted from a light source (i.e., the optical axis of the illuminating light beam) and the optical axis of a camera (i.e., the image capturing optical axis) are substantially coaxial with each other (i.e., the angle formed between those two optical axes is 15 degrees or less). In the case of such coaxial illumination, there are roughly two types of reflected light beams to be observed by normal color light intensity shooting. One of the two types is specular reflected light which is reflected from the surface as shown in FIG. 1A. The other type is internally diffused light which penetrates through the medium, gets reflected from a deeper layer, and then returns toward the source through the surface.

The specular reflected light is produced only when the direction of the irradiating light and the image capturing optical axis almost satisfy the condition of regular reflection, and therefore, is produced only locally when a scene is shot through an endoscope. The color of the specular reflected light is the color of the illumination, i.e., the color white, and has very high intensity. According to the regular reflection condition described above, the specular reflected light is intense and bright at convexes of the micro-geometry but is weak and dark at its concaves.

On the other hand, the internally diffused light is observed all over the scene shot. The color of the internally diffused light is the color of the medium itself, and its intensity is not so high. When irradiated with the internally reflected light, the entire medium tends to shine, projections that are thick portions of the medium tend to look dark, and concaves that are thin portions of the medium tend to look bright.

As can be seen from the foregoing description, in the light intensity image representing such a micro-geometric surface of an organ, the specular reflected light and the internally diffused light will behave in mutually opposite ways.

In each scene shot, those two types of reflected light beams are superposed one upon the other with their light quantities changed. That is why in a region where the difference in light intensity between those two types of light beams reflected from concaves is almost equal to the difference in light intensity between those two types of light beams reflected from convexes, there is substantially no difference in light intensity level between the concaves and convexes. As a result, the light intensity image becomes useless to detect the micro-geometric texture. Or even if there is some difference in light intensity level between the depressions and projections but if processing was carried out by reference to that information so that a pixel with a lower light intensity than surrounding pixels is detected as a concave, then the relative positions of those regions with relatively intense specular reflected light and those regions with relatively intense internally reflected light would be different from the relative positions of the concaves and convexes.

Next, it will be described how to observe the micro-geometric surface with polarized light. When an object is going to be shot through an endoscope using coaxial illumination, there are roughly two types of reflected light beams to be observed by reference to polarization information. One of the two types is a polarized light beam to be produced by getting incoming light reflected twice from the slopes of a depression on the micro-geometric surface (which will be referred to herein as a "twice reflected polarized light beam"). The other type is a polarized light beam to be produced while the incoming light penetrates through the medium, gets reflected from a deeper layer, and then returns toward the source through the surface (which will be referred to herein as "internally diffusing polarized light beam").

The intensity of a polarized light beam is expressed as the degree of polarization. According to the Fresnel theory, the degree of polarization is determined by the refractive index, the angle of incidence and the angle of emittance of the medium. A light beam that has been reflected only once from the surface is hardly polarized.

Figure 2A:
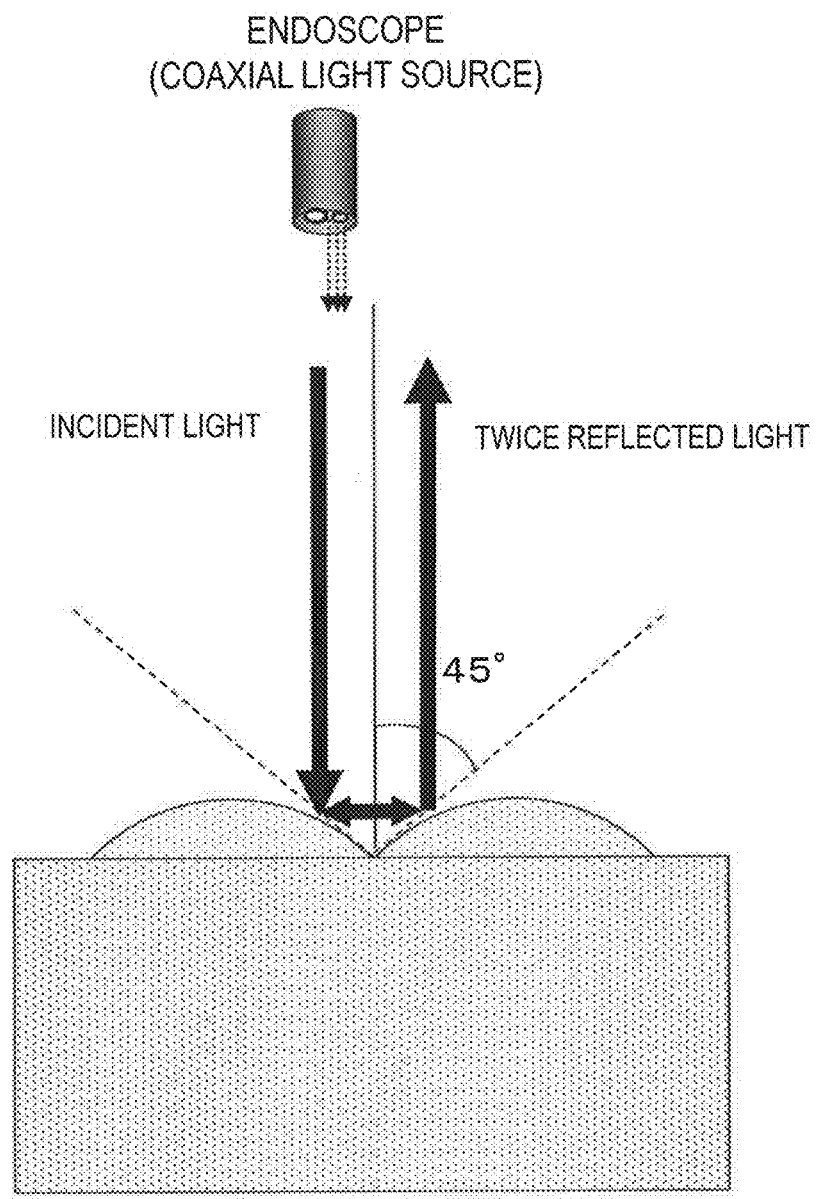
FIG. 2A illustrates polarized light produced by getting incoming light reflected twice from a translucent micro-geometric portion.

FIG. 2A illustrates how an incoming light beam is reflected twice from a depression of a micro-geometric structure. Actually, around the bottom of a depression, which is a modeled groove located on the surface of an organism between two semi-cylindrical projections, the angles defined by normals with respect to the slopes are not constant but have some distribution. In this example, however, the largest angle of the bottom is supposed to be approximately 45 degrees for the sake of simplicity. In that case, the incoming light beam is reflected twice from the slopes to reach a viewpoint of shooting. When the light beam is reflected twice between the air and the surface medium, the light beam gets polarized very intensely.

Figure 2B:
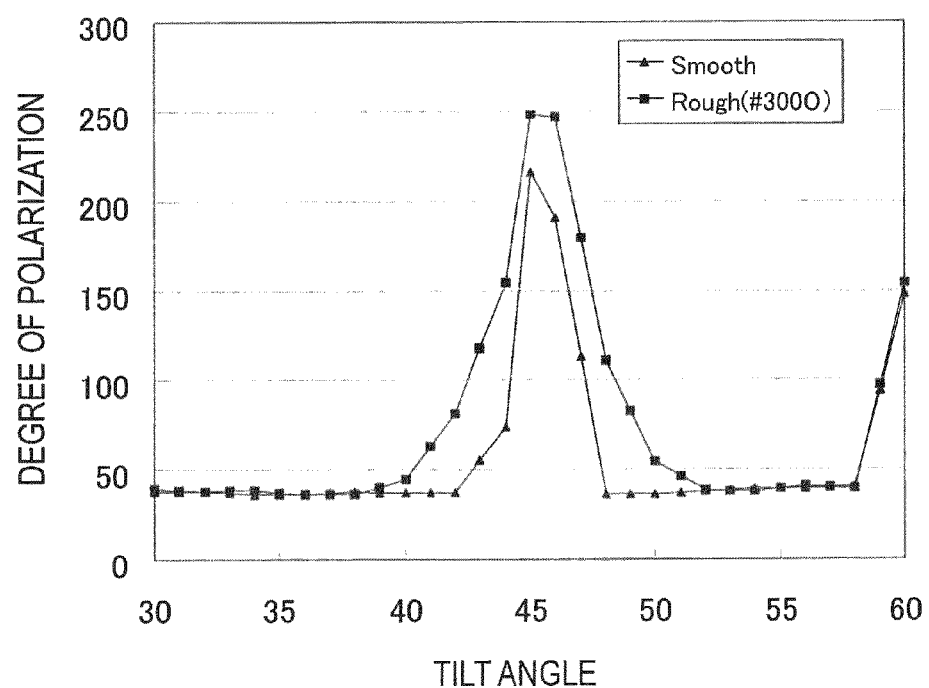
FIG. 2B is a graph showing how the degree of polarization of the light beam that has been reflected twice from a translucent micro-geometric portion changes with the tilt angle of the slopes of a depressed portion.

FIG. 2B is a graph showing how the degree of polarization of the light beam that has been reflected twice and then observed under coaxial illumination changes with the tilt angle of the slopes. As can be seen from FIG. 2B, when the tilt angle of the slopes of the depression is 45 degrees, the degree of polarization of the twice reflected light is very high. But as the tilt angle deviates from 45 degrees, the degree of polarization decreases steeply. That is why if the entire surface is covered with such a micro-geometric texture, the twice reflected polarized light beams are intense enough to be detected easily. However, such twice reflected light beams are produced in only local regions which satisfy a predetermined angular relation. In addition, if the angle formed between those two slopes is too small, then the phenomenon itself never happens. For that reason, even though it is effective to detect a depression of a surface topography using such a twice reflected polarized light beam when an artificial industrial product needs to be tested, for example, such a detecting method provides a very limited amount of information when an organism in an indefinite shape is observed from an arbitrary position through an endoscope.

Figure 3A:
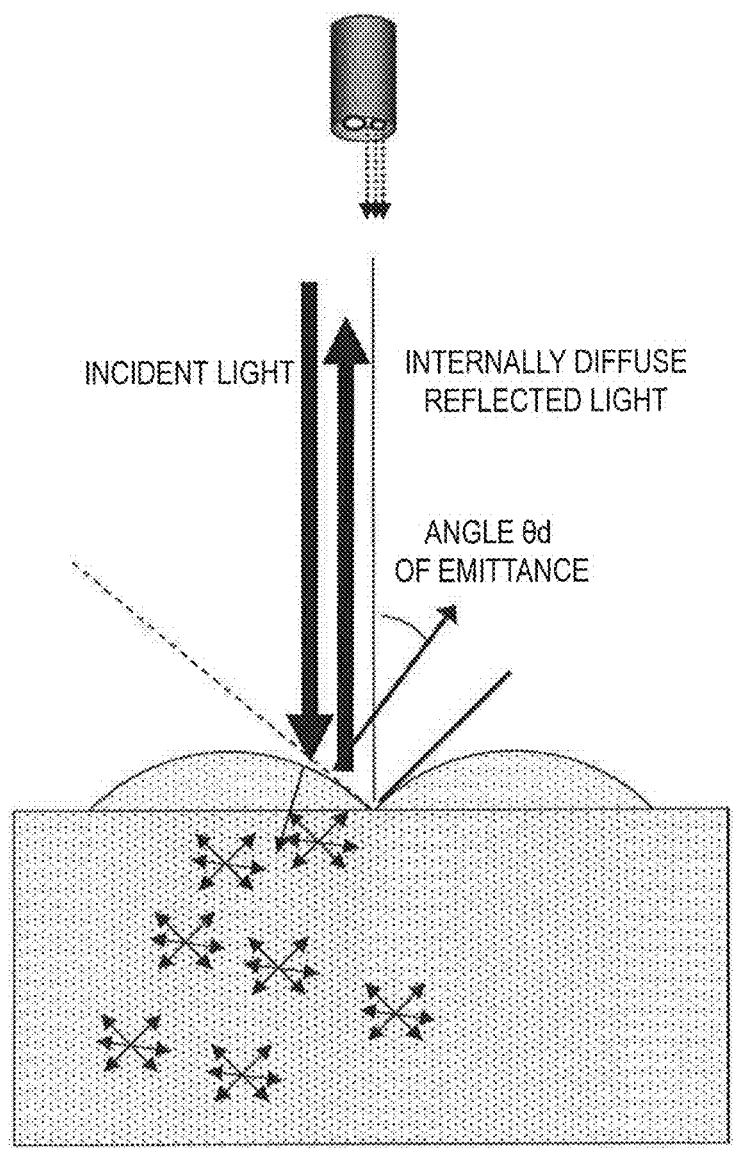
FIG. 3A illustrates polarized light produced by getting incoming light internally diffuse-reflected from a translucent micro-geometric portion.
Figure 3B:
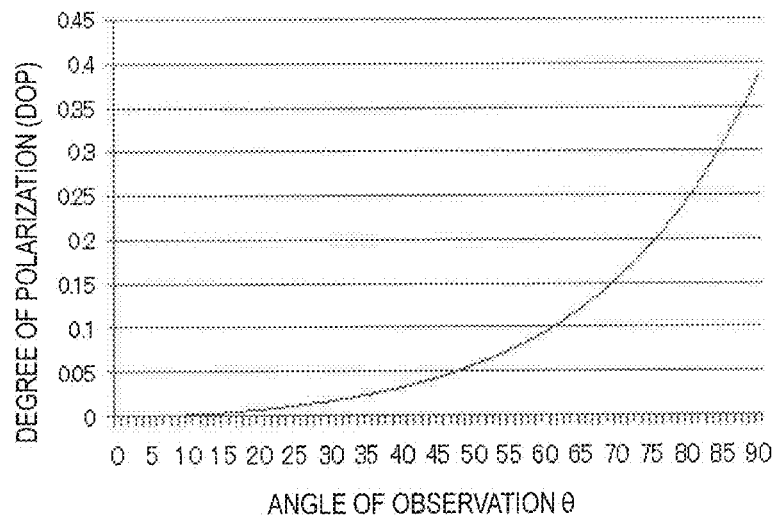
FIG. 3B is a graph showing how the degree of polarization of the light beam that has been internally diffuse-reflected from a translucent micro-geometric portion changes with the angle of observation.

FIG. 3A illustrates how incoming light is internally diffuse-reflected by a medium with surface topography. After having entered a translucent medium, the incoming light will soon reach a deeper mucosa interface while getting scattered in various manners inside the medium. Then, the incoming light gets reflected from the interface and then emerges through the surface again. If the refractive index in the medium is uniform, the internally diffused light will have no particular polarization. However, if the angle of emittance which is the tilt angle defined by the line of sight with respect to a normal to the interface is large, the degree of polarization of the internally reflected light to be observed under coaxial illumination increases. FIG. 3B is a graph showing how the degree of polarization (DOP) of the internally diffused light changes with the angle of emittance (or the angle of observation θ). As shown in FIG. 3B, the closer to the occlusion edge, the larger the degree of polarization of the internally reflected light to be observed under the coaxial illumination. That is why as in this model, when the maximum tilt angle is 45 degrees, the degree of polarization decreases. However, such weak polarized light can be detected sufficiently using a high performance polarization image sensor.

The twice reflected polarized light and the internally diffuse-reflected polarized light can be distinguished from each other by determining not only whether the polarized light is a locally limited one or a global one and whether the degree of polarization is large or small as described above but also whether the plane of oscillation of the polarized light becomes parallel or perpendicular to the orientation of the surface topography.

That is why if the intensity of the twice reflected light was too high, then the internally diffuse-reflected light that is perpendicular to the twice reflected light would become too faint to be observed. The present inventors discovered and confirmed via experiments that if a translucent substance to be an object is a relatively dark substance (i.e., a black or brown object that will make the diffuse reflectance of the light low), the twice reflection from the surface will be too intense to observe the internally diffuse-reflected polarized light that is perpendicular to the twice reflected light easily. In that case, however, as some variation in light intensity (i.e., a bright and dark pattern) is observed due to the micro-geometric texture of the surface as described above, there is no need to count on the polarized light observation anymore. On the other hand, in the case of a bright translucent substance such as the mucosa of a digestive organ (i.e., an object in the color white, yellow or pink with a high light diffuse reflectance), there is so much internally diffuse-reflected light that it is difficult to sense the bright and dark pattern of the light intensity and that the polarized light components produced by internal diffusion become principal components. There is such a complementary relation between the dark and bright objects.

It should be noted that when the internally diffused polarized light is observed, the polarized light detection performance of the image capturing system becomes important. As an index to evaluating the performance of a polarization image sensor, an extinction ratio is used. The present inventors carried out an experiment using a translucent lenticular plate (to be described below) as a replacement for a real digestive organ mucosa. As a result, the present inventors discovered that when a polarization imaging camera with an extinction ratio of approximately 6:1 was used, it was difficult to observe the surface topography. On the other hand, when an image capturing system including a polarizer with an ratio of approximately 166:1 and a color camera in combination was used, the surface topography could be observed sufficiently. A polarization image sensor for use in embodiments of the present disclosure achieves an extinction ratio of 100:1 or more in a wavelength range in which polarization image capturing is carried out.

Figure 4:
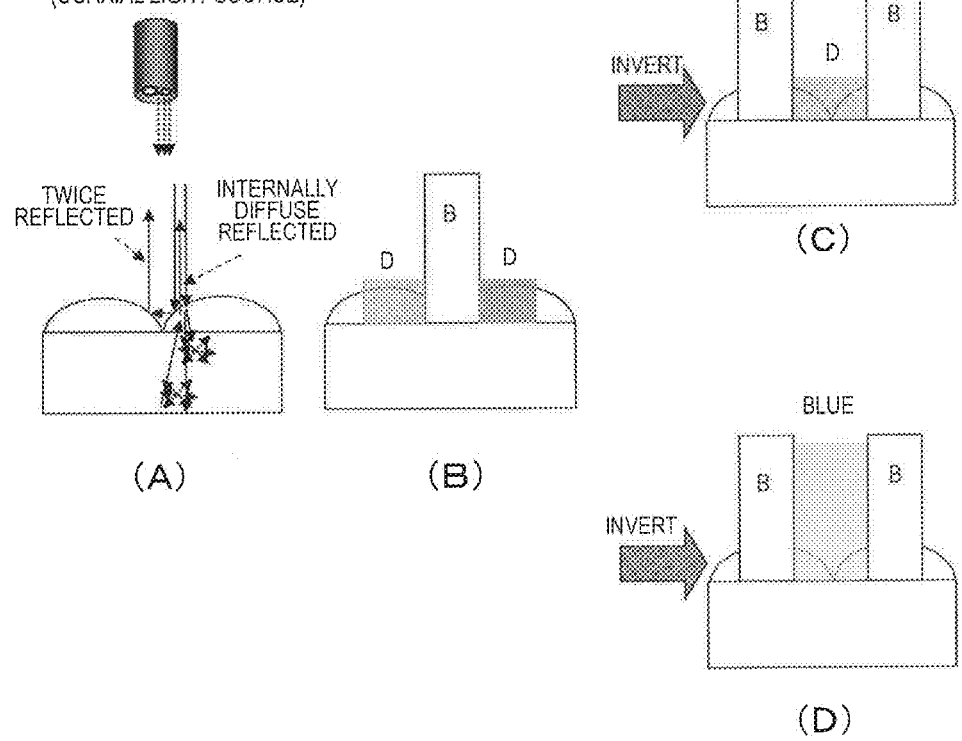
FIG. 4 illustrates how to retouch a polarization image by enhancing the degree of polarization of a translucent micro-geometric portion.

Next, it will be described with reference to FIG. 4 how a depressed groove that has been actually detected may be presented to a doctor in an easily recognizable way. Portion (A) of FIG. 4 illustrates the two types of polarized light beams to be detected from the micro-geometric surface. In each of these two types of polarized light beams, its degree of polarization reaches a local maximum and a local minimum at a concave and at a convex, respectively. That is why when generated based on these two types of polarized light beams, the polarization degree images will be bright at convcaves where the degree of polarizations are high but will be dark at convexes as shown in portion (B) of FIG. 4. Currently, however, when the doctor actually sprinkles a blue pigment onto the micro-geometric surface while looking through an endoscope, the concaves will be filled with the blue liquid and look dark, while the convexes will repel the blue liquid and look bright. For that reason, even if such a polarization degree image is superposed as it is on a light intensity image, the concaves and convexes will not be easily recognizable for the doctor.

Thus, to overcome such a problem, the polarization degree image is retouched according to an embodiment. Specifically, as shown in portion (C) of FIG. 4, the polarization degree image has its value inverted and then subjected, along with the light intensity image, to a weighting addition. As a result, a bright and dark pattern of light intensities can be superposed on the seemingly textureless surface of a color image obtained by an endoscope so that the concaves will look dark and the convexes will look bright. To make the resultant image even closer to a pigment sprinkled image, the processing of modulating the saturation with the value by increasing the value with the hue of the polarization degree image set to be the color blue may be carried out as shown in portion (D) of FIG. 4. By performing such processing, the image generated will look as if those depressions were filled with the blue liquid.

An embodiment of the present disclosure uses a property of composite light obtained by synthesizing together the two types of reflected light beams that the composite light will have a local maximum intensity just at depressions of the micro-geometric surface. As described above, the two types of reflected light beams are (i) the reflected light beam that has been produced just locally but with a high degree of polarization by getting incoming light (specular) reflected twice by a transparent or translucent surface of the object and (ii) the reflected light beam that has been produced globally with a low degree of polarization when the internally diffused light emerges through the transparent or translucent surface of the object. That is why there is no need any longer to use the light intensities themselves directly. And even in a region where there is almost no variation in brightness or even if the relation between the brightness and the surface topography changes according to the reflection state, the micro-geometric surface of the object can still be detected.

Furthermore, if the polarization degree image is retouched in terms of at least one of the hue, light intensity and value of its color signal and if the retouched polarization degree image and the light intensity image are synthesized together, an image enhancing the micro-geometry of the object's surface can be obtained. By adopting such a technique, even an image with a low degree of polarization can also be superposed on a light intensity image so that the micro-geometric surface texture detected is easily sensible for a human viewer. Specifically, a processor according to this embodiment has a mode in which the light intensities are displayed so that the concaves of the micro-geometric surface will look dark and the convexes will look bright and a mode in which the light intensities are displayed so that the concaves of the micro-geometric surface will look blue and the convexes will look white as if a blue pigment liquid such as indigo carmine were sprinkled.

Hereinafter, embodiments of the present disclosure will be described in further detail. The four embodiments to be described below can be outlined as follows. It should be noted, however, that the present disclosure is in no way limited to these specific embodiments.

Embodiment 1

The illuminating light is non-polarized R, G and B light, and the object is irradiated time-sequentially with light beams in different colors. The image sensor includes an array of polarizers but does not have any color mosaic filters.

Embodiment 2

The illuminating light is non-polarized white light. The image sensor includes both an array of polarizers and color mosaic filters.

Embodiment 3

The illuminating light is polarized white light, and the object is irradiated time-sequentially with polarized light beams with different polarization plane directions. Polarized illuminating light is produced at the end of an endoscope where no light source is provided. The image sensor includes color mosaic filters but does not have any array of polarizers.

Embodiment 4

The illuminating light is polarized white light, and the object is irradiated time-sequentially with polarized light beams with different polarization plane directions. A light source is arranged at the end of an endoscope. The image sensor includes color mosaic filters but does not have any array of polarizers.

Embodiment 1

Figure 5:
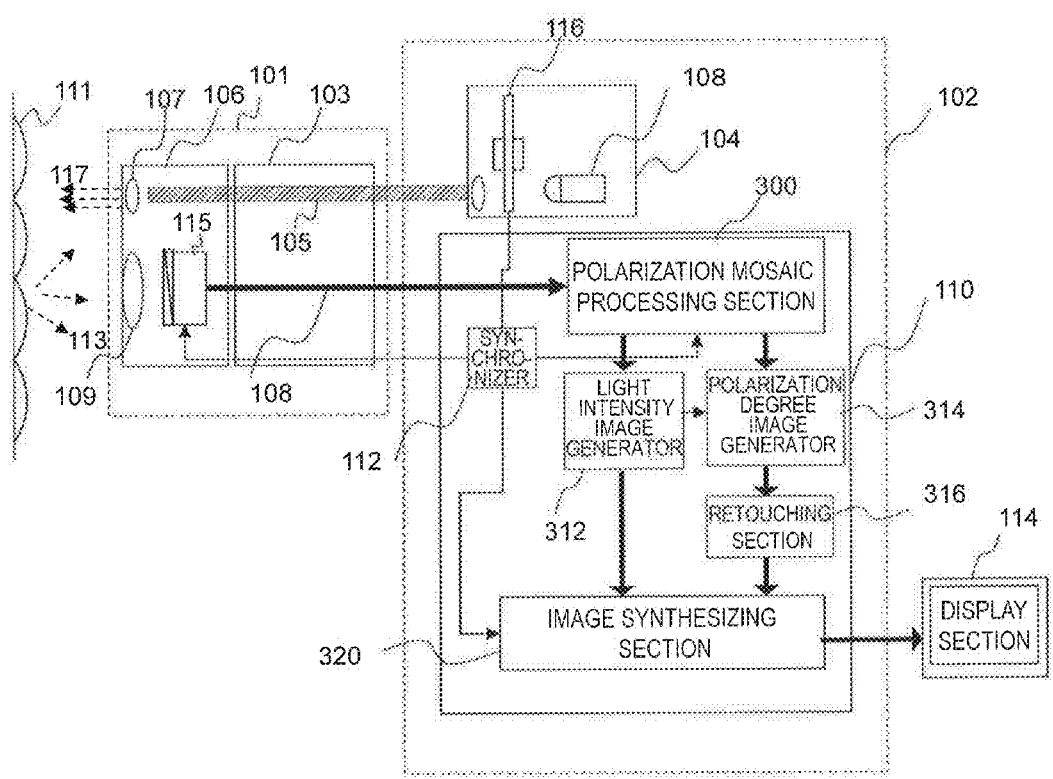
FIG. 5 illustrates a first embodiment of the present disclosure.

FIG. 5 schematically illustrates an overall configuration for an image capturing processor as a first embodiment of the present disclosure. This image capturing processor includes an endoscope 101, a controller 102 and a display section 114. The endoscope 101 includes a tip portion 106 with a monochrome broadband polarization image sensor 115 and an inserting portion 103 with a light guide 105 and a video signal line 108. The inserting portion 103 of the endoscope 101 has a structure that is elongated horizontally as shown in FIG. 5 and that can be bent flexibly. Even when bent, the light guide 105 can also propagate light.

The controller 102 includes a light source section 104 and an image processor 110. A lamp 108 such as a xenon lamp, a halogen lamp or an LED lamp is built in the light source section 104. The non-polarized white light emitted from the lamp 108 passes through a color wheel 116 with rotating RGB filters. As a result, red (R), green (G) and blue (B) frame sequential light beams are produced and then guided to the tip portion 106 through the light guide 105. In this manner, a translucent object 111 with a micro-geometric surface is irradiated with non-polarized illuminating light beams 117, of which the colors change sequentially from one of RGB into another. The light 113 reflected from the object 111 is imaged onto the monochrome broadband polarization image sensor 115 through a shooting lens 109.

Synchronously with the rotation of the color wheel 116, a synchronizer 112 sends a shooting start signal to the monochrome broadband polarization image sensor 115, thereby getting video based on the reflected light. The video signal thus obtained by capturing the image reaches an image processor 110 through the video signal line 108.

By performing these series of processing by the frame sequential method in which the colors are changed from one of RGB into another, a color image and a polarization image are captured.

Next, it will be described what configuration the monochrome broadband polarization image sensor 115 may have and how the processing that has been described with reference to FIG. 4 gets done through the characteristic processing by the image processor 110.

Figure 6:
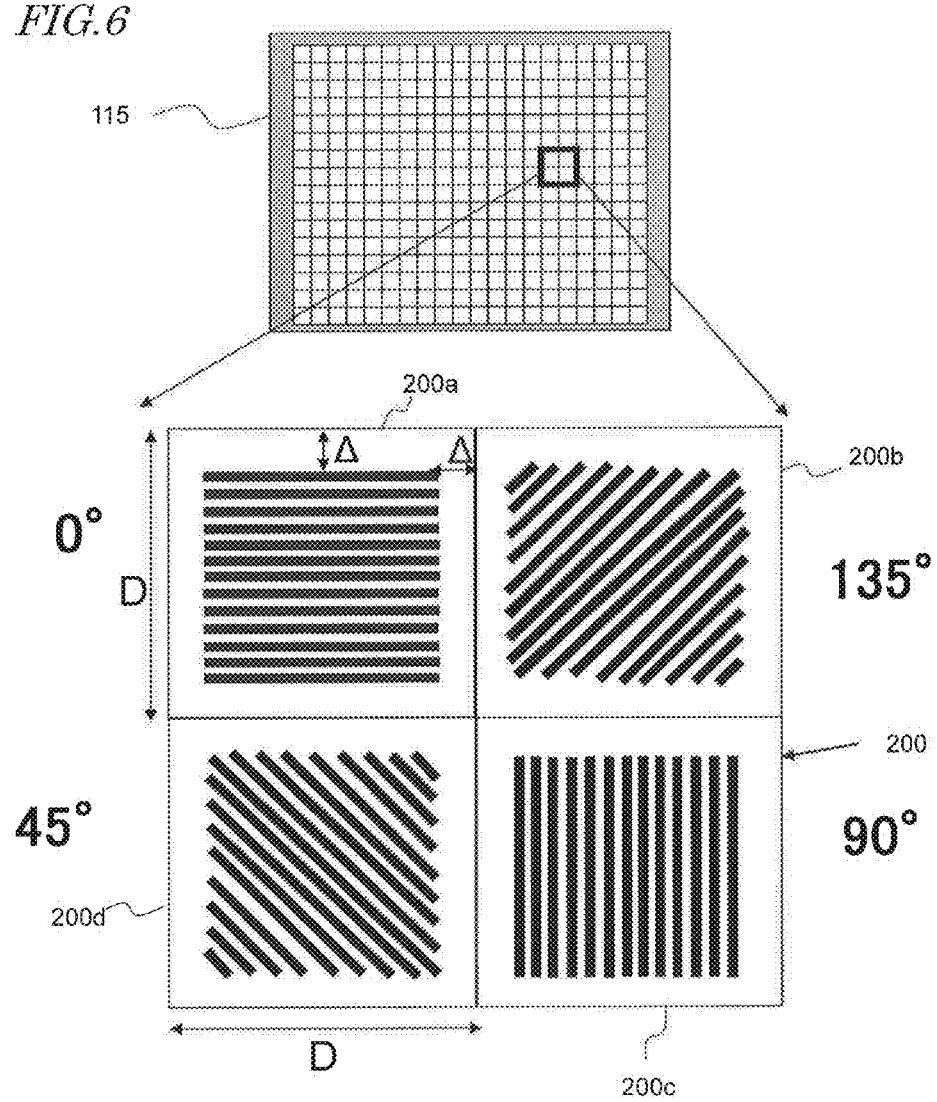
FIG. 6 illustrates the planar structure of wire grid polarizers for a monochrome broadband polarization image sensor according to the first embodiment.

FIG. 6 illustrates an exemplary configuration for the image capturing plane of the monochrome broadband polarization image sensor 115. As shown in FIG. 6, pixels are arranged regularly in columns and rows on the image capturing plane.

In this embodiment, to change the colors of the illuminating light sequentially from one of RGB into another, no color mosaic filters are arranged on the image capturing plane. That is why the image sensor 115 of this embodiment is a monochrome image sensor but is configured to have sensitivity in each of the R, G and B wavelength ranges. In addition, the polarizers also have sufficient performance in the visible radiation range so that a polarization image can be captured in this broad wavelength range. For example, in the wavelength range of 400 nm to 800 nm, the polarizers may have an extinction ratio of 100:1 or more. In this embodiment, instead of using polarizers which have polarization properties only in a narrow range of particular wavelengths, an array 200 of metallic wire grid polarizers is adopted.

An exemplary specific arrangement for the array 200 of metallic wire grid polarizers is illustrated on a larger scale in FIG. 6. In this example, four arrays 200a, 200b, 200c and 200d of metallic wire grid polarizers are arranged in 2×2 pixel blocks with their polarization transmission axes rotated so that the polarization transmission axes of any two adjacent arrays define an angle of 45 degrees between them. Each block comprised of these 2×2 arrays 200a, 200b, 200c and 200d of metallic wire grid polarizers defines a single unit of the periodic structure. In this description, a wire grid in which metallic wires are arranged parallel to each other in a certain direction will be referred to herein as a single "metallic wire grid polarizer", and a structure in which a plurality of such metallic wire grid polarizers are arranged in a plane will be referred to herein as a whole as an "array of metallic wire grid polarizers".

As will be described later, this array 200 of metallic wire grid polarizers may be arranged at an arbitrary level between the top and bottom of the image sensor. When viewed perpendicularly to the image capturing plane, these arrays 200a, 200b, 200c and 200d of metallic wire grid polarizers allocated to respective pixels are arranged in respective inner parts of their areas with some margin Δ left with respect to the outer periphery of the pixels. If a single pixel is a square, of which each side has a length D of 3 to 4 μm, the margin Δ may be set to be equal to or greater than 0.2 μm (=200 nm), for example.

A tradeoff is inevitable between the transmittance, the extinction ratio and the duty ratio of the width L of each of multiple metallic wires that form those arrays 200a, 200b, 200c and 200d of wire grid polarizers to their spacing S. In this embodiment, the width L and spacing S are set to satisfy L=S=0.1 μm=100 nm as will be described later. If Δ=0.2 μm=200 μm is satisfied, the number of metallic wires that form each of these arrays 200a, 200b, 200c and 200d of wire grid polarizers changes with the direction in which those metallic wires run. Specifically, if the directions in which the metallic wires run are 0 and 90 degrees, the number of the metallic wires is 17. On the other hand, if the directions in which the metallic wires run are 45 and 135 degrees, the number of the metallic wires is 23. That is to say, there are an odd number of metallic wires in each of these two situations. That is why when viewed perpendicularly to the image capturing plane, the center of each pixel is always covered with any of the arrays 200a, 200b, 200c and 200c of wire grid polarizers. Also, in each of these arrays 200a, 200b, 200c and 200c of wire grid polarizers, wires located on both sides of a central wire are arranged axially symmetrically with respect to that central wire.

Figure 7:
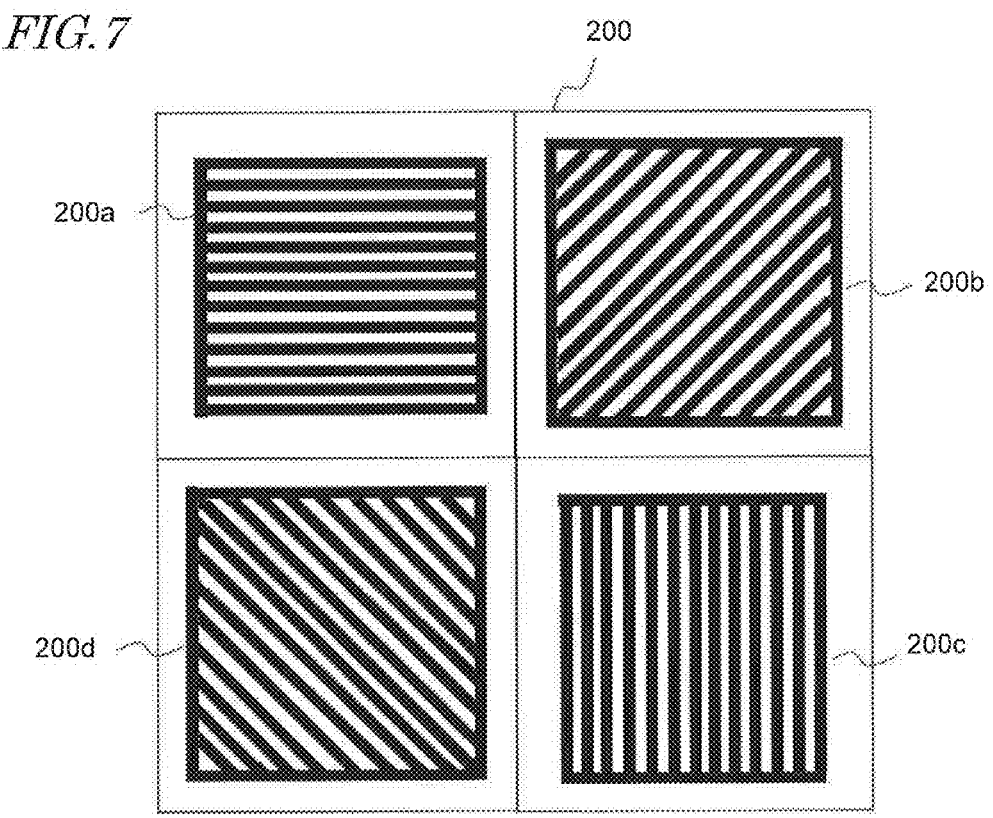
FIG. 7 illustrates the planar structure of framed wire grid polarizers for a monochrome broadband polarization image sensor according to the first embodiment.
Figure 8:
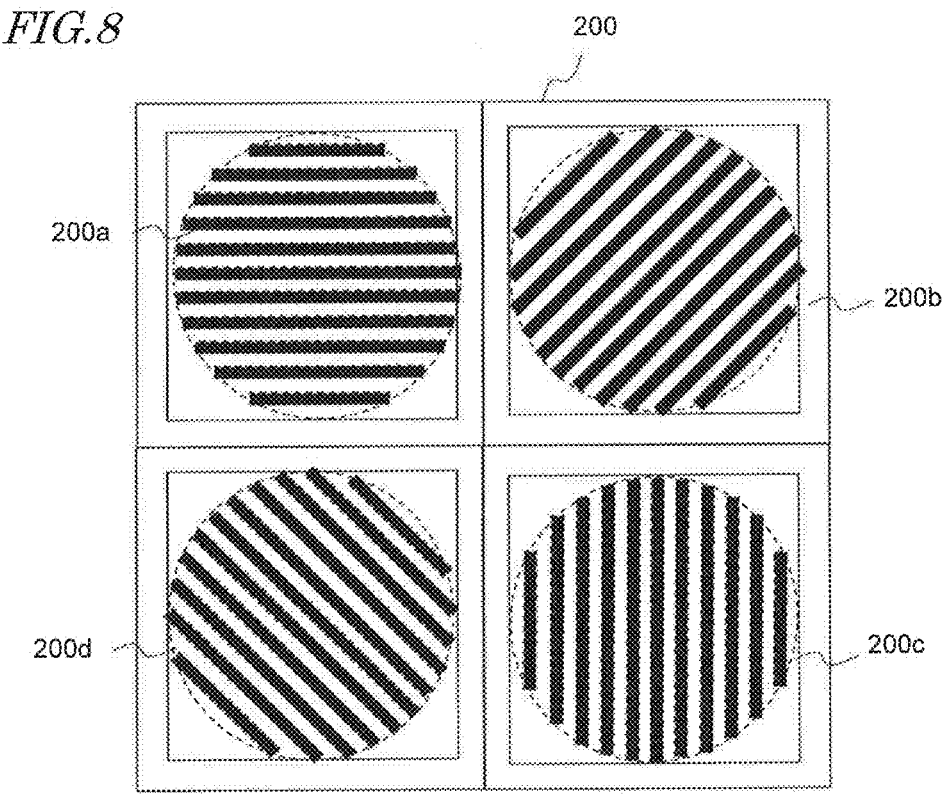
FIG. 8 illustrates the planar structure of circular wire grid polarizers for a monochrome broadband polarization image sensor according to the first embodiment.

FIGS. 7 and 8 illustrate other exemplary arrangements of the set of arrays 200a, 200b, 200c and 200d of polarizers in the array 200 of wire grid polarizers. In each of these two examples, 2×2 (i.e., four) arrays 200a, 200b, 200c and 200d of wire grid polarizers form a single unit of a periodic structure and the directions in which the metallic wires run in these arrays 200a, 200b, 200c and 200d of wire grid polarizers are rotated so that the direction in which the metallic wires run in one of these four arrays defines an angle of 45 degrees with respect to the direction in which the metallic wires run in an adjacent one of the arrays.

In the example illustrated in FIG. 7, each array 200a, 200b, 200c, 200d of wire gird polarizers is surrounded with a metallic frame, thereby preventing the respective wires that form the wire grid polarizers from falling down even if those wires are tall ones.

On the other hand, in the example illustrated in FIG. 8, the number of metallic wires that form each of the arrays 200a, 200b, 200c, and 200d of wire grid polarizers is constant, no matter in what direction the metallic wires run.

These arrays 200a, 200b, 200c, and 200d of metallic wire grid polarizers may be made of aluminum (Al) which is also used in general wire grid polarizers, but may also be made of any other metal. The sizes of the metallic wires that form these arrays 200a, 200b, 200c, and 200d of wire grid polarizers fall within a sub-wavelength range to operate these arrays with visible radiation. In the following description, the width of the metallic wires and the spacing between them when the array 200 of metallic wire grid polarizers is viewed straight on will be referred to herein as their "line width" and "space width", respectively. Also, the thickness of the metallic wires when the array 200 of metallic wire grid polarizers is viewed sideways will be referred to herein as their "height". The line width, space width and height may all be set to be equal to or smaller than approximately 100 nm.

The following Table 1 summarizes how the performance of such a wire grid polarizer of aluminum changes with its sizes:

TABLE 1

| Pitch P | Height H | TM transmittance | Extinction ratio |
|---|---|---|---|
| 120 nm (L60/S60) | 130 nm | 80% | 100:1 or more |
| 160 nm (L80/S80) | 130 nm | 80% | 100 to 1000:1 |
| 200 nm (L100/S100) | 120 nm | 70-80% | 100:1 or more |

The numerical values shown in this Table 1 were obtained as a result of simulations experiments that were carried out by the present inventors. It can be seen that supposing the line width L and space width S of the wire grid polarizer are equal to each other, an extinction ratio of 100:1 or more can be obtained by setting the pitch P (=(L+S)) and the height H to be the values shown in this Table 1.

Figure 9:
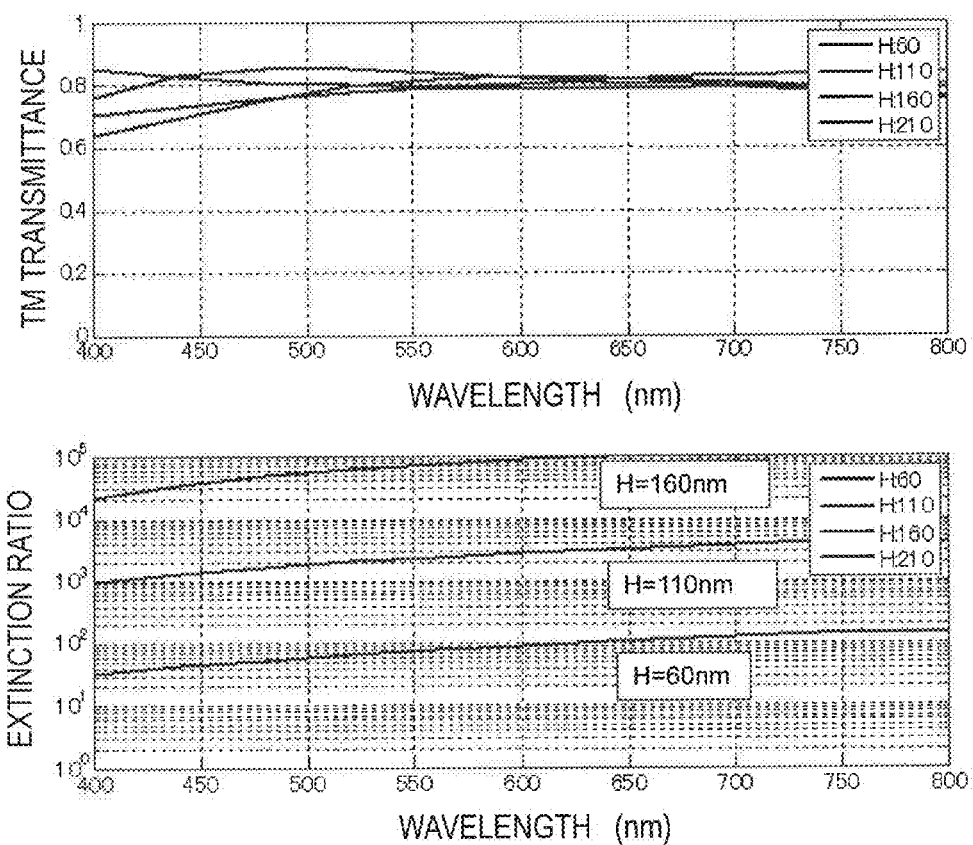
FIG. 9 shows the wavelength dependences (based on the results of simulations) of the TM transmittance and extinction ratio of wire grid polarizers (where P=120 nm).
Figure 10:
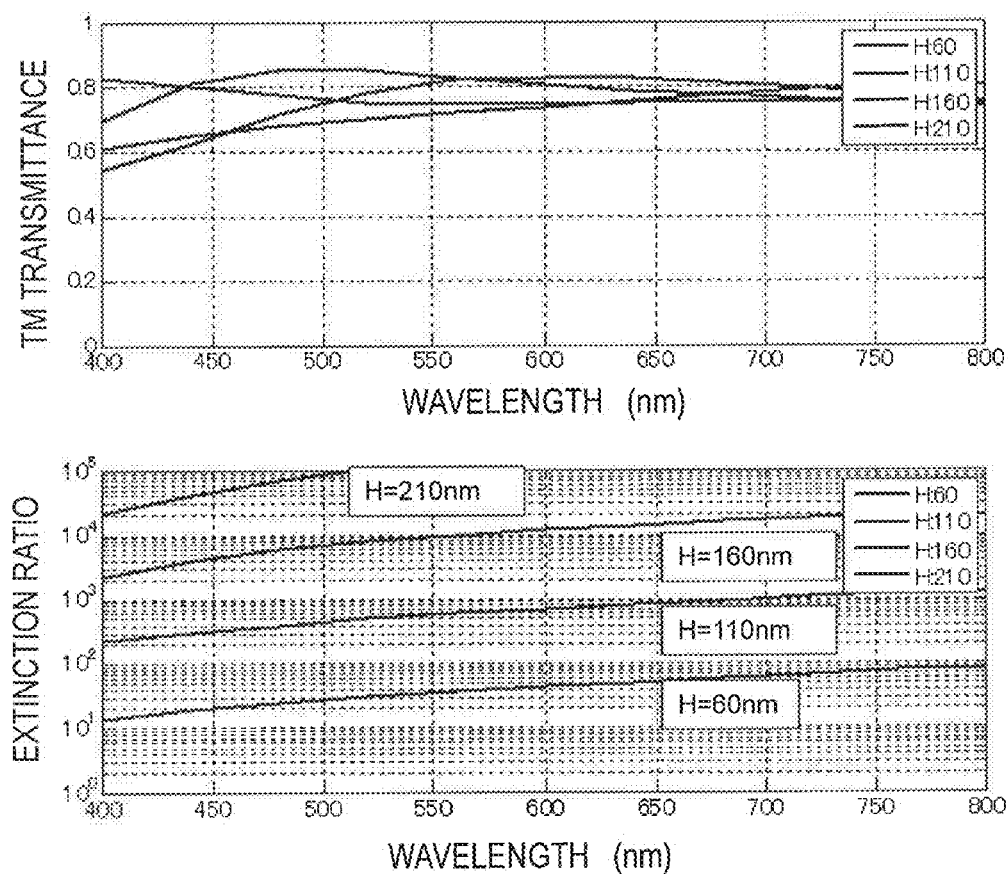
FIG. 10 shows the wavelength dependences (based on the results of simulations) of the TM transmittance and extinction ratio of wire grid polarizers (where P=160 nm).
Figure 11:
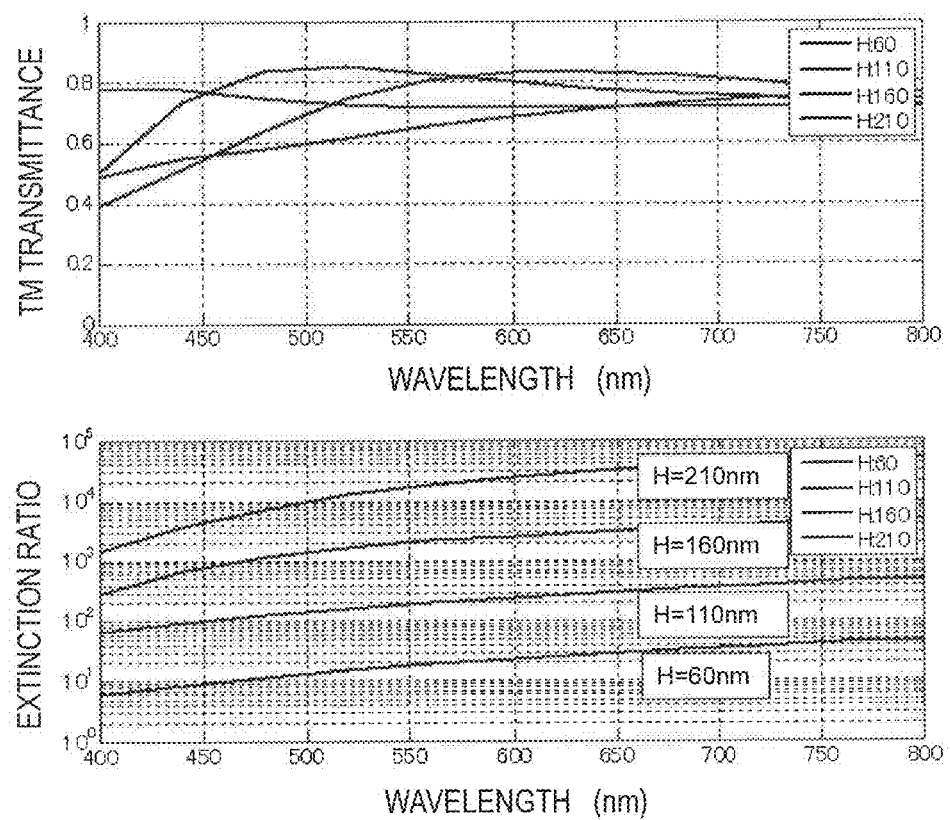
FIG. 11 shows the wavelength dependences (based on the results of simulations) of the TM transmittance and extinction ratio of wire grid polarizers (where P=200 nm).

FIGS. 9 to 11 shows the results of simulations indicating the wavelength dependences of the TM transmittance and extinction ratio of the wire grid polarizer in three situations where P=120, 160 and 200 nm, respectively. When the pitch P was 120 nm, the highest performance was achieved. However, it turned out that even when P was 200 nm, an extinction ratio of 100:1 could be achieved in almost the entire visible radiation wavelength range by setting H to be 110 nm or more.

Next, the oblique incidence characteristic of a wire grid polarizer will be described.

Figure 12:
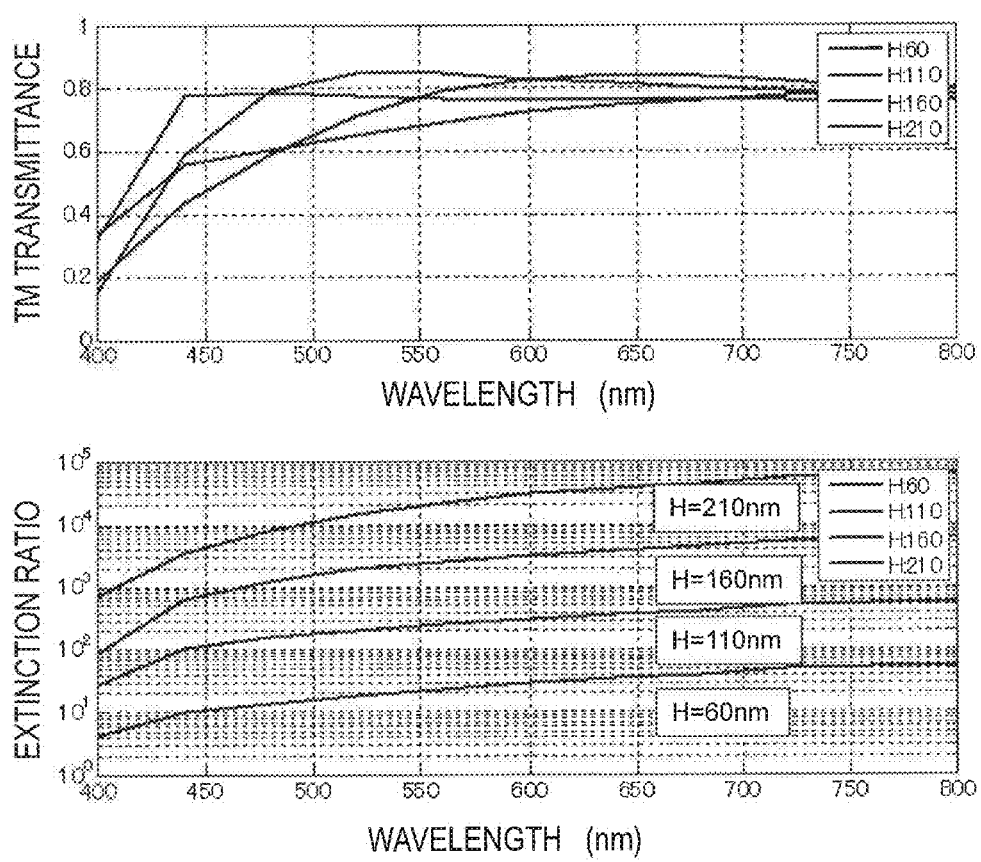
FIG. 12 shows the wavelength dependences (based on the results of simulations) of the TM transmittance and extinction ratio of wire grid polarizers (where P=200 nm) when the angle of incidence of incoming light is 30 degrees.

FIG. 12 shows the results of simulations that were obtained in a situation where parallel light was incident at an angle of incidence of 30 degrees onto a wire grid polarizer which satisfied P=200 nm. Comparing the results shown in FIG. 12 to the ones shown in FIG. 11, it can be seen that both the TM transmittance and extinction ratio decreased at a waveform of around 400 nm. However, this decrease was relatively small when P was sufficiently small. If light was incident perpendicularly onto a wire grid polarizer, such a decrease would not be seen.

Next, it will be described what influence the background medium of the wire grid polarizer will have.

FIG. 13 illustrates graphs showing the wavelength dependences of the extinction ratio in a situation where the refractive index n of the background medium was set to be 1.46 (when the medium was made of $SiO_2$, for example) and in a situation where the refractive index n of the background medium was set to be 1.0 (i.e., when the medium was the air). The graphs shown in FIG. 13 show the results of simulations when P=120 nm, when P=160 nm, and when P=200 nm, respectively. In FIG. 13, the curves that say "All in the air" represent examples in which the wires were surrounded with the air, while the curves that say "All in the medium" represent examples in which the wires were surrounded with the background medium. In this case, attention should be paid to the fact that the difference in extinction ratio between these two situations was as much as one digit. That is to say, the wire grid polarizer can achieve a higher extinction ratio when put in the air rather than when buried in a medium with a high refractive index. This is probably because as the wavelength of incoming light decreases to 1/n in a medium, a metallic structure arranged in the medium will look relatively large for the wavelength and can no longer satisfy the condition to operate as a sub-wavelength element.

According to the aforementioned article of "CCD Polarization Imaging Sensor with Aluminum Nanowire Optical Filters", when P=140 nm and H=70 nm, the extinction ratio at G and R wavelengths was 44:1 and the extinction ratio at B wavelength was 30:1. Compared to the results of simulations that were carried out on a wire grid polarizer by itself, these numerical values decreased by more than one digit. That is why if a wire grid polarizer is actually attached to an image sensor, its performance would deteriorate. A major cause of such performance deterioration is a crosstalk between pixels. That is why according to this embodiment, first of all, the basic performance of the wire grid polarizer is improved and the distance from the wire grid polarizer to the photodiode (PD) of the image sensor is set to be approximately 2 to 3 μm.

Figure 14:
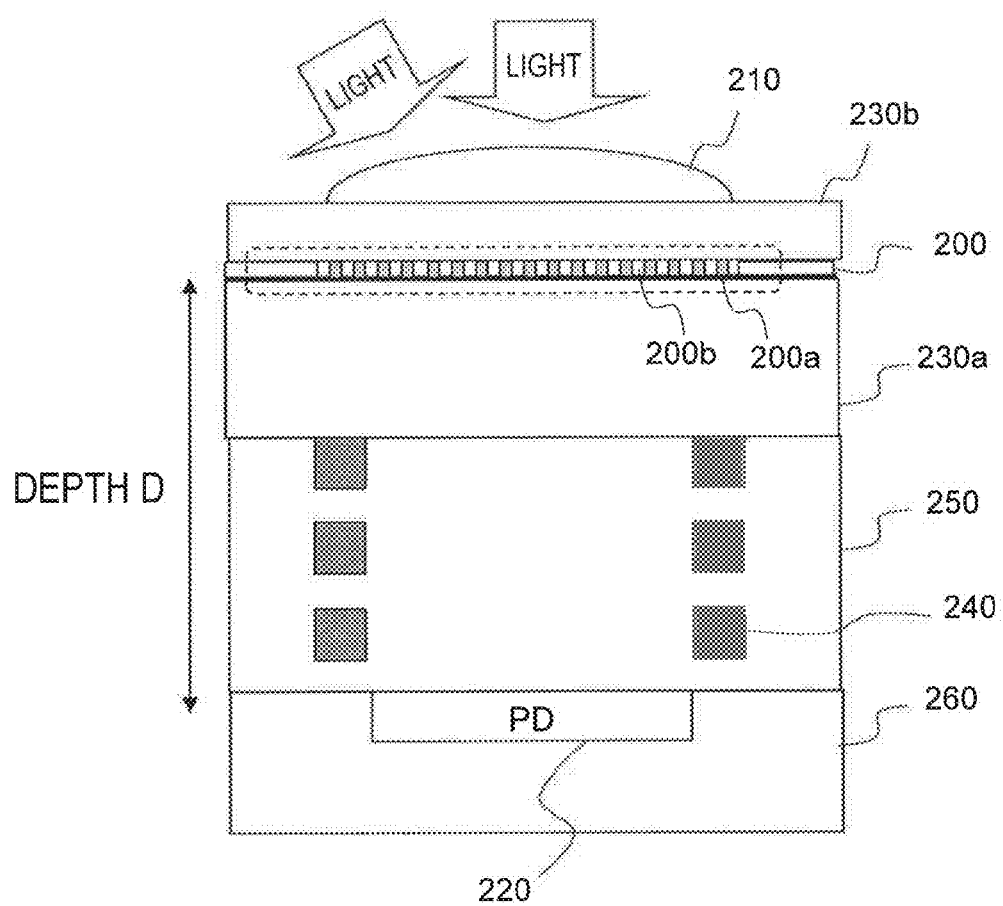
FIG. 14 illustrates a cross-sectional structure of a wire grid polarizer of a monochrome broadband polarization image sensor according to the first embodiment (in which the micro lens is arranged at the top).

FIG. 14 illustrates a cross-sectional structure of a one pixel portion of a monochrome broadband polarization image sensor 115 according to this embodiment. In this case, any kind of image sensor may be used as the image sensor, which may be a CMOS image sensor or a CCD image sensor, for example.

The incoming light reaches the image capturing plane through an objective lens (not shown) which is arranged over the image sensor shown in FIG. 14. A micro lens 210 is arranged on the top surface. In this case, the micro lens 210 plays the role of converging the incoming light efficiently onto the PD 220 but also refracts the optical path of an obliquely incident light beam so that its angle of incidence is almost 90 degrees. That is why the micro lens 210 can be used particularly effectively when shooting is often carried out at a wide angle as in an endoscope, for example. In addition, the micro lens 220 can make light incident onto the array 200 of wire grid polarizers from substantially right over the array 200, and therefore, can also check the decrease in TM transmittance and extinction ratio.

Under the micro lens, arranged is a planarizing layer, under which the array 200 of wire grid polarizers is arranged to transmit only polarized light beams that are polarized in particular directions (of which the plane of polarization is rotated 45 degrees apiece) and to reflect or absorb the other light beams. In this case, the array 200 of wire grid polarizers has a hollow structure which is defined by the gaps between metallic wires as shown in FIG. 14. Since these metallic wires are in contact with the air that fills those gaps and that has a refractive index of almost 1.0, a high extinction ratio can be achieved.

The higher the level at which the array 200 of wire grid polarizers is located, the more easily such a hollow structure can be formed. For that reason, the array 200 of wire grid polarizers is arranged as the next layer right under the micro lens 210. Under the array 200 of wire grid polarizers, arranged in this order are a planarizing layer 230a and an interconnection layer 250. In this case, since no interconnects are arranged in the region that should transmit the incoming light, the incoming light can reach the underlying PD 220 without being cut by any of those interconnects. In general, in an image sensor, it is important to shorten the distance from the micro lens to the PD as much as possible and reduce its overall height. The same can be said about a polarization image sensor. That is why if the distance from the micro lens 210 to the PD 220 is too long, a crosstalk will be produced between pixels to deteriorate the polarization property (e.g., cause a decrease in extinction ratio, in particular). According to this embodiment, the distance (i.e., depth D) from the array 200 of wire grid polarizers to the PD 220, which will produce such a crosstalk between pixels with respect to polarized light, is set to be approximately 2 to 3 μm.

The array 200 of wire grid polarizers 200 exhibits a high transmittance with respect to an electromagnetic wave (TM wave), in which the electric field oscillates perpendicularly to the direction in which the metallic wires run, but exhibits a low transmittance with respect to an electromagnetic wave (TE wave), in which the electric field oscillates parallel to the direction in which the metallic wires run. That is why the TE wave is reflected from the array 200 of wire grid polarizers, and the reflected light becomes stray light to cause deterioration in performance. Thus, to avoid such a situation, it is effective to form the array 200 of wire grid polarizers as a stack of multiple layers so that the reflected light is absorbed into those layers stacked.

Figure 15:
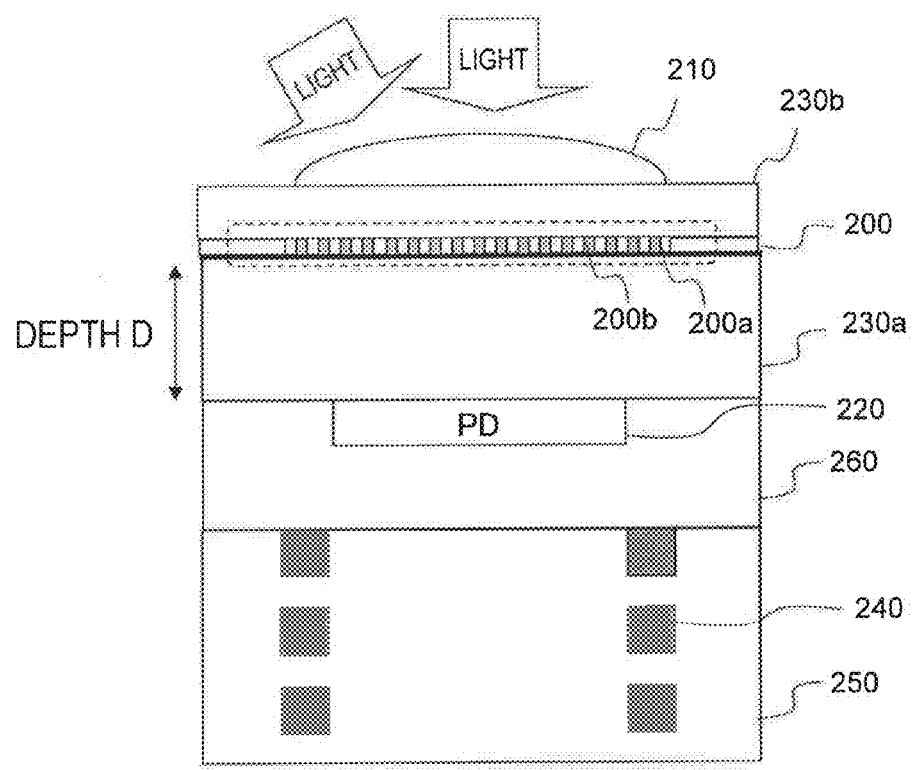
FIG. 15 illustrates an example in which a cross-sectional structure of a wire grid polarizer of a monochrome broadband polarization image sensor according to the first embodiment (in which the micro lens is arranged at the top) is applied to a backside illumination type image sensor.

FIG. 15 illustrates an exemplary cross-sectional structure of the image capturing plane of another monochrome broadband polarization image sensor 115. In this example, the image sensor 115 is a so-called "backside illumination type". In this image sensor, the micro lens 210, the array 200 of wire grid polarizers and the PD 220 are also stacked in this order so that the micro lens 210 is located closer to the light source than any other member, but there is no interconnection layer 250 over the PD 220. As a result, the height of the image sensor 115 can be further reduced and the sensitivity of the image sensor 115 can be increased. On top of that, the distance D from the wire grid polarizers to the PD can be very short, too. FIG. 16 illustrates an exemplary cross-sectional structure of the image capturing plane of still another monochrome broadband polarization image sensor 115. In the image sensor 115 of this example, the array 200 of wire grid polarizers, the micro lens 210, and the PD. 220 are stacked in this order so that the array 200 of wire grid polarizers is located closer to the light source than any other member. This is a configuration for a polarization image sensor which is supposed to be used in a state where no light should be incident obliquely onto the image sensor 115 by using a telecentric optical system, for example. By arranging the array 200 of wire grid polarizers as the top layer, there is no need to form any hollow structure any longer, which is beneficial.

Figure 17A:
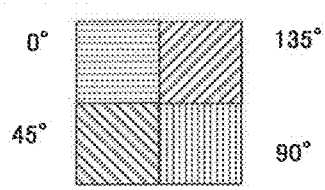
FIGS. 17A, 17B, 17C, 17D and 17E illustrate plane polarization mosaic arrangements for a monochrome broadband polarization image sensor according to the first embodiment.
Figure 17B:
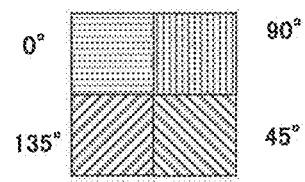
Figure 17C:
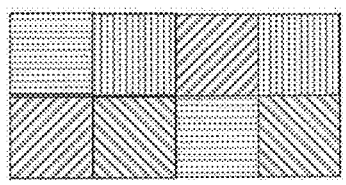
Figure 17D:
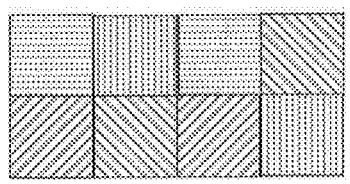
Figure 17E:
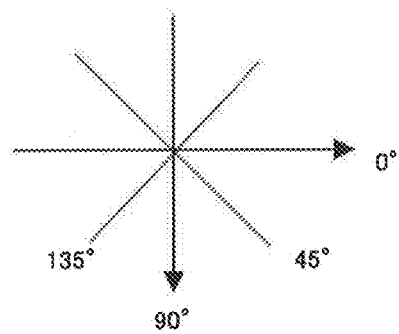

FIGS. 17A to 17E illustrate some exemplary polarization mosaic arrangements for polarizers, of which the polarization directions are defined by four different angles of 0, 45, 90 and 135 degrees on the image capturing plane of the monochrome broadband polarization image sensor 115. Specifically, FIGS. 17A and 17B illustrate examples in which each unit defining the periodic structure of the polarization mosaic arrangement is comprised of 2×2 (i.e., four) polarizers. On the other hand, FIGS. 17C and 17D illustrate examples in which each unit defining the periodic structure of the polarization mosaic arrangement is comprised of 2×4 (i.e., eight) polarizers. These four angles defining the polarization directions of the polarizers are defined by the wire directions (or azimuth angles) of the wire grid polarizer as indicated by the coordinates in FIG. 17E.

In each of these polarization mosaic arrangements, the plane may be completely covered with a number of the units that are arranged both vertically and horizontally. According to such a polarization mosaic arrangement, four kinds of wire grids with mutually different wire directions are present in every set of 2×2 polarizers that are adjacent to each other.

It should be noted that since the light reflected from an organ has a very low degree of polarization, the extinction ratio performance of the polarization image sensor 115 is raised according to this embodiment. Optionally, to maximize the performance of the polarization image sensor 115, polarizer calibration processing may be carried out.

The polarization calibration processing may be carried out in the following manner.

Specifically, image data is accumulated at the resolution of the polarization pixel structure by shooting standard objects such as a perfect diffuser, of which the degree of polarization is close to zero, using the polarization image sensor. When the object is actually observed, the pixel value IO that has been obtained at the resolution of the pixel structure is divided by the pixel value IW that has been obtained in advance by a perfect diffuser as represented by the following Equation (1). This processing may be carried out either in real time during observation by the polarization mosaic processing section 300 shown in FIG. 5 as will be described later or by an electronic circuit which is built in the image sensor 115 itself. As a result, the variation or offset in the light intensity or polarization property of each polarization pixel of the polarization image sensor 115 can be corrected and even a very low degree of polarization can also be measured accurately, which is beneficial. Specifically, if the degree of polarization DOP measured is approximately 0.05, the signal level is very low, compared to the variation or offset value of the polarization property of the image sensor 115. Even so, a sharp surface micro-geometry image can also be obtained by performing this polarization calibration processing.

$$I_i = K \times \frac{IO_i}{IW_i} \tag{1}$$

$$(i = 0, 1, 2, 3)$$

where K indicates a constant, $IO_0$, $IO_1$, $IO_2$ and $IO_3$ indicate the light intensities measured at 0, 45, 90 and 135 degrees, respectively, and $IW_0$, $IW_1$, $IW_2$ and $IW_3$ indicate the intensities measured in advance by a perfect diffuser, for example.

The video signal obtained by the monochrome broadband polarization image sensor 115 described above is then supplied to the polarization mosaic processing section 300 shown in FIG. 5. The polarization mosaic processing section 300 retrieves images from the image sensor 115 and turns those frame sequential images into RGB color images and stores them in a buffer to prepare for the image processing on the next stage. Also, based on the various kinds of mosaic arrangements that have already been described with reference to FIG. 17, the polarization mosaic processing section 300 outputs four polarization pixel values $I_0$, $I_1$, $I_2$ and $I_3$ from any location on the image plane.

Figure 18A:
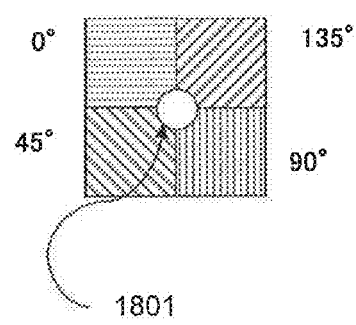
FIGS. 18A, 18B and 18C illustrate how to perform image processing according to the first embodiment.

Next, the processing to be carried out by the polarization mosaic processing section 300, a light intensity image generator 312 and a polarization degree image generator 314 will be described with reference to FIGS. 18A to 18C. Specifically, FIG. 18A indicates a virtual center pixel location 1801 of a 2×2 polarization mosaic unit. The light intensity values measured by four polarizers with mutually different polarization directions will be identified by $I_1$, $I_2$ and $I_3$. And the processing is carried out on the supposition that these values have been obtained at the center pixel location 1801 described above.

After the measurement, the light intensity image generator 312 shown in FIG. 5 calculates the average of the four polarization pixel values $I_0$, $I_1$, $I_2$ and $I_3$ that have been subjected to the calibration processing described above, thereby getting color luminance values, from which the polarization components have been canceled. Each of these color luminance values includes a luminance Y that has been determined on a color-by-color basis as a color component. In the following description, the luminance Y represents one of color components such as R, G and B components. Supposing the light intensities measured at 0 45, 90 and 135 degrees are identified by $I_0$, $I_1$, $I_2$ and $I_3$, respectively, the non-polarization luminance $Y_{AVE}$ that is their average is calculated by the following Equation (2):

$$Y_{AVE} = \frac{1}{4}(I_0 + I_1 + I_2 + I_3) \tag{2}$$

In this description, the "light intensity image" refers herein to a color image in which R, G and B components have been synthesized together. That is why if the luminances that have been calculated by Equation (2) with respect to the three color components of RGB are added together for the three color components, a light intensity image can be obtained.

The polarization degree image generator shown in FIG. 5 fits the variation in the four pixel values to a cosine function. The polarization transmission axis intersects at right angles with the wires of wire grid polarizers. If the azimuth angle of the polarization transmission axis is identified by $\psi_I$, the variation $Y(\psi_I)$ in the luminance of the four pixel values is represented by the following Equation (3) using an average luminance $Y\psi_{I\_AVE}$ the phase $\psi_o$ and the amplitude $A_I$ as variables. An example of the cosine function expressed by the following Equation (3) is shown in FIG. 18C.

$$Y(\psi_I) = Y_{ave} + A_I \cos(2(\psi_I - \psi_0)) \qquad (3)$$

Figure 18B:
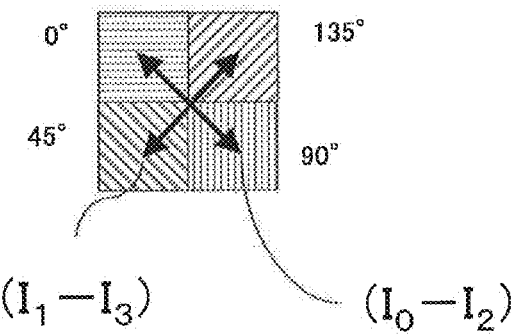
Figure 18C:
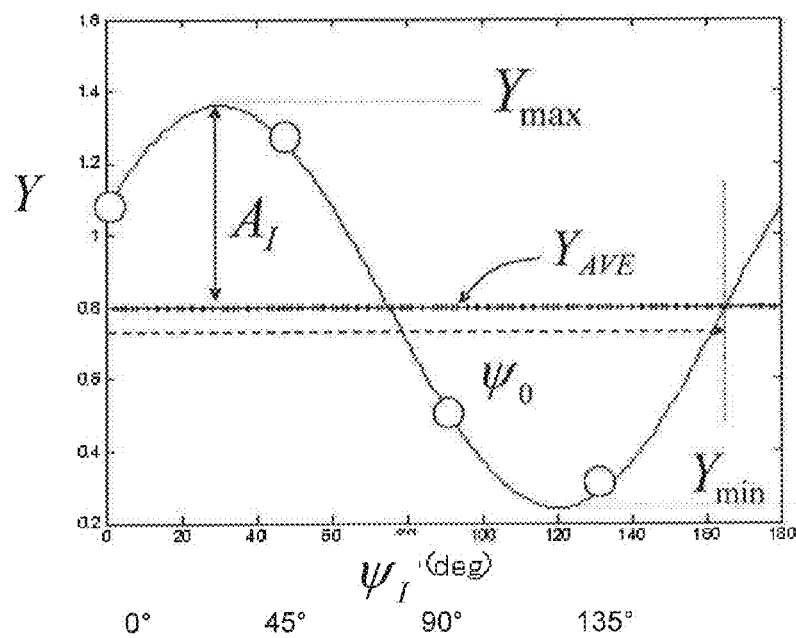

FIG. 18B shows the calculations carried out by the polarization degree image generator 314. As shown in FIG. 18B, the polarization degree image generator 314 calculates two diagonal differences $(I_0-I_2)$ and $(I_1-I_3)$. If these diagonal differences are used, the amplitude $A_I$ can be given by the following Equation (4):

$$A_I = \frac{1}{2\sqrt{(I_0-I_2)^2 + (I_1-I_3)^2}} |[(I_0-I_2)^2 + (I_1-I_3)^2]| \qquad (4)$$

$$= \frac{\sqrt{(I_0-I_2)^2 + (I_1-I_3)^2}}{2}$$

If the following Equations (5) are satisfied, the degree of polarization DOP can be calculated by the following Equation (6):

$$Y_{max} = Y_{AVE} + A_I \qquad (5)$$
$$Y_{min} = Y_{AVE} - A_I$$

$$DOP = \frac{Y_{max} - Y_{min}}{Y_{max} + Y_{min}} \qquad (6)$$

To calculate the DOP, a value is given to the center pixel location 1801 shown in FIG. 18A. The DOP is calculated at each of a lot of center pixel locations 1801 within the image capturing plane. And an image obtained by allocating these DOP values as digital values to the respective pixels is the polarization degree image. If a DOP value is expressed in eight bits, the polarization degree image may be represented as a monochrome image, of which the pixel values are 0 and 255, respectively, when the degree of polarization is zero (minimum) and when the degree of polarization is one (maximum).

The degree of polarization is basically calculated based on the diagonal differences of the 2×2 pixel unit shown in FIG. 18B. However, this computation requires calculating the difference between adjacent pixels, and therefore, is easily susceptible to noise. As a result, some artifact such as a moiré pattern is often produced on a polarization degree image. To avoid producing such artifacts, the highest frequency of the image (i.e., the maximum value of the spatial frequency) may be lowered before the degree of polarization is calculated. Specifically, a full-resolution image that has been captured by the broadband polarization image sensor 115 may be subjected to low-pass filter processing. The low-pass filter processing may be carried out through image processing, not optically. Alternatively, by using a 2×2 unit pixel as a virtual single pixel unit without using the maximum resolution, the overall image size may be cut down to ½×½.

FIG. 19A is a block diagram illustrating an exemplary configuration for performing real time processing on the values calculated by the light intensity image generator 312 and the polarization degree image generator 314. First of all, the four pixel values $I_0$, $I_1$, $I_2$ and $I_3$ supplied from the polarization mosaic processing section 300 to the light intensity image generator 312 are added together, and its average is calculated, by the light intensity image generator 312, which outputs $Y_{AVE}$ that has been obtained as the average of the sum. In the meantime, the values of the two pairs of diagonal pixels $(I_0, I_2)$ and $(I_1, I_3)$ are supplied to the polarization degree image generator 314, which gets the amplitude $A_I$ calculated by a calculator based on the two diagonal differences $(I_0-I_2)$ and $(I_1-I_3)$ described above. This calculation is carried out in accordance with Equation (4).

Finally, by performing the calculations represented by Equations (5) and (6) based on $Y_{ABE}$ and $A_I$, the degree of polarization DOP is calculated.

It should be noted that these processing steps shown in the block diagram of FIG. 19A may be performed either by dedicated hardware components or using a high-speed software program in the image processor 110 of this embodiment. However, the polarization image sensor 115 may include the calculator shown in this block diagram. If the polarization image sensor 115 includes such a calculator, then an ordinary color image (i.e., a light intensity image) and a polarization degree image may be output from the polarization image sensor either simultaneously or selectively. A control signal may be input to the polarization image sensor 115 through a control signal line to make the polarization image sensor 115 output a normal color image in one mode and a polarization degree image in another mode.

FIG. 19B illustrates what kind of processing is carried out by the degree of retouching section.

As already described with reference to FIG. 4, according to this embodiment, the polarization degree image generated is subjected to a special kind of retouch in order to present it as an easily recognizable image to a doctor who is a human viewer. In the related art, a result of polarization degree image processing has often been displayed as a pseudo color image. For example, it is known that $\psi_0$ obtained by subjecting the cosine function represented by Equation (3) to fitting and DOP are allocated to the hue and saturation of a pseudo-color signal. However, such a presentation is just a method of visualizing a piece of polarization information. On the other hand, according to this embodiment, a retouch into an easily recognizable image for a human viewer by enhancing the surface topography is carried out by the following two methods:

(1) Light Intensity Mode

In the light intensity mode, a normal color light intensity image is displayed as an enhanced one so that concaves will look even darker and the convexes will look even brighter. In this case, an image in which the concaves look dark and the convexes look bright (which will be referred to herein as an "enhanced image") may be superposed on a color light intensity image (which will be referred to herein as a "reference image"), or the enhanced image and the reference image may be selectively displayed by itself. Such an image in which the concaves look dark and the convexes look bright may be obtained based on the polarization degree image.

Specifically, if the polarization degree image is subjected to processing in which the degree of polarization is enhanced and then inverted, an enhanced image can be obtained. This processing may be carried out by the following Equation (7):

$$DOP1 = 1 - \text{Enhance}(DOP) \qquad (7)$$

where the Enhance function is a function of enhancing the input linearly and nonlinearly. DOP1 obtained as a result of this processing is a color image having R, G and B components but can be said to be a gray image because its R, G and B components have the same values.

Figure 19C:
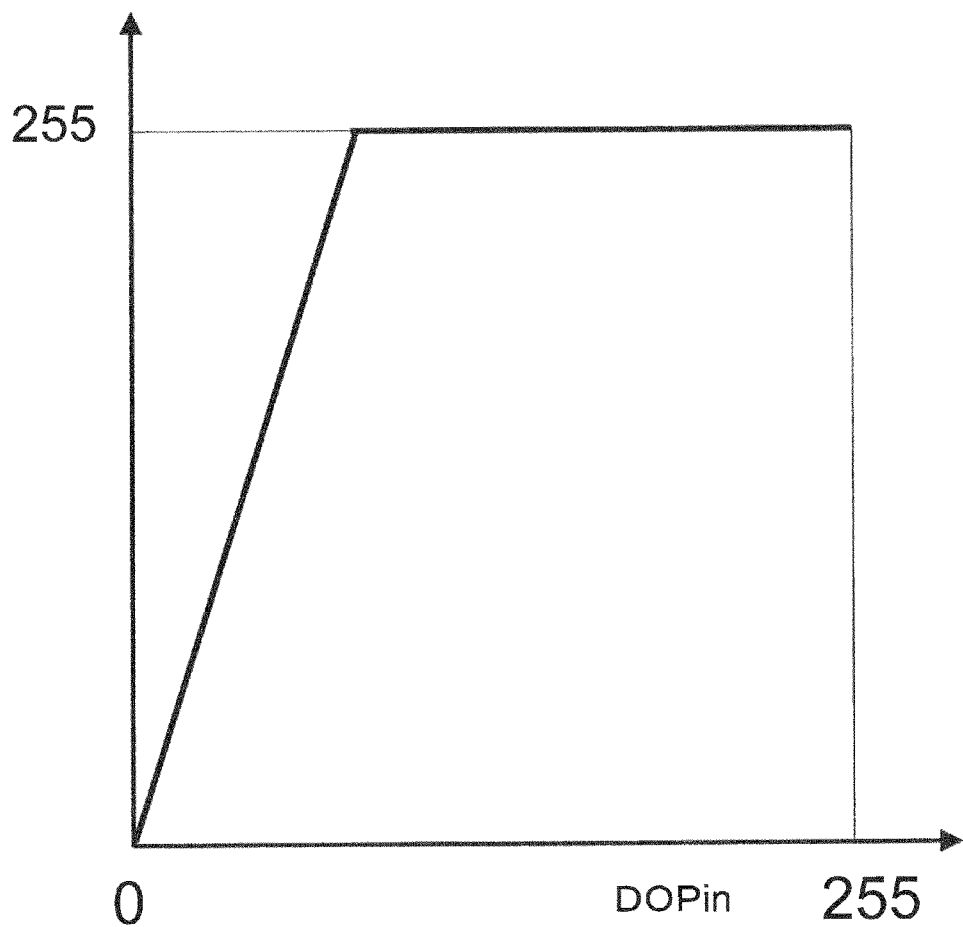
FIG. 19C illustrates one example of Enhance function used in a retouching section according to the first embodiment.

FIG. 19C shows an example of the Enhance function. A degree of polarization DOP which is represented as an eight-bit signal is enhanced into a degree of polarization DOP1 which is also represented as an eight-bit signal. Although the gain is supposed to be increased linearly in the example shown in FIG. 19C, the Enhance function may also have any other arbitrary shape. To observe the surface topography of a translucent object, the weakly polarized light of the internally diffused light is enhanced to the point that it can be seen as a polarization degree image. The gain of the Enhance function may be set to be approximately 50×, for example.

(2) Blue Pigment Mode

In the blue pigment mode, the concaves are displayed in dark blue as if the concaves were filled with an indigo carmine solution, and the convexes are displayed as they are as a color image. This processing can get done by enhancing the degree of polarization and then performing HSV color processing. And this processing may be carried out in accordance with the following Equation (8), for example:

DOP2=HSV2RGB(Blue_hue,Enhance(DOP),1)     (8)

where HSV2RGB ( ) function is a function of converting an HSV color space defined by the hue H, saturation S and value V into an RGB color space. In this embodiment, the hue is fixed at Blue_Hue that is the hue of the color blue and the value is fixed at the maximum value of 1. And the saturation is determined so that the depth of the color blue is increased where DOP is high. DOP2 obtained in this manner is a color image.

The image synthesizing section 320 synthesizes together the light intensity image $Y_{AVE}$ and the polarization degree image DOP1 or DOP2 that has been retouched as described above by calculating the weighted sum on a color component basis. If the weighting coefficient is W, this synthesizing processing step can be represented by the following Equations (9):

OUTIMAGE1=$W \times Y_{AVE}$+(1−$W$)×DOP1

OUTIMAGE2=$W \times Y_{AVE}$+(1−$W$)×DOP2

(0≤$W$≤1)     (9)

By setting W in Equations (9) to be various values, multiple different kinds of images can be obtained. For example, if W=1, a normal color image is obtained. On the other hand, if W=0, a retouched polarization degree image is obtained. By changing W freely, the color light intensity image and the polarization degree image can be synthesized together at any arbitrary ratio so that the resultant image is easily recognizable for a doctor. In a situation where the top surface micro-structure is observed at the same time with the lower capillary pattern which is seen through a translucent mucosa, if an indigo carmine solution is sprinkled by the conventional method, the surface micro-structure can be seen more clearly but the background capillary vessels tend to be hidden. According to embodiments of the present disclosure, however, not only the surface micro-structure but also the background capillary tubes can be observed at the same time.

The present inventors actually captured an image of an object and subjected it to image processing using the image capturing processor of this embodiment. The results will be described below. In this case, the object was not a real organ but a retailed square translucent lenticular plate made of acrylic with sizes of 50 mm×50 mm×2 mm. The lenticular plate was in the color yellow and was not transparent, but light could diffuse inside the plate. The surface grooves had a pitch of 0.7 mm and a convex radius of 0.5 mm.

Figure 20:
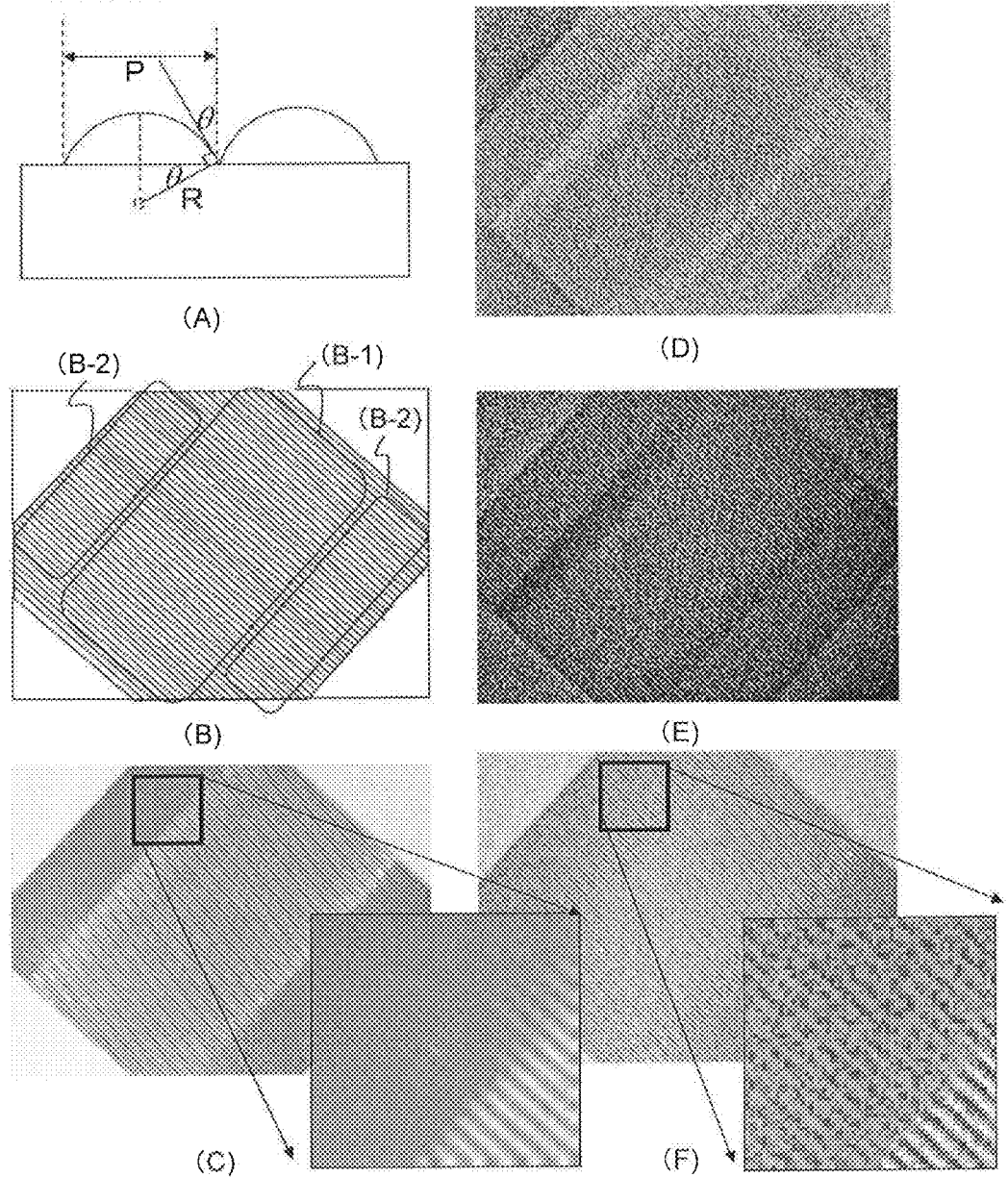
FIG. 20 shows the results of experiments in which the micro-geometric texture detected was enhanced using a translucent lenticular plate as an object simulating an organism's mucosa.

Portion (A) of FIG. 20 is a schematic cross-sectional view illustrating a portion of the object on a larger scale. The maximum angle defined by a normal with respect to a depression on the object surface is 45.57 degrees (which is almost 45 degrees) as represented by the following Equation (10):

$$\theta_{max} = \cos^{-1}\left(\frac{P}{2R}\right) = \cos^{-1}\left(\frac{0.7}{2 \times 0.5}\right) = 45.57° \quad (10)$$

Portion (C) of FIG. 20 illustrates a light intensity image which represents the surface of a lenticular plate and which has been obtained by shooting. In portion (B) of FIG. 20, black solid lines schematically indicating the directions and lengths of the micro-geometric grooves have been drawn on the image shown in portion (C) of FIG. 20. Those grooves are formed over the entire object. In this case, the object has been shot with the shooting optical axis tilted with respect to the lenticular plate.

In the bright striped areas in the vicinity of the center of the area (B-1) shown in portion (B) of FIG. 20, the light that has been cast from a ring light source used for shooting is reflected regularly. In the area (B-1), a bright and dark pattern is observed along the surface micro-geometric grooves.

On the other hand, in the areas (B-2) shown in portion (B) of FIG. 20, the incoming light is internally diffuse-reflected. In these areas (B-2), almost no bright and dark pattern is observed as is usually the case with a translucent object. That is to say, in these areas (B-2), the micro-structure cannot be detected by the light intensity.

FIGS. 20(D) and 20(E) respectively illustrate an enhanced version Enhance(DOP) and an inverted version DOP1 of the polarization degree image. The shooting session was carried out using a color camera and a rotating polarizer of glass and the actual extinction ratio turned out to be approximately 166:1. The results of the experiments the present inventors carried out revealed that if a retailed polarization camera with an extinction ratio of approximately 6:1 was used to capture these polarization images, the degree of polarization was drowned in noise and the image quality rather decreased even if the images were enhanced. However, if the extinction ratio of the polarizer is set to be 100:1 or more, an image with little noise can be obtained.

Portion (F) of FIG. 20 illustrates an exemplary synthetic image. Comparing the images shown in Parts (C) and (F) of FIG. 20 to each other, it can be seen that the micro-geometric grooves that have caused the internal diffuse reflection in the areas (B-2) and that are invisible on the light intensity image have been enhanced and now visible. It can also be seen that the image of the micro-geometric grooves that have caused the internal diffuse reflection in the areas (B-2) and the image of the micro-geometric grooves that have caused the specular reflection in the area (B-1) have been matched to each other and are now continuous with each other.

The image processing described above may also be performed by a known computer in which an image processing program is stored. Such an image processing program may be designed to cause the computer to execute the steps of: generating a light intensity image based on the output of an image sensor; generating a polarization degree image by calculating the degree of polarization on a pixel-by-pixel basis based on the output of the image sensor; generating a retouched polarization image by enhancing the degree of polarization of the polarization degree image at depressions on a micro-geometric surface of the object and by correcting at least one of its hue, saturation and value; and synthesizing the retouched polarization image and the light intensity image together. Such a program may be stored in a computer-readable non-transitory storage medium which the control section 110 of the image capturing processor includes.

It should be noted that a similar program to the image processing program described above could also be made when image processing according to any of the other embodiments to be described below is carried out.

Embodiment 2

Figure 21:
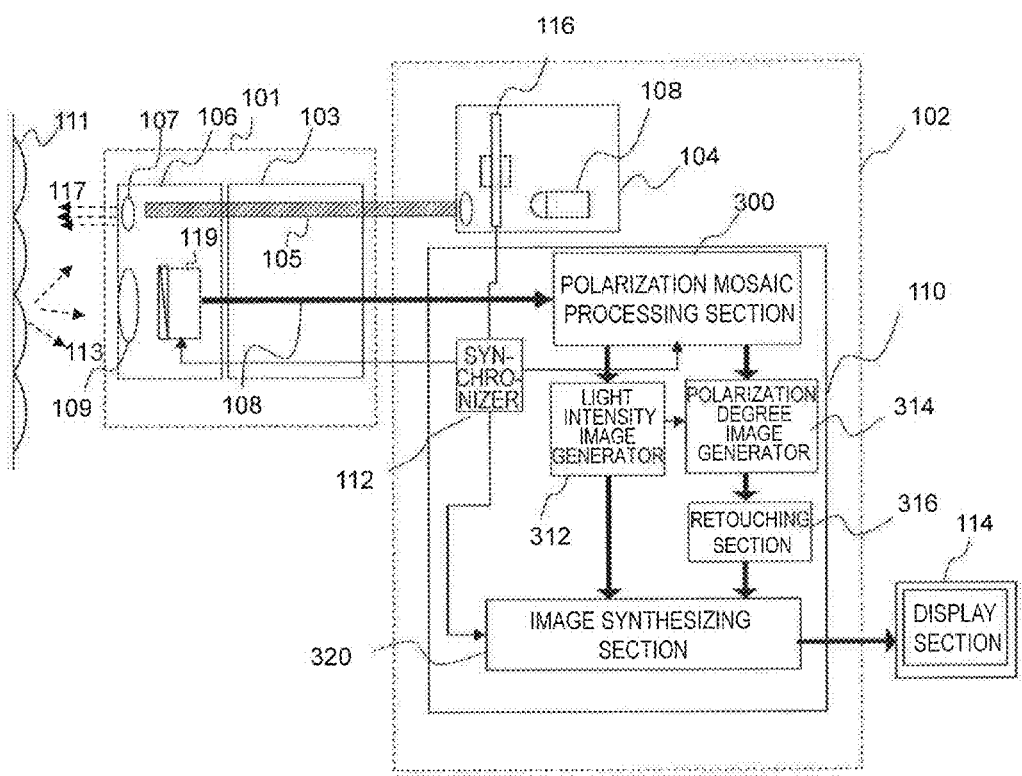
FIG. 21 illustrates a second embodiment of the present disclosure.

FIG. 21 schematically illustrates an overall configuration for an image capturing processor as a second embodiment of the present disclosure. In this second embodiment, a color image is captured by a single-chip color polarization image sensor 119 by irradiating the object with white light, which is a major difference from the first embodiment described above.

According to this embodiment, the non-polarized white light emitted from the light source section 104 is transmitted through the light guide 105 and irradiates the object with non-polarized white illuminating light 117. The light reflected from the object is observed by the color polarization image sensor 119. The rest of the processing is the same as what has already been described for the first embodiment, and description thereof will be omitted herein. Thus, the following description of the second embodiment will be focused on the configuration of the color polarization image sensor 119.

Figure 22:
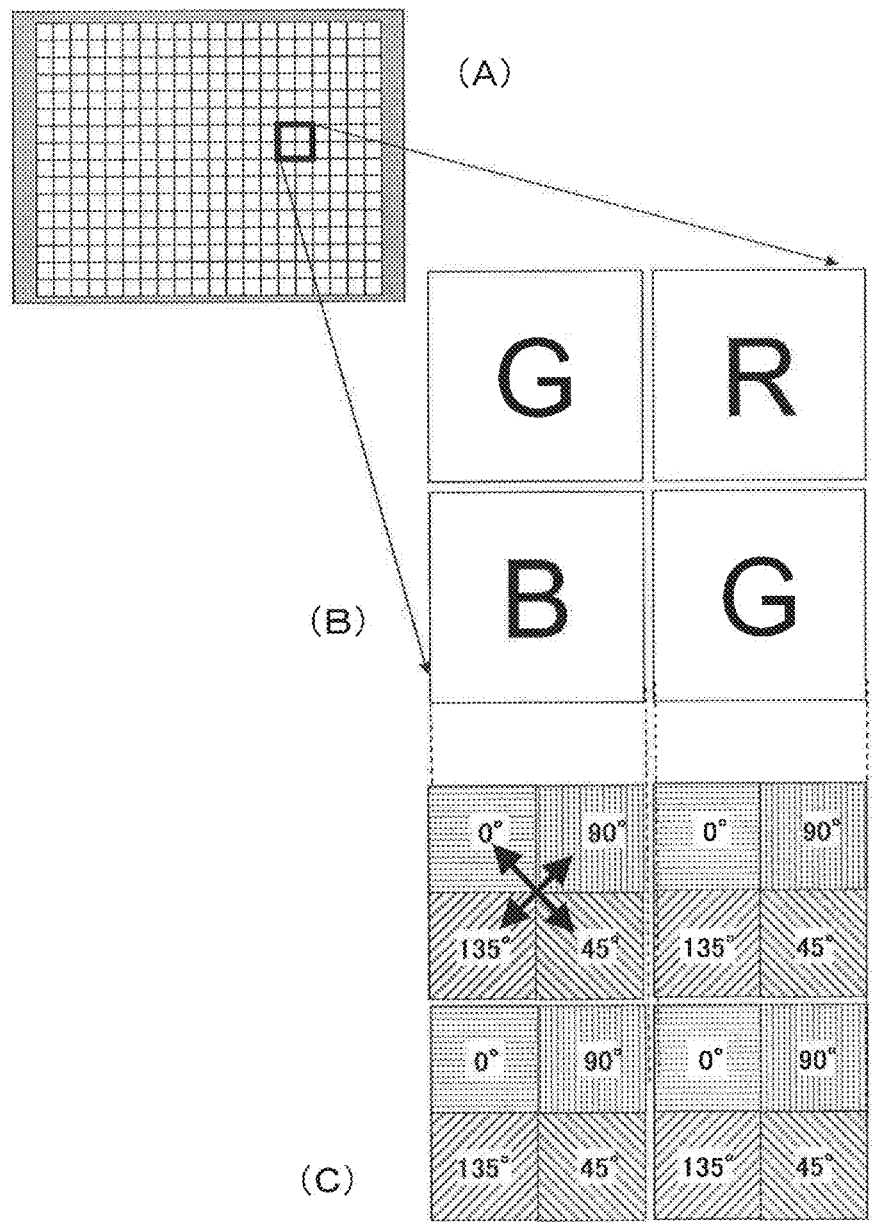
FIG. 22 illustrates a color polarization composite mosaic structure for a color polarization image sensor according to the second embodiment.

FIG. 22 illustrates a planar structure of the color polarization image sensor 119 according to this embodiment. As shown in portions (A) and (B) of FIG. 22, color mosaic filters are arranged in the color polarization image sensor 119 of this embodiment unlike a monochrome single-chip image sensor. Although three kinds of color filters (i.e., RGB color filters) are arranged in this example in the pattern of a Bayer mosaic, color filters may also be arranged in any other mosaic pattern. As shown in portion (C) of FIG. 22, each of these color filters is associated with a subpixel structure, which is a mosaic comprised of four different kinds of polarization subpixels. Considering each of these subpixels as a unit element, the resolution of this image sensor decreases to a quarter (=½× ½) of the original one. Nevertheless, since polarization information can be obtained within a single pixel corresponding to each color filter, the artifact that would be caused as a result of polarization processing can be reduced.

Figure 23:
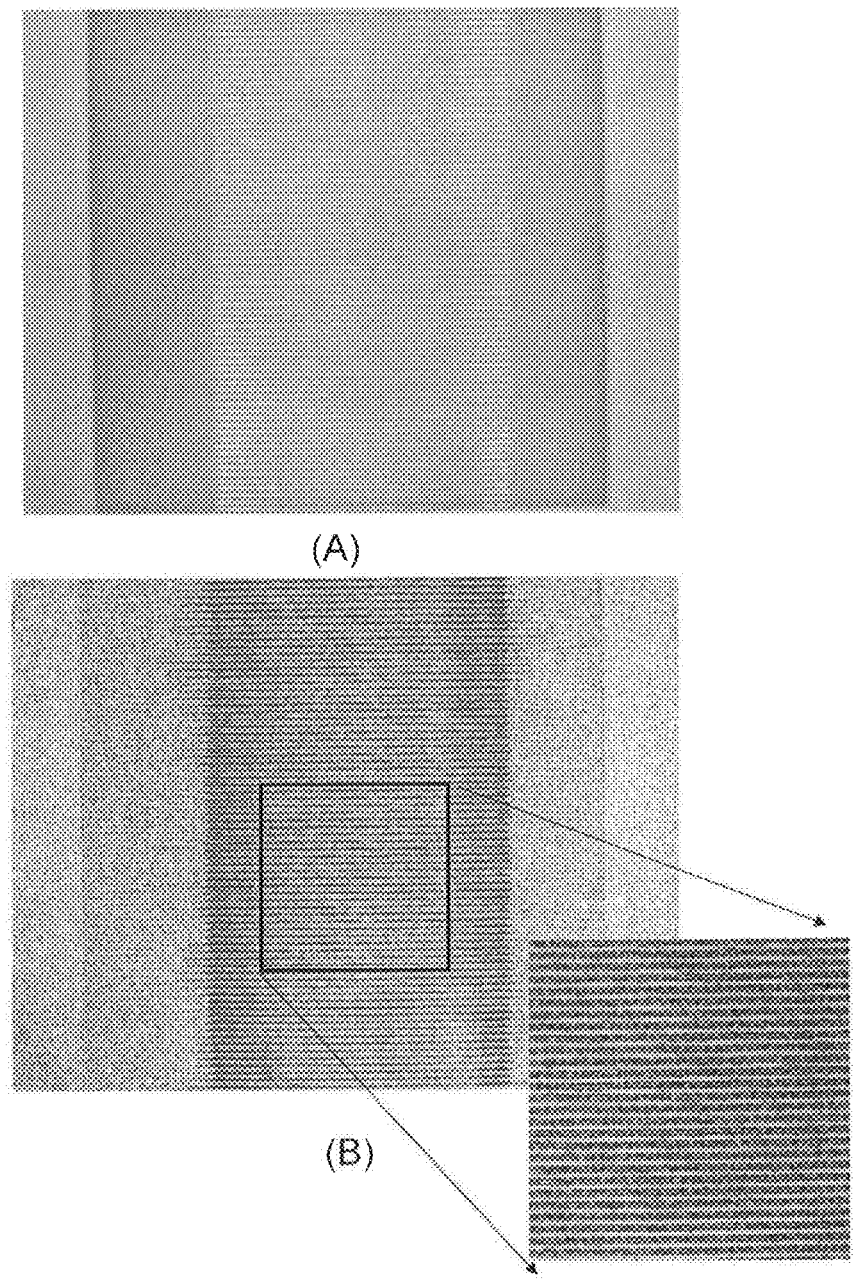
FIG. 23 illustrates an artifact caused by polarization processing.

FIG. 23 shows a result of experiments revealing what kind of artifacts occurred as a result of polarization processing. Specifically, in this example, a lenticular plate was irradiated with a ring light source, and shot with a monochrome polarization camera (PI-100 produced by Photonic Lattice) having a periodic polarization mosaic, of which the fundamental period is defined by 2×2 fine pixels as in this embodiment, thereby obtaining a polarization degree image. portion (A) of FIG. 23 illustrates a light intensity image which was obtained as the average of the four surrounding pixels and portion (B) of FIG. 23 illustrates a polarization degree image. Each of these images represents the lenticular plate comprised of 1120×868 pixels. It can be seen that in an area of the polarization degree image shown in portion (B) of FIG. 23, moiré fringes, absent from the light intensity image shown in portion (A) of FIG. 23, were produced as can be seen from the enlarged view of the area within the solid line frame. Such moiré fringes would have been produced probably because a dark and bright pattern was observed in this area at the light intensity of the lenticular plate because the light emitted from the ring light source would be regularly reflected from that area and because the frequency of that pattern would fall within the frequency range of the 2×2 polarization mosaic. When the processing of generating a light intensity image is carried out, the pixels surrounding each polarization mosaic pixel is averaged, and therefore, the artifact can be reduced. However, when the processing of generating a polarization degree image is carried out, the diagonal differences between each pixel and its adjacent pixels are calculated as shown in FIG. 22(C), and therefore, the light intensity difference is amplified and the artifact increases.

To avoid such a situation, the range to calculate those diagonal differences should be as small a local area on the image as possible. If a number of polarization pixels are associated with subpixels in a single color filter, the spatial frequency of the image to enhance can be increased and the frequency of occurrence of such artifacts can be reduced. According to conventional technologies, a single polarization pixel is often provided for only a color filter in a single color in a color mosaic filter. In that case, however, the spatial frequency of those diagonal pixels will shift to a lower range and is more likely to interfere with the spatial frequency of a scene shot, which is not a favorable situation.

Figure 24:
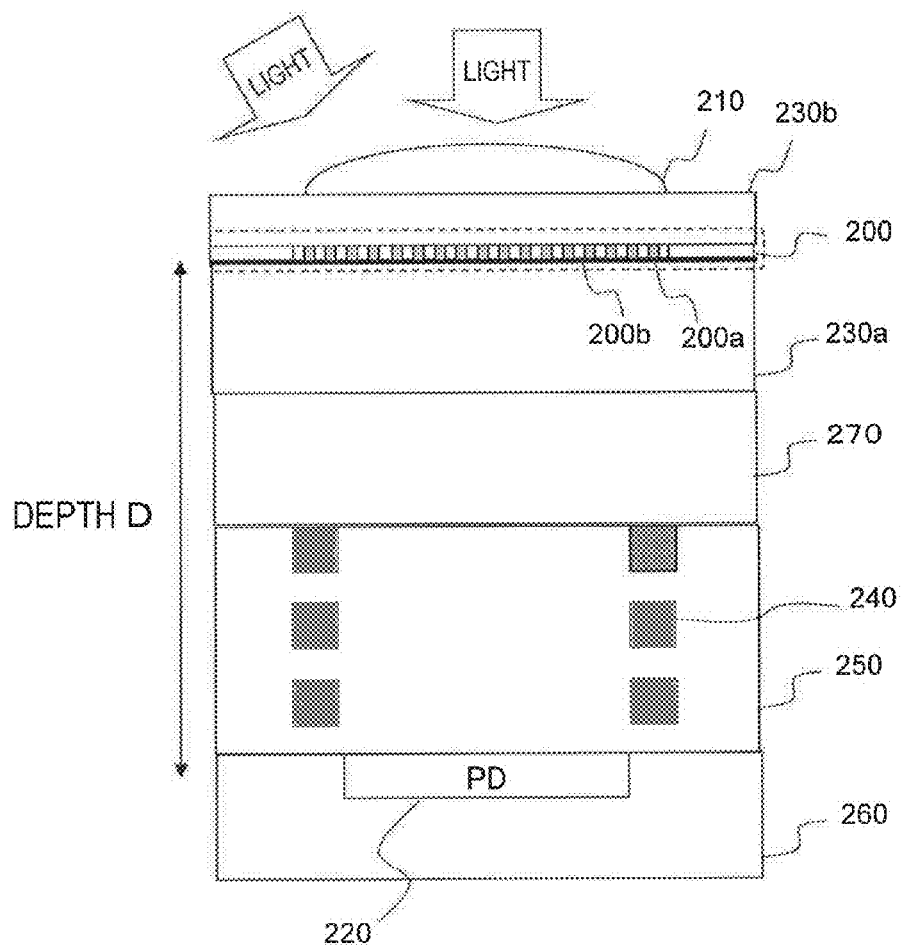
FIG. 24 illustrates an exemplary cross-sectional structure for a color polarization image sensor according to the second embodiment.

FIG. 24 illustrates a cross-sectional structure of a color polarization image sensor 119 according to the present disclosure. Unlike the monochrome broadband polarization image sensor 115 shown in FIG. 14, color filters 270 are arranged between the array 200 of wire grid polarizers and the PD (photodiode) 220. These color filters 270 may be made of either an organic substance or a photonic crystal. When viewed along the direction in which the light emitted from the light source travels to the PD 220, the micro lens 210, the array 200 of wire grid polarizers, and the color filters 270 may be arranged in six different orders, in which respectively different advantages would be achieved. Since the color filters 270 are added in this embodiment, the distance D from the wire grid polarizers to the PD increases to typically the range of 4 to 6 μm.

In the configuration shown in FIG. 24, the micro lens is arranged at the top, and therefore, incoming light can be incident perpendicularly onto the array 200 of wire grid polarizers, which is beneficial. Since the array 200 of wire grid polarizers is arranged closer to the light source than the color filters 270 are, the array 200 of wire grid polarizers needs to operate in a broad range. However, as the wire grid polarizers are arranged right under the micro lens, a hollow structure in which an air layer is brought into contact with the array 200 of wire grid polarizers can be formed easily.

Figure 25:
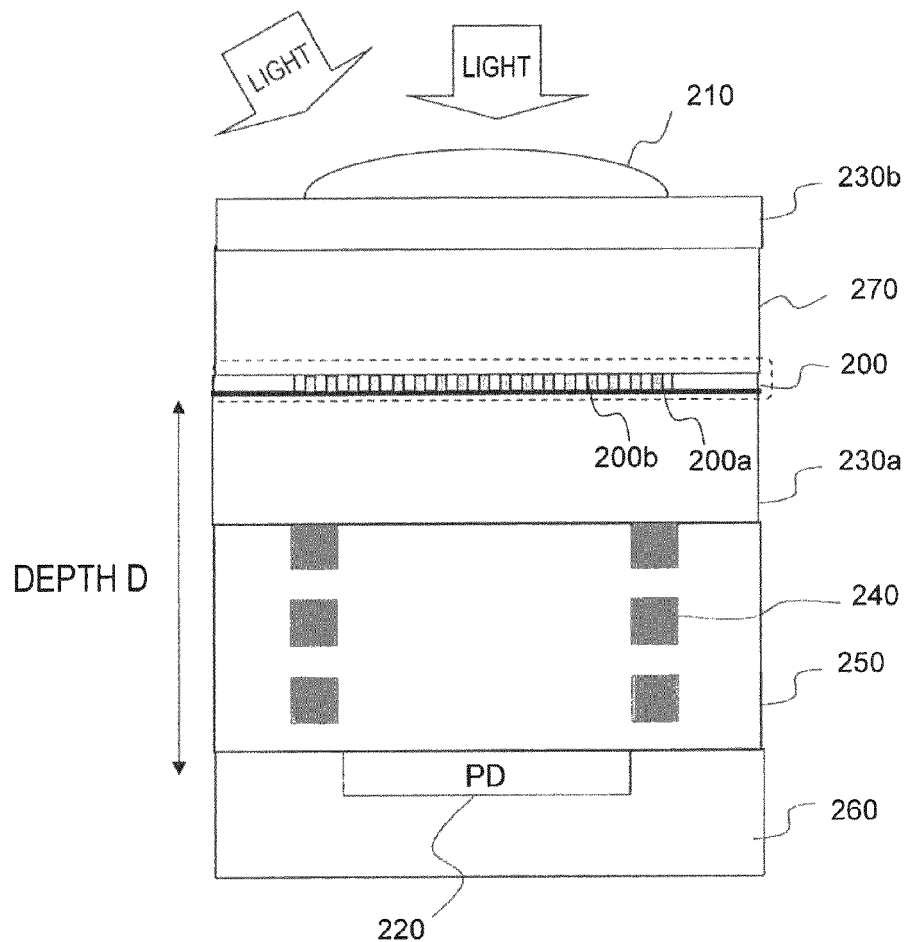
FIG. 25 illustrates another exemplary cross-sectional structure for a color polarization image sensor according to the second embodiment.

FIG. 25 illustrates another exemplary cross-sectional structure for a color polarization image sensor 119 according to this embodiment. In this example, the micro lens 210, the color filters 270, and the array 200 of wire grid polarizers are stacked in this order from top to bottom. Since the micro lens 210 is arranged at the top, incoming light can be incident perpendicularly onto the array 200 of wire grid polarizers, which is beneficial. In addition, as the array 200 of wire grid polarizers is arranged under the color filters 270 according to this configuration, the array 200 of wire grid polarizers may be a narrow band one. On top of that, since neither the color filters 270 nor the micro lens 210 is interposed between them, the distance D from the wire grid polarizers to the PD can be shortened, which is also advantageous.

Figure 26:
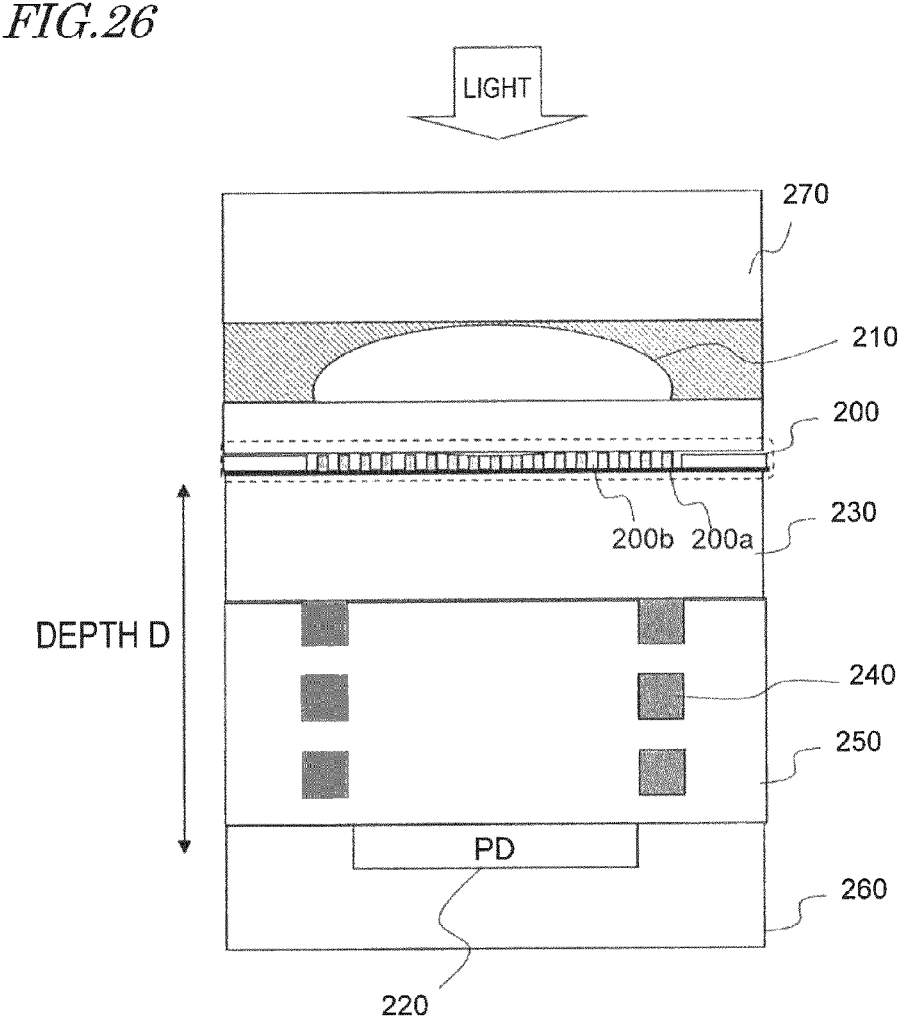
FIG. 26 illustrates still another exemplary cross-sectional structure for a color polarization image sensor according to the second embodiment.

FIG. 26 illustrates still another exemplary cross-sectional structure for a color polarization image sensor 119 according to this embodiment. In this example, the color filters 270, the micro lens 210, and the array 200 of wire grid polarizers are stacked in this order from top to bottom. In this configuration, as the incoming light is transmitted through the color filters 270 and then through the array 200 of wire grid polarizers, a narrow band one exhibiting some wavelength dependence with respect to RGB wavelength ranges, for example, may be provided as the array 200 of wire grid polarizers, thus increasing the freedom of design. In addition, since the micro lens is arranged over the wire grid polarizers, incoming light can be incident perpendicularly onto the wire grid polarizers, which is beneficial. On top of that, since neither the array of color filters nor the micro lens is interposed between them, the distance D from the wire grid polarizers to the PD can be shortened, which is also advantageous.

Figure 27:
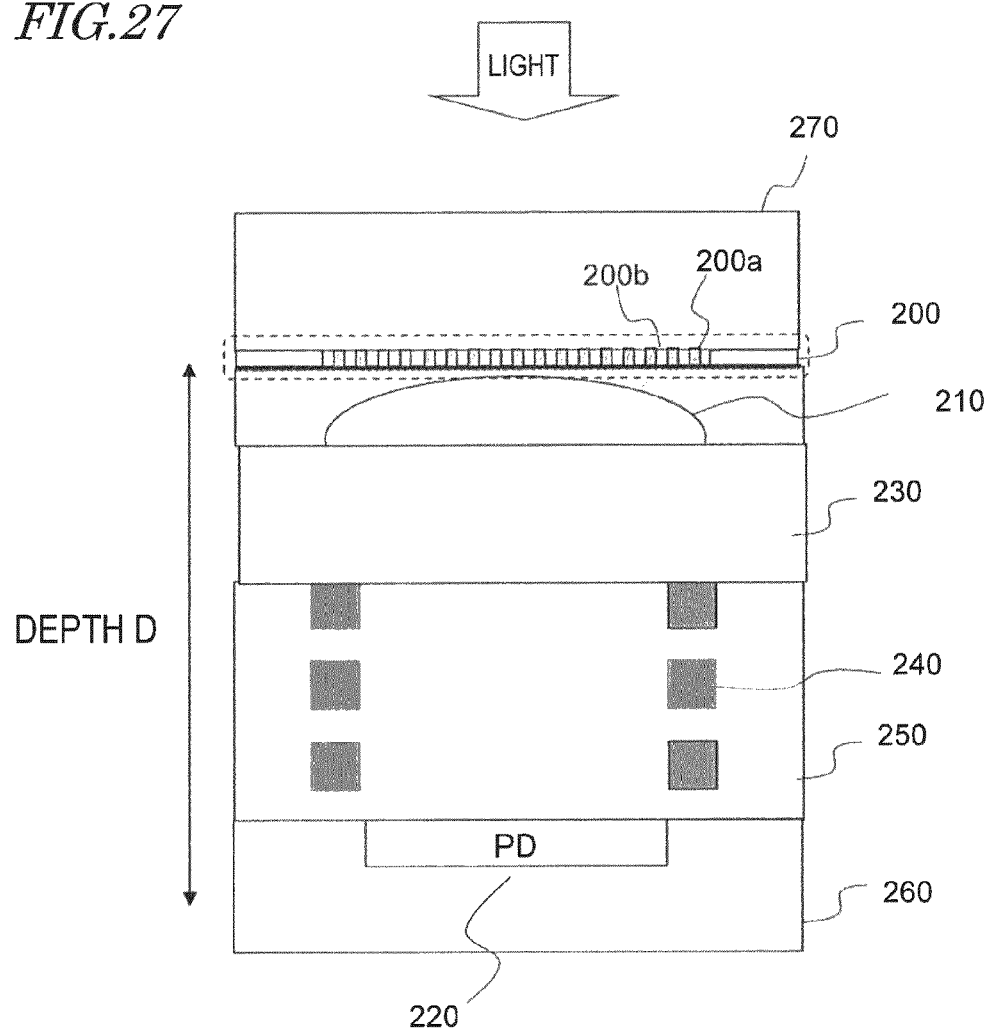
FIG. 27 illustrates yet another exemplary cross-sectional structure for a color polarization image sensor according to the second embodiment.

FIG. 27 illustrates yet another exemplary cross-sectional structure for a color polarization image sensor 119 according to this embodiment. In this configuration, the color filters 270, the array 200 of wire grid polarizers and the micro lens 210 are stacked in this order from top to bottom. In this configuration, as the incoming light is transmitted through the color filters 270 and then through the array 200 of wire grid polarizers, a narrow band one exhibiting some wavelength dependence with respect to RGB wavelength ranges, for example, may be provided as the array 200 of wire grid polarizers, thus increasing the freedom of design. In addition, as the array 200 of wire grid polarizers is arranged right under the color filters 270, a hollow structure can be formed easily. On top of that, since the array of color filters is not interposed between them, the distance D from the wire grid polarizers to the PD can be shortened, which is also advantageous.

Figure 28:
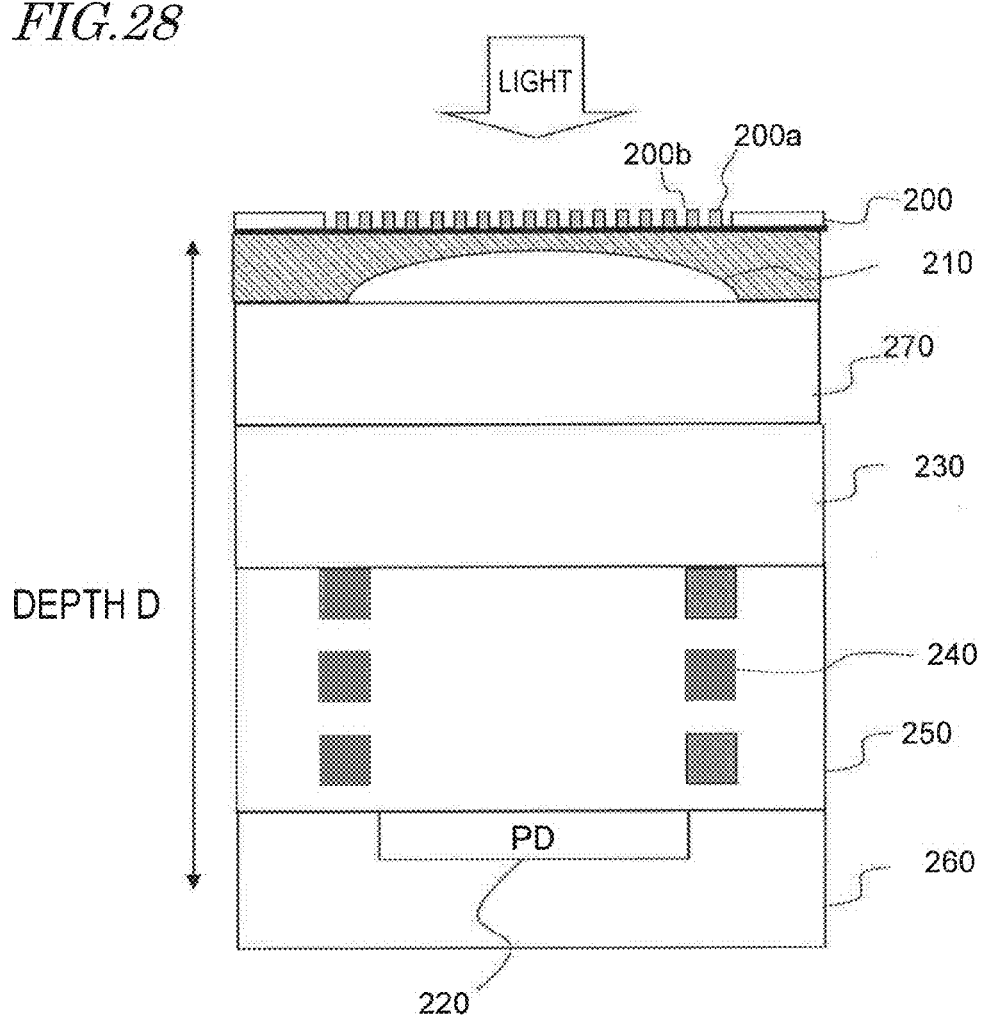
FIG. 28 illustrates yet another exemplary cross-sectional structure for a color polarization image sensor according to the second embodiment.

FIG. 28 illustrates yet another exemplary cross-sectional structure for a color polarization image sensor 119 according to this embodiment. In this configuration, the array 200 of wire grid polarizers, the micro lens 210 and the color filters 270 are stacked in this order from top to bottom. Since the array 200 of wire grid polarizers is arranged closer to the light source than the color filters 270 are, the array 200 of wire grid polarizers needs to operate in a broad range. However, as the array 200 of wire grid polarizers is arranged at the top, there is no need to make any hollow structure, which is advantageous.

Figure 29:
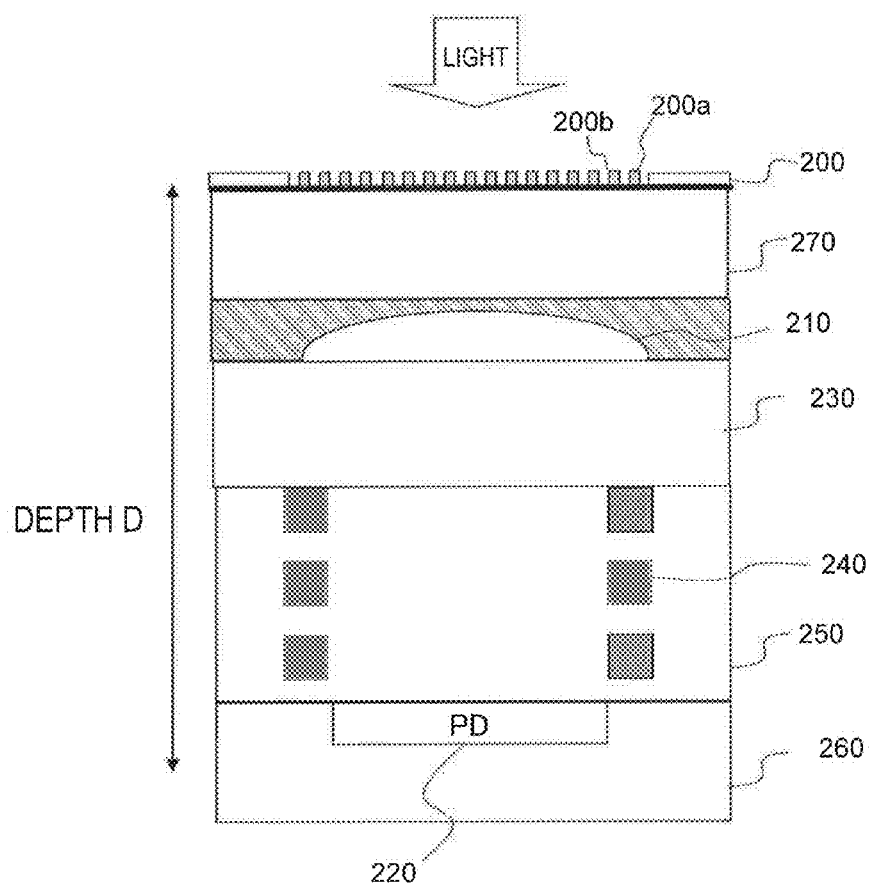
FIG. 29 illustrates yet another exemplary cross-sectional structure for a color polarization image sensor according to the second embodiment.

FIG. 29 illustrates yet another exemplary cross-sectional structure for a color polarization image sensor 119 according to this embodiment. In this configuration, the array 200 of wire grid polarizers, the color filters 270, and the micro lens 210 are stacked in this order from top to bottom. Since the array 200 of wire grid polarizers is arranged closer to the light source than the color filters 270 are, the array 200 of wire grid polarizers needs to operate in a broad range. However, as the array 200 of wire grid polarizers is arranged at the top, there is no need to make any hollow structure, which is advantageous.

It should be noted that a quartz LPF (low-pass filter), which is a member to be used often with a color mosaic structure, utilizes a birefringence phenomenon and may possibly disturb the polarization, and therefore, should not be employed basically. However, if a quartz LPF should be used to improve the color image quality using Bayer color mosaic filters, the quartz LPF could be inserted under (on a stage following) the array 200 of wire grid polarizers.

Any of these alternative configurations is applicable to the backside illumination type image sensor shown in FIG. 15 and the sensitivity can be increased by decreasing the height of the image sensor. However, as this is just a part of known technologies, its description will be omitted herein.

It should be noted that although both of the first and second embodiments described above are supposed to be applied to an ordinary endoscope, these embodiments could also be applied to a capsule endoscope (not shown) as they are. In the case of a capsule endoscope, however, an internal body tissue is basically shot in water, and therefore, the conventional indigo carmine solution cannot be sprinkled as a matter of principle. That is why as the surface micro-structure of a translucent mucosa cannot be observed by any conventional method, this embodiment can be used effectively in such a situation.

Embodiment 3

Figure 30:
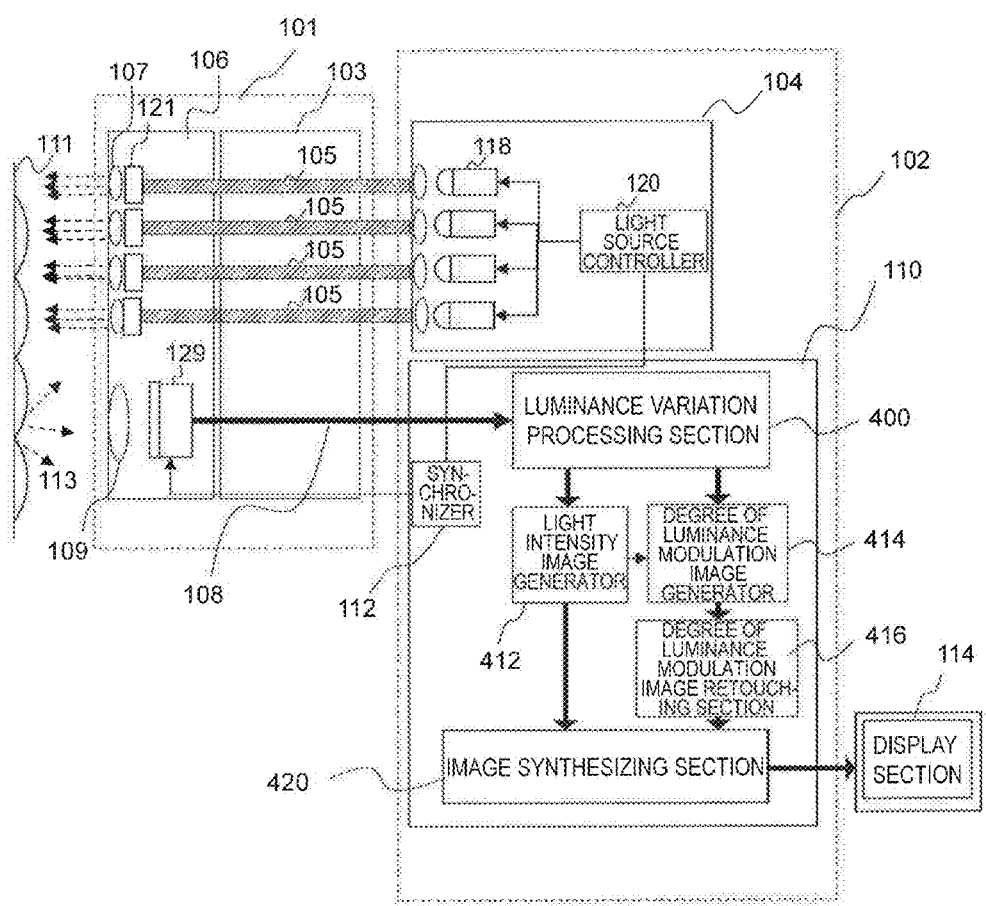
FIG. 30 illustrates a third embodiment of the present disclosure.

FIG. 30 schematically illustrates an overall configuration for an image capturing processor as a third embodiment of the present disclosure.

According to this third embodiment, the object is irradiated with polarized light as illuminating light, and therefore, there is no need to use any polarization image sensor, which is a major difference from the first and second embodiments. Specifically, according to this embodiment, the object is irradiated with white light emitted from a polarization-rotating light source and a color image is captured using a single-panel color image sensor. An image is captured one by one by each of four polarized light sources, of which the polarization planes define mutually different angles. And by observing the variation in light intensity on a pixel-by-pixel basis, a pseudo-polarization image is captured.

Non-polarized white light beams emitted from four lamps 118 that are arranged in the light source section 104 are input sequentially and selectively to four light guides 105 by a light source controller 120. At the respective tips of these four light guides 105, arranged are four polarizers 121, of which the polarization transmission axes have mutually different directions. Specifically, in this example, the directions of the polarization transmission axes of the polarizers 121 define angles of rotation of 0, 45, 90 and 135 degrees as viewed from an image capturing plane coordinate system. That is why by sequentially inputting the light beams as described above, a polarized light source, of which the plane of polarization changes into four different angles, is realized. By switching the sequential input at high speeds, the plane of polarization of the illuminating light can be changed smoothly between the four different angles.

Synchronously with the supply of the signal to the light source controller 120, the synchronizer 112 sends an image capturing timing signal to the color image sensor 129, thereby capturing images continuously. It is difficult for a multi-mode optical fiber for illumination which is used ordinarily to transmit light while maintaining its polarization. For that reason, according to this embodiment, non-polarized light is transmitted through each of the light guides 105 and then transformed into polarized light at its tip portion. Such an optical fiber for illumination that can maintain the polarization is realized by bundling together a number of single-mode fibers for fiber optics communications. If such a polarization-maintaining illuminating optical fiber is used, there is no need to attach any polarizer to the tip portion. In that case, the light source section 104 may produce illuminating light, of which the polarization plane rotates, and may transmit the light through the light guides 105.

Such a polarization-rotating light source may also be realized by attaching a plane of polarization control element which may be made of liquid crystal, for example, to the end of the light guides and by controlling the plane of polarization with the control element driven with an applied voltage. In that case, since the birefringence and other physical properties of the liquid crystal and an optical element to use (such as a quarter wave plate) have wavelength dependence, it is difficult to operate the polarization-rotating light source in the entire wavelength range of the white light.

Next, it will be described with reference to FIGS. 31A to 31C on what principle internally diffused light in a translucent object may be observed using such a polarization-rotating light source.

As already described with reference to FIGS. 1 through 4, in each of the embodiments of the present disclosure, not only polarized light to be produced just locally by getting the incoming light reflected twice but also polarized light to be produced only faintly but globally due to internal diffuse reflection are observed. Hereinafter, it will be described on what principle such polarized light produced by the internal diffuse reflection can be observed using a polarization-rotating light source.

Figure 31A:
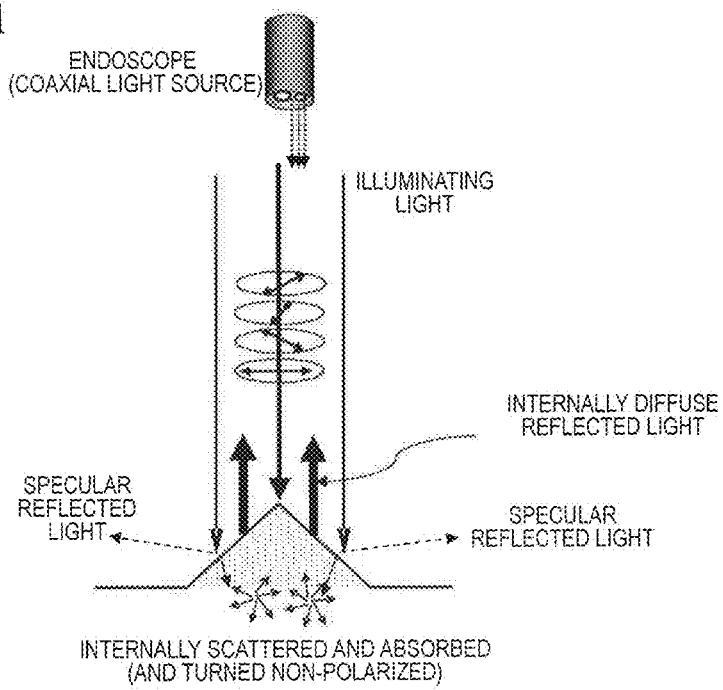
FIGS. 31A, 31B and 31C illustrate on what principle a variation in internally diffuse-reflected light is detected using a polarization-rotating light source according to the third embodiment.

FIG. 31A is a schematic representation illustrating how polarization-rotating illuminating light that has been incident on the slopes of a translucent projection from a light source right over the projection is reflected. As shown in FIG. 31A, the incoming illuminating light is incident on the slopes while rotating its plane of polarization sequentially. The specular reflected light does not return to the image capturing objective lens but just diverges, and does not contribute to the light intensity of the image captured. On the other hand, the light that has turned non-polarized after having been internally scattered and absorbed emerges from the slopes again and part of the light returns to the objective lens, and therefore, contributes to the light intensity of the image captured. When emerging from the slopes of the object, the light gets polarized. But the light intensity image sensor cannot measure the polarization. As a result, only a variation in light intensity that has been caused as a result of the rotation of the plane of polarization of the illuminating light is observed.

Next, it will be described with reference to FIGS. 31(B) and 31(C) why the light intensity varies.

Figure 31B:
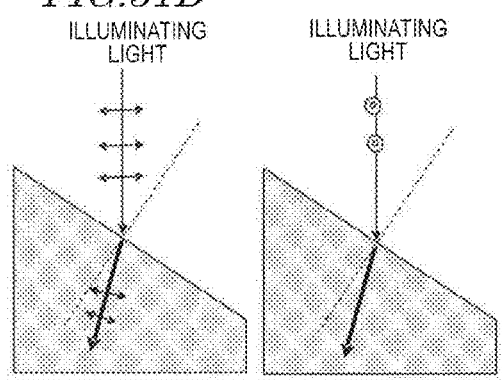
Figure 31C:
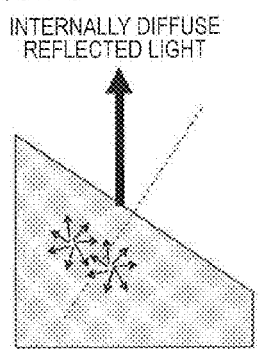
Figure 32:
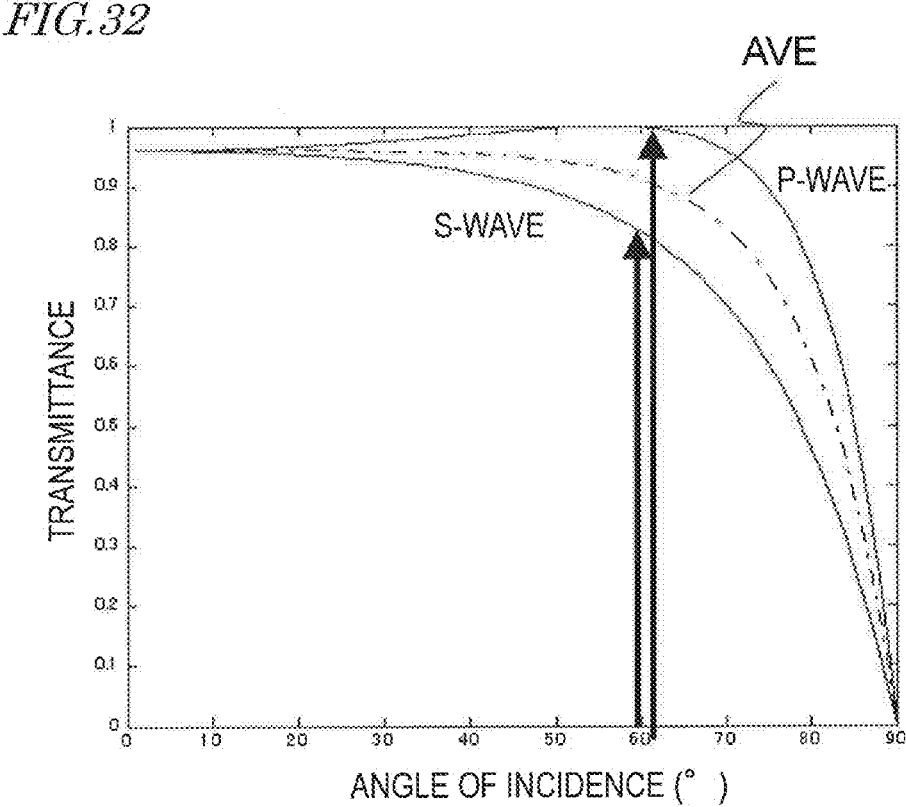
FIG. 32 is a graph showing, based on the Fresnel theory, how the quantities of P- and S-waves of light entering the medium change with the angle of incidence.

If the illuminating light that has been incident on the slope of the structure shown in FIGS. 31(B) and 31(C) is P-polarized light (which is polarized light, of which the electric field oscillation plane is on the paper), relatively a lot of light will enter the object. On the other hand, if the illuminating light is S-polarized light (which is polarized light, of which the electric field oscillation plane comes out of the paper), only a little light can enter the object. FIG. 32 is a graph based on the Fresnel theory showing relations between the light that has entered and the polarization. As can be seen from FIG. 32, at a boundary between the air with a refractive index of one and a medium with a refractive index of greater than one, a P wave will always prevail over the other waves, irrespective of the angle of incidence. That is why if polarization-rotating illuminating light is incident, the quantity of the light that enters the medium will vary. As a result, in the polarization-rotating light source, the intensity of the light emerging again through the surface (boundary) of the object into the air becomes maximum at an angle of rotation at which the incoming light corresponds to the P-polarized light and becomes minimum at an angle of rotation at which the incoming light corresponds to the S-polarized light as shown in FIG. 31C. In general, the variation in the intensity of the light going out of an object depends on the intensity of the incoming light, too. However, if incoming light propagates over a long distance through a medium with an internal structure, the internally diffused light emerges irrespective of the intensity of the incoming light. As a result, there will be no longer any correlation between the intensity of the internally diffused light and the light intensity of the polarization-rotating illuminating source.

Figure 33:
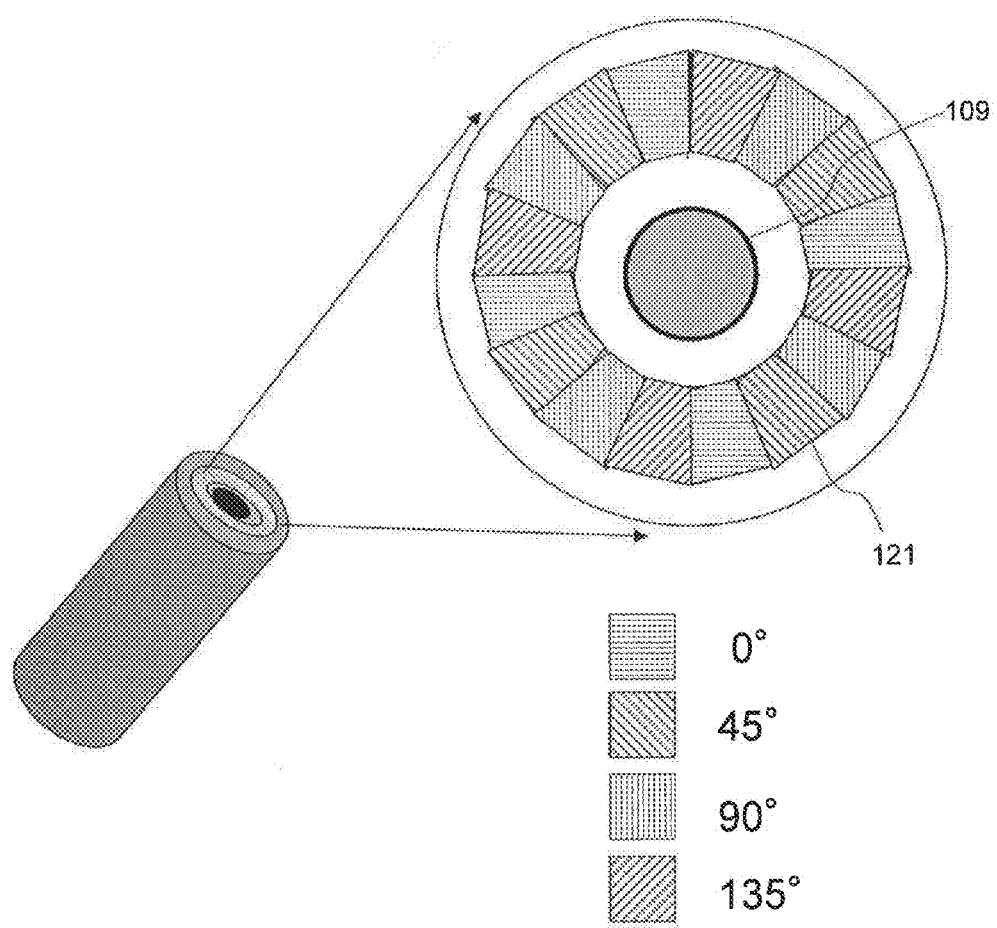
FIG. 33 illustrates the arrangement of polarizers of a polarization rotating light source at the tip portion of an endoscope according to the third embodiment of the present disclosure.

FIG. 33 illustrates the tip portion 106 of the endoscope and its portion through which the polarization-rotating illuminating light is emitted. In this configuration, the objective lens 109 arranged at the center is surrounded with a ring light source. And a plurality of polarizers 121, of which the polarization transmission axes face 0, 45, 90 and 135 degree directions, are arranged at the front end of the ring light source. More specifically, the illuminating portion of the ring light source is divided into sixteen sections, and a set of four polarizers 121, of which the polarization transmission axis directions are different from each other, are provided for each set of four divided sections of the illuminating portion. And by sequentially turning on the four divided sections of the illuminating portion associated with the four polarizers 121 one after another, a polarization-rotating light source is realized.

The micro polarizers 121 to be arranged in front of the ring light source may be formed by arranging wire grid polarizers or polarizers of a polymer film on a glass substrate. A polarizer array made of a polymer film is disclosed by Xiaojin Zhao, Farid Boussaid, Amin Bermak and Vladimir G. Chigrinov in "Thin Photo-Patterned Micropolarizer Array for CMOS Image Sensors", IEEE Photonics Technology Letters, Vol. 21, No. 12, Jun. 15, 2009.

A luminance variation processing section 400 detects the relation between the angle of the plane of polarization of the illuminating light and the luminance value of each pixel, thereby generating a "degree of luminance modulation image". In this description, the "degree of luminance modulation image" herein refers to an image which is defined by the ratio of the amplitude of the luminance value variation caused in each pixel by the change of planes of polarization to the average luminance value. For example, if the degree of luminance modulation at a certain pixel P (x, y) is 0.3, a value of 0.3 is set for this pixel P (x, y). A single "degree of luminance modulation image" is obtained by setting such a degree of luminance modulation value for each pixel.

A first image is captured in a state where the plane of polarization faces a 0 degree direction. A second image is captured in a state where the plane of polarization faces a 45 degree direction. A third image is captured in a state where the plane of polarization faces a 90 degree direction. And a fourth image is captured in a state where the plane of polarization faces a 135 degree direction. As it turned out that the luminance variation in a situation where the polarized light source has been rotated becomes a cosine function of the period of 180 degrees. That is why the luminance variation processing section 400 performs optimum fitting to a cosine function on that luminance variation. Supposing the angle of the plane of polarization of the illuminating light is $\psi_I$, the luminance variation can be expressed by the following Equation (11):

$$Y(\psi_I) = Y_{\psi_I\_ave} + A_I \cos(2(\psi_I - \psi_0)) \tag{11}$$

This processing is mathematically equivalent to the optimum fitting based on the luminance values that have been obtained by the polarization image sensor of the first and second embodiments using four-direction polarizers. That is why by carrying out the same procedure as the processing method described above on each set of corresponding pixels of the four images captured, a degree of luminance modulation image can be generated. This degree of luminance modulation image is generated by the degree of luminance modulation image generator 414 shown in FIG. 30. The degree of luminance modulation image retouching section 416 may carry out quite the same processing as that of the degree of retouching section 316 on the degree of luminance modulation image. The processing performed by the image synthesizing section 420 is the same, too. It should be noted that the light intensity image generator 412 generates a light intensity image by either adding together or averaging the luminance values obtained from respective pixels.

Embodiment 4

Figure 34:
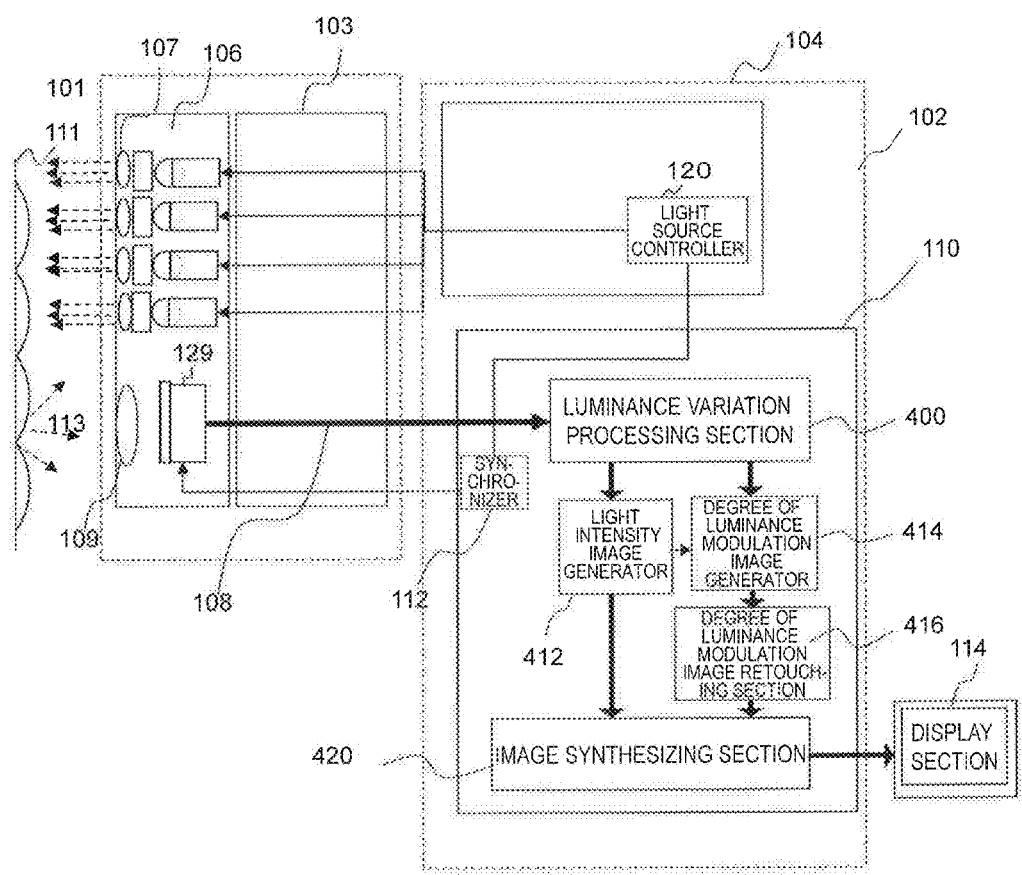
FIG. 34 illustrates a fourth embodiment of the present disclosure.

FIG. 34 schematically illustrates an overall configuration for an image capturing processor as a fourth embodiment of the present disclosure.

Unlike the third embodiment, to realize a polarization-rotating light source, no fiber-optics light sources or light guides are used but a surface-emitting light source such as an LED or an organic EL which is arranged at the tip portion of an endoscope is used in this embodiment.

In the third embodiment, sixteen divided radiation ports of illuminating light beams with different planes of polarization are arranged at the tip of the endoscope as shown in FIG. 33. If an image is captured with a set of four illuminating light beam ports selectively turned ON each time to rotate the plane of polarization, the illuminating light is emitted from a different position every fourth time, strictly speaking. That is why if the object produces a lot of specular reflection, the light sources of the four light beams emitted will be mirrored as they are on the object. As a result, a variation in light intensity due to the difference in light source position will be caused over the entire surface of the object to possibly cause an artifact that should not arise ordinarily. Thus, to avoid such a situation, according to this fourth embodiment, the illumination units to be sequentially turned ON have their size reduced sufficiently and their number increased significantly. In this manner, the spatial shift of the light intensity distribution due to the change of the positions of the light sources to turn ON can be reduced to one pixel or less on the image capturing side.

Figure 35:
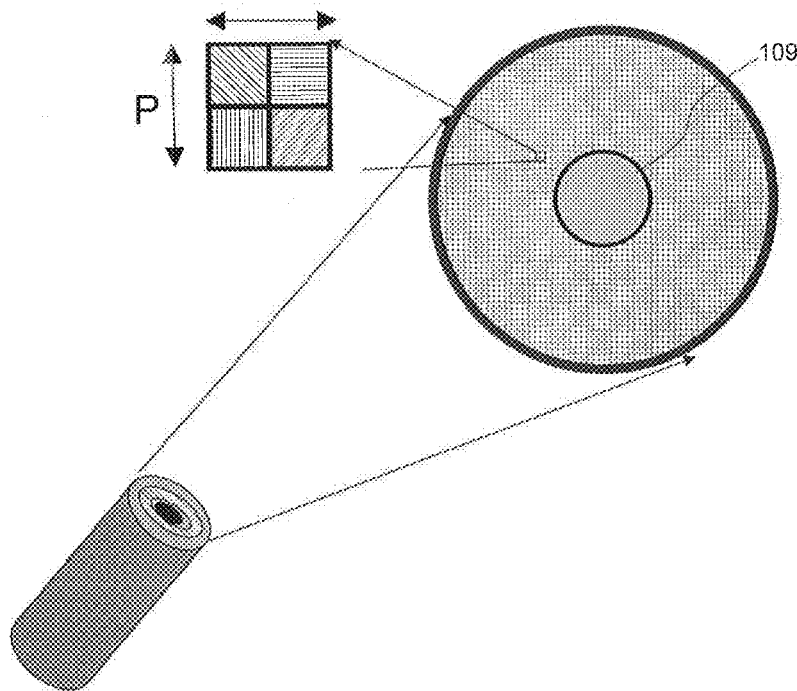
FIG. 35 illustrates a polarization rotating light source at the tip portion of an endoscope according to the fourth embodiment.

FIG. 35 illustrates the tip portion 106 of the endoscope and its portion through which polarization-rotating illuminating light beams are emitted. Even though only four polarizers are illustrated in FIG. 35 on a larger scale for convenience sake, a huge number of units, each being comprised of four polarizers, are actually arranged in columns and rows in the region surrounding the objective lens 109. In this configuration, the region surrounding the objective lens 109 arranged at the center functions as a surface-emitting light source. In the example illustrated in FIG. 35, four polarizers, of which the polarization transmission axes face 0, 45, 90 and 135 degree directions, are arranged in each square with a pitch of P×P.

Figure 36:
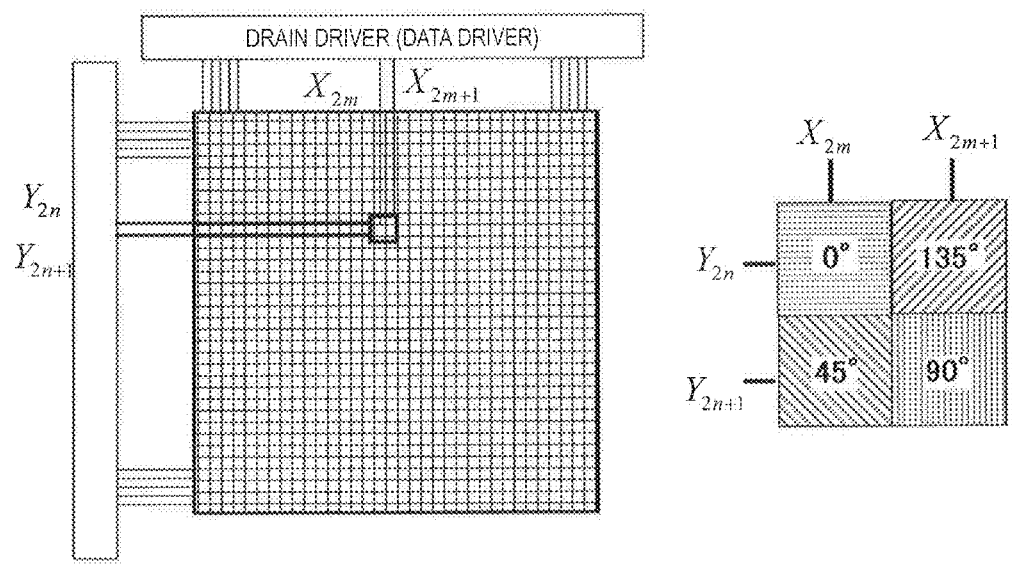
FIG. 36 illustrates a surface-emitting polarization-rotating light source according to the fourth embodiment.

FIG. 36 illustrates an overall configuration for this surface-emitting light source. A data driver which controls the sequential turn ON is provided for each of the X- and Y-axes of the surface-emitting light source, and pixels addressed on the X and Y axes are turned ON at a time. For example, if even-numbered pixels on both of the X and Y axes (X2m and Y2n) are turned ON at the same time, then illuminating light beams, of which the plane of polarization faces 0 degree direction, will be emitted. And by choosing even- and odd-numbered pixels in various combinations through the X- and Y-axis drivers, illuminating light beams, of which the plans of polarization face the 0, 45, 90 and 135 degree directions, can be obtained.

Figure 37:
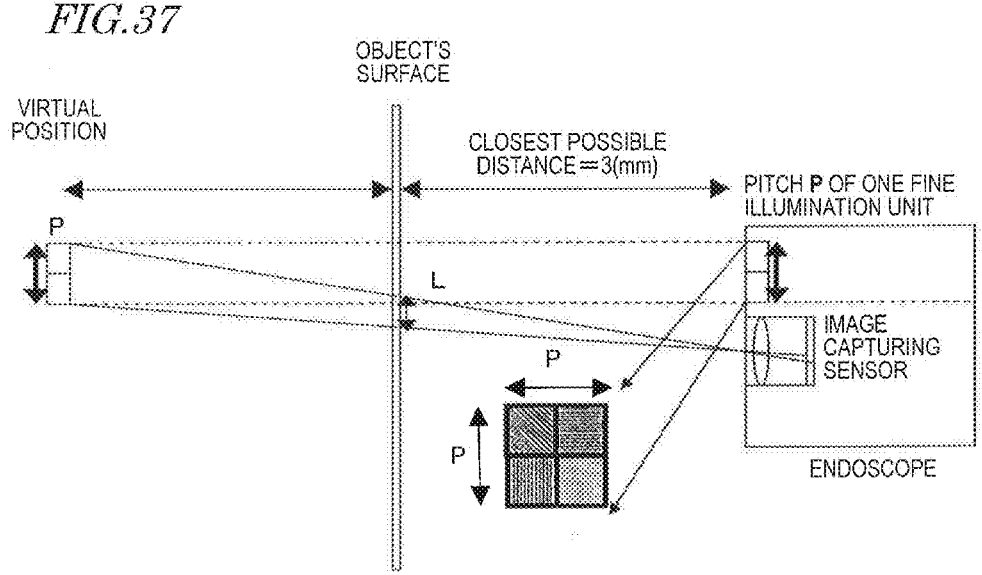
FIG. 37 shows a condition on the pixel size of a surface-emitting polarization-rotating light source according to the fourth embodiment.

FIG. 37 illustrates what effects will be achieved by reducing the illuminating pixel pitch of this surface-emitting light source sufficiently. Suppose the surface of the object is a smooth mirror surface such as a mucosa. If the surface is going to be shot with an endoscope brought close to it, the closest possible distance will be approximately 3 mm. In that case, if the viewing angle on a single side is 70 degrees, then the image capturing range is given by the following equation:

image capturing range=3×tan 70°×2=16.4 mm

If this image capturing range is going to be captured with an image sensor with a resolution of 1000×1000 pixels, the real size L of a single pixel (that is the limit of resolution) is given by the following equation:

$L$=16.4/1000=16.4 μm

The size of a single pixel to be actually shot will be 2L, considering the deeper virtual position of the object. That is why supposing this size corresponds to a single pixel of the image to be captured, the following relation is obtained:

$P \leq 2L$=32.8 μm

Consequently, if the pitch P of the illuminating pixels is equal to or smaller than 32.8 μm, the shift of the light source position will be too small to sense on the image and the artifact problem of the third embodiment can be overcome.

As for the endoscopes of the first through fourth embodiments, if the inserting portion 103 and the light source section 104 have their sizes reduced and separated from the control section, a capsule endoscope, of which the image capturing section has almost the same configuration, is obtained. A capsule endoscope is swallowed into a subject's body to shoot his or her entire digestive organ. However, since the internal body tissues are filled with water, the shooting session always needs to be carried out in water. The present inventors discovered and confirmed via experiments that this embodiment was also effective even when applied to shooting in water. That is why even with such a capsule endoscope in which an indigo carmine solution cannot be sprinkled, the surface micro-geometry of a translucent mucosa can also be detected and enhanced.

(Method of Making Monochrome Broadband Polarization Image Sensor)

Hereinafter, it will be described how to make a monochrome broadband polarization image sensor.

It will be described with reference to FIG. 38 how to make a metallic wire grid structure by either evaporating an aluminum (Al) layer or filing with a solution or paste agent including metallic nanoparticles and then by performing a lift-off process. The wire grid polarizers do not have to be made of Al but may also be made of any other metallic material such as Au, Ag, Cu or Ti.

Figure 38:
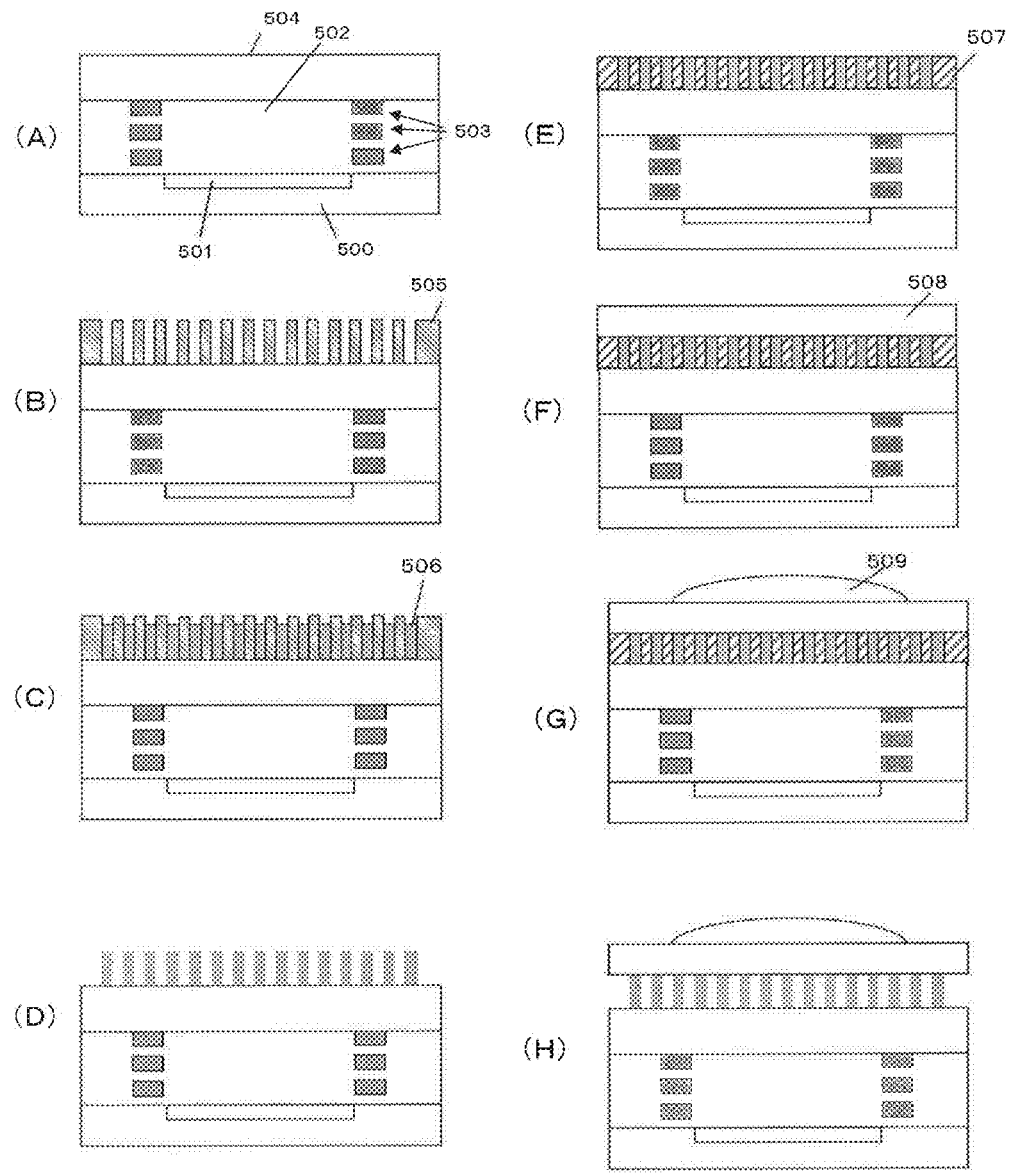
FIG. 38 illustrates an exemplary method for fabricating a wire grid polarizer for a monochrome broadband polarization image sensor.

In the structure illustrated in portion (A) of FIG. 38, a PD (photodiode) 501 has been formed on a substrate 500 of Si, and an interconnect layer 503 with a multilayer structure has been formed thereon with an interlayer film 502 interposed. The interconnect layer 503 is covered with a light-transmitting planarizing layer 504, which may be an inorganic insulating film of $SiO_2$, SiN or SiON or may be made of a resin (polymer) based material.

Next, in the process step shown in portion (B) of FIG. 38, a resist pattern 505, which exposes regions where the wire portions of the wire grid polarizers will be formed, is formed by photolithography on the planarizing layer 504.

Then, in the process step shown in portion (C) of FIG. 38, a metal layer 506 of Al, which is the material of wire grid polarizers, is deposited over the entire surface by either vacuum deposition process or sputtering process using the resist pattern 505 as a mask. Alternatively, the openings of the resist pattern 505 may be filled with Al by applying a solution including nanoparticles onto the entire surface instead of performing the vacuum deposition or sputtering process. To facilitate the lift-off, the metal layer 506 is suitably much thinner than the resist pattern 505. Wire grid polarizers of intended sizes and shapes may be formed by giving an inversely tapering shape to a single-layer resist pattern 505 or giving an overhanging shape to a resist pattern 505 with a multilayer structure. Thereafter, in the process step shown portion (D) of in FIG. 38, by removing the resist pattern 505 by lift-off method, a wire grid polarizer structure is completed.

Subsequently, in the process step shown in portion (E) of FIG. 38, to form a micro lens 509 over the wire grid polarizers, the gaps of the metal layer to be the wire grid polarizers are filled with a sacrificial layer 507. Next, in the process step shown in portion (F) of FIG. 38, an upper planarizing layer 508 of an inorganic or organic film is stacked on the sacrificial layer 507. Then, in the process step shown in portion (G) of FIG. 38, a lens film material of an inorganic or organic film is deposited on the upper planarizing layer 508 and patterned by photolithographic process into a resist pattern to form a micro lens. Next, by etching and etching back the lens film material using the resist pattern as a mask, a convex micro lens structure is formed.

Thereafter, in the process step shown in portion (H) of FIG. 38, the sacrificial layer that fills the gaps between the wire grid polarizers is selectively removed by etching the sacrificial layer from the surface outside of the micro lens region and from one end of the sacrificial layer that is exposed on the side surface of the wire grid polarizers, thereby completing the monochrome polarization image sensor structure shown in FIG. 14.

Next, it will be described with reference to FIG. 39 how to form wire grid polarizers by dry-etching a metal layer 605 of Al.

Figure 39:
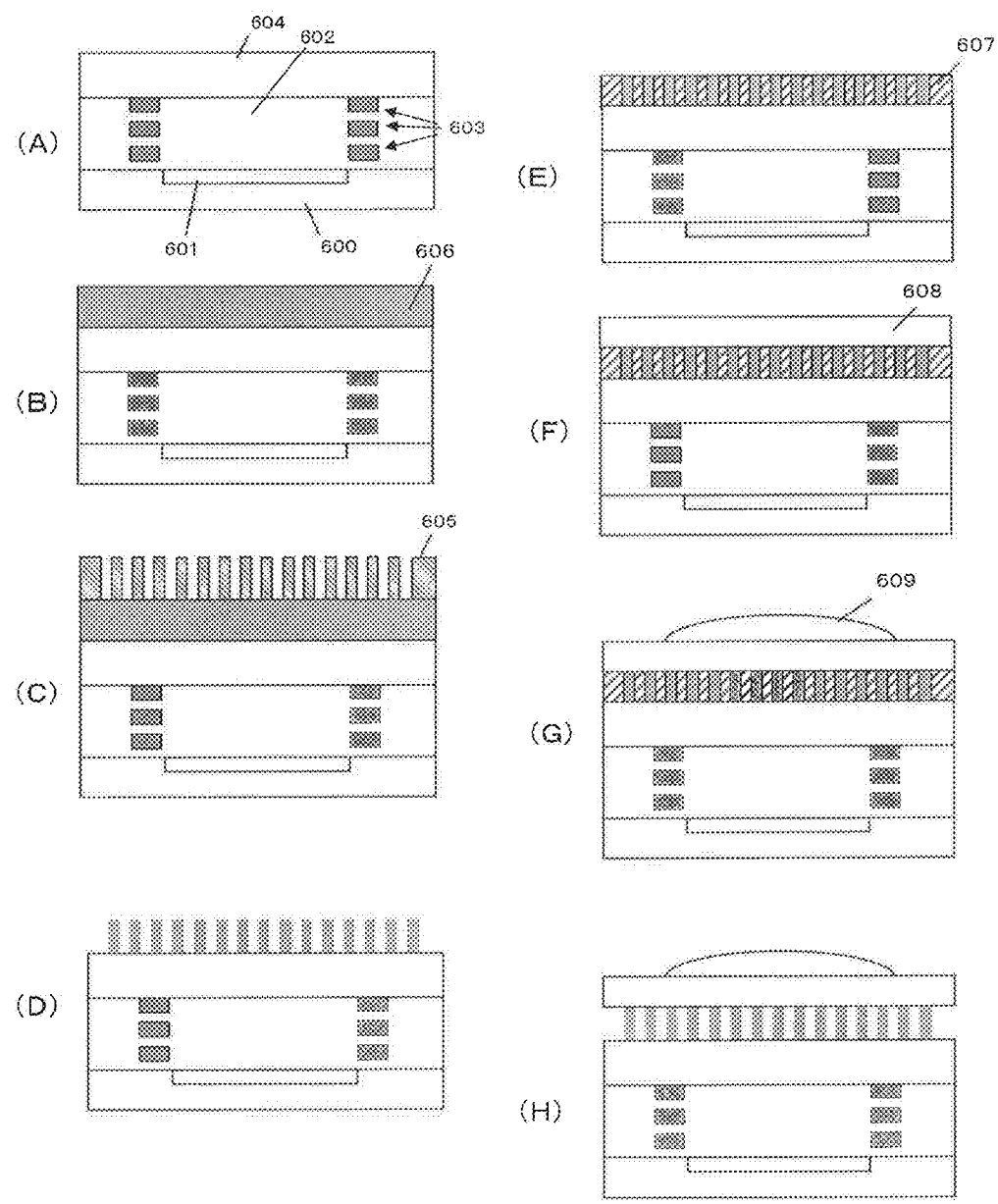
FIG. 39 illustrates another exemplary method for fabricating a wire grid polarizer for a monochrome broadband polarization image sensor.

In the structure shown in portion (A) of FIG. 39, a PD (photodiode) 601 has been formed on a substrate 600 of Si, on which an interconnect layer 603 has been formed with an interlayer film 602 interposed. The interconnect layer 603 is covered with a light-transmitting planarizing layer 604. Next, in the process step shown in portion (B) of FIG. 39, a metal layer 606 of Al is formed on the planarizing layer 604. Then, in the process step shown in portion (C) of FIG. 39, a resist pattern 605 to make wire grid polarizers is defined by photolithography.

Subsequently, in the process step shown in portion (D) of FIG. 39, an array of wire grid polarizers of Al is formed by dry-etching the metal layer 606 using the resist pattern 605 as a mask. The process steps shown in portions (E) to (H) of FIG. 39 are the same as their counterparts shown in FIG. 38, and description thereof will be omitted herein.

Next, it will be described with reference to FIG. 40 how to make wire grid polarizers by plating process.

Figure 40:
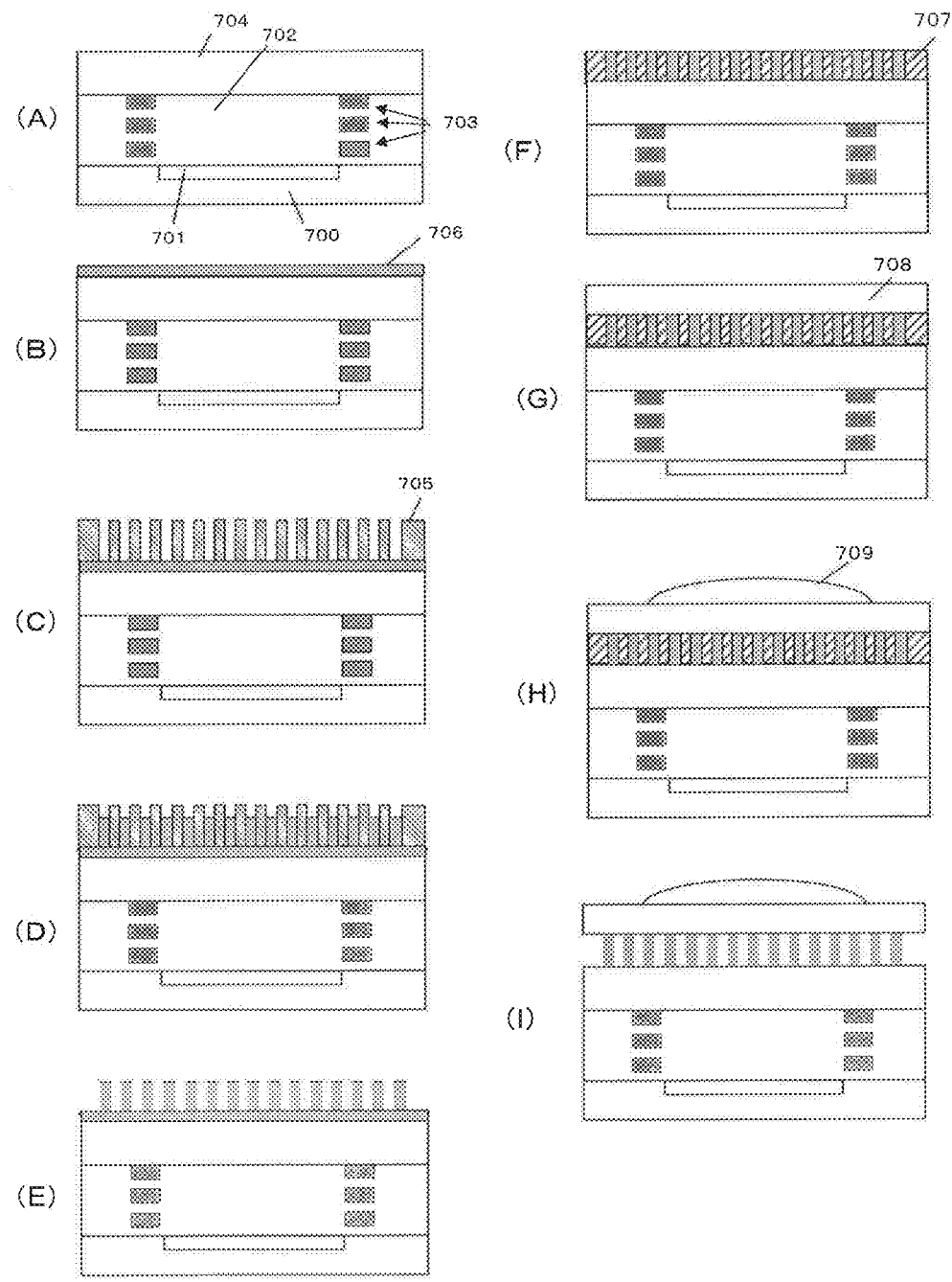
FIG. 40 illustrates still another exemplary method for fabricating a wire grid polarizer for a monochrome broadband polarization image sensor.

In the structure shown in portion (A) of FIG. 40, a PD (photodiode) 701 has been formed on a substrate 700 of Si, on which an interconnect layer 703 has been formed with an interlayer film 702 interposed. The interconnect layer 703 is covered with a light-transmitting planarizing layer 704.

Next, in the process step shown in portion (B) of FIG. 40, a thin metal layer 706 is formed on the planarizing layer 704. Then, in the process step shown in portion (C) of FIG. 40, a resist pattern 705 to make wire grid polarizers is defined by photolithography. Thereafter, in the process step shown in portion (D) of FIG. 40, the structure shown in portion (C) of FIG. 40 is dipped in an electroless plating solution using the resist pattern 705 as a mask, thereby selectively forming a plating metal layer in the openings of the resist pattern. Subsequently, in the process step shown in portion (E) of FIG. 40, the resist pattern 705 is removed, and the underlying metal layer 706 is dry-etched away to the planarizing layer 704 by using the plating metal layer on the wire grid polarizer pattern as a mask, thereby obtaining a metallic wire grid polarizer structure.

The process steps shown in portions (F) to (I) of FIG. 40 are the same as their counterparts shown in FIGS. 38 and 39, and description thereof will be omitted herein. Although the plating process step is supposed to be carried out as an electroless plating process in this example, an electro-plating process may also be adopted. Also, the wire grid polarizer pattern of the resist shown in FIGS. 38, 39 and 40 may be replaced with a pattern of nano-imprint.

Any of the other image sensors that have been described in this description may also be fabricated by one of these three kinds of manufacturing processes. If necessary, color filters are formed.

Embodiments of the present disclosure are broadly applicable to the field of image processing that needs observing, checking, or recognizing the object's surface topography using a medical endoscope camera for digestive organs, a medical camera for dermatologists, dentists, internists or surgeons, an industrial endoscope camera, a fingerprint scanner, or an optical surface analyzer for use in a factory, for example. Among other things, in the case of the micro-geometry on the surface of a smooth transparent object or translucent object, the bright and dark pattern cannot be observed just by measuring the light intensity due to the internally diffuse-reflected light. According to the present disclosure, however, the surface topography can also be detected accurately, and can be presented in an enhanced form so as to be easily sensible to a human viewer in a mode in which the concaves and convexes of the micro-geometric surface are displayed in low and high light intensities (i.e., as dark and bright portions), respectively. As a result, the surface topography which is difficult to check just by measuring the light intensity can be checked out very effectively according to the present disclosure.

A monochrome broadband polarization image sensor and a color polarization image sensor including wire grid polarizers which operate in the visible radiation wavelength range and which have a high extinction ratio are applicable to digital cameras, camcorders and surveillance cameras, and can be used extensively to increase the contrast ratio when shooting on the surface of water or in the air or when shooting through glass.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:
1. An imaging device comprising:
a camera that emits an illuminating light beam, the camera including an image sensor that captures a polarization image of an object being illuminated with the illuminating light beam; and
an image processor,
wherein the optical axis of the illuminating light beam and an image capturing optical axis are substantially coaxial with each other, and
the image processor comprises:
a light intensity image generator which generates a light intensity image based on the output of the image sensor;
a polarization degree image generator which generates a polarization degree image by calculating the degree of polarization on a pixel-by-pixel basis based on the output of the image sensor;

a retouching section which generates a retouched polarization image by enhancing the degree of polarization of the polarization degree image at concaves on a micro-geometric surface of the object and by correcting at least one of its hue, saturation and value; and an image synthesizing section which synthesizes the retouched polarization image and the light intensity image together, wherein the retouching section generates the retouched polarization degree image by decreasing the light intensity of concaves on the micro-geometric surface of the object of the polarization degree image.

2. The imaging device of claim 1, wherein the camera sequentially emits, as the illuminating light beams, non-polarized light beams in different colors, and the image sensor includes an array of polarizers and an array of photoelectric transducers.

3. The imaging device of claim 2, wherein the array of polarizers has a polarizer mosaic structure in which a plurality of polarizer units are arranged in columns and rows, each said polarizer unit including four polarizers, of which the polarization transmission axes directions are different from each other and which are arranged in two columns and two rows.

4. The imaging device of claim 3, wherein the polarization degree image generator determines the degree of polarization based on the square of the difference between two pixel values which are associated with two diagonal polarizers in the two by two matrix of each said polarizer unit.

5. The imaging device of claim 2, wherein the camera emits time-sequentially non-polarized light beams in red, green and blue, and the image sensor is a monochrome broadband polarization image sensor which is able to obtain a polarization image in the entire visible radiation wavelength range.

6. The imaging device of claim 2, wherein the array of polarizers is an arrangement of metallic wire grid polarizers which have mutually different polarization transmission axis directions.

7. The imaging device of claim 2, wherein the image sensor includes a micro lens which is arranged either closer to, or more distant from, the object than the array of polarizers is.

8. The imaging device of claim 2, wherein each said polarizer in the array of polarizers is a wire grid polarizer including a plurality of metallic wires, of which the side surface is in contact with the air.

9. The imaging device of claim 1, wherein the camera emits a non-polarized white light beam as the illuminating light beam, and the image sensor includes an array of polarizers, an array of color mosaic filters and an array of photoelectric transducers.

10. The imaging device of claim 9, wherein the image sensor is a color polarization image sensor.

11. The imaging device of claim 9, wherein the image sensor includes an array of micro lenses, and the array of micro lenses, the array of polarizers, and the array of color mosaic filters are arranged in this order so that the array of micro lenses is closer to a light source than any of the other arrays is.

12. The imaging device of claim 11, wherein a pixel which is associated with a color filter in one color in the array of color mosaic filters has a subpixel structure, which is associated with multiple polarization filters that have mutually different polarization transmission axis directions.

13. The imaging device of claim 9, wherein the image sensor includes an array of micro lenses, and the array of color mosaic filters, the array of micro lenses, and the array of polarizers are arranged in this order so that the array of color mosaic filters is closer to a light source than any of the other arrays is.

14. The imaging device of claim 9, wherein the image sensor includes an array of micro lenses, and the array of color mosaic filters, the array of polarizers and the array of micro lenses are arranged in this order so that the array of color mosaic filters is closer to a light source than any of the other arrays is.

15. The imaging device of claim 1, wherein the camera sequentially emits polarized light beams, of which the polarization plane faces at least three different directions, as the illuminating light beams, and the image sensor includes an array of color mosaic filters and an array of photoelectric transducers.

16. The imaging device of claim 1, wherein the retouching section sets the color saturation to be the enhanced degree of polarization and also sets the color hue and value to be particular numerical values, thereby converting a set of the hue, saturation and value from an HSV space into an RGB space.

17. The imaging device of claim 16, wherein the retouching section generates the retouched polarization degree image so that the concaves on the micro-geometric surface are displayed in dark blue.

18. The imaging device of claim 1, wherein the polarization degree image generator detects points with local maximum intensities of a polarized light beam which is produced by double reflection from the micro-geometric surface of the object and a polarized light beam resulting from internally diffused light in the object as the concaves on the micro-geometric surface of the object.

19. The imaging device of claim 1, wherein the camera is an endoscope.

20. The imaging device of claim 19, wherein the camera is housed in a container having a capsule shape.

21. The imaging device of claim 1, wherein the camera has a built-in light source which emits the illuminating light beam.

22. An image processor to be used as the image processor in the imaging device of claim 1, the image processor comprising:

a light intensity image generator which generates a light intensity image based on the output of the image sensor;

a polarization degree image generator which generates a polarization degree image by calculating the degree of polarization on a pixel-by-pixel basis based on the output of the image sensor;

a retouching section which generates a retouched polarization image by enhancing the degree of polarization of the polarization degree image at depressions on a micro-geometric surface of the object and by correcting at least one of its hue, saturation and value; and an image synthesizing section which synthesizes the retouched polarization image and the light intensity image together.

23. An endoscope to be used in the imaging device of claim 1, wherein the endoscope includes an image sensor that emits an illuminating light beam and that captures a polarization image of an object being illuminated with the illuminating light beam and the endoscope is arranged so that the optical axis of the illuminating light beam and an image capturing optical axis are substantially coaxial with each other.

24. An image processing method for performing image processing based on data about a polarization image that has been captured by an image sensor in a state where an object is illuminated with an illuminating light beam so that the optical axis of the illuminating light beam and an image capturing optical axis are substantially coaxial with each other, the method comprising performing, using a computer, the steps of:

generating a light intensity image based on the output of the image sensor;

generating a polarization degree image by calculating the degree of polarization on a pixel-by-pixel basis based on the output of the image sensor;

generating a retouched polarization image by enhancing the degree of polarization of the polarization degree image at depressions on a micro-geometric surface of the object and by correcting at least one of its hue, saturation and value, a light intensity of concaves on the micro-geometric surface of the object of the polarization degree image being decreased; and synthesizing the retouched polarization image and the light intensity image together.

25. A non-transitory computer readable medium having stored thereon an image processing program for performing image processing based on data about a polarization image that has been captured by an image sensor in a state where an object is illuminated with an illuminating light beam so that the optical axis of the illuminating light beam and an image capturing optical axis are substantially coaxial with each other, the program being defined, when executed by a computer, cause the computer to execute the steps of:

generating a light intensity image based on the output of the image sensor;

generating a polarization degree image by calculating the degree of polarization on a pixel-by-pixel basis based on the output of the image sensor;

generating a retouched polarization image by enhancing the degree of polarization of the polarization degree image at depressions on a micro-geometric surface of the object and by correcting at least one of its hue, saturation and value, a light intensity of concaves on the micro-geometric surface of the object of the polarization degree image being decreased; and synthesizing the retouched polarization image and the light intensity image together.

\* \* \* \* \*